(12) United States Patent
Orkin et al.

(10) Patent No.: US 10,472,619 B2
(45) Date of Patent: Nov. 12, 2019

(54) TARGETING BCL11A DISTAL REGULATORY ELEMENTS FOR FETAL HEMOGLOBIN REINDUCTION

(71) Applicant: The Children's Medical Center Corporation, Boston, MA (US)

(72) Inventors: Stuart H. Orkin, Brookline, MA (US); Daniel E. Bauer, Cambridge, MA (US); Jian Xu, Plano, TX (US)

(73) Assignee: The Children's Medical Center Corporation, Boston, MA (US)

( * ) Notice: Subject to any disclaimer, the term of this patent is extended or adjusted under 35 U.S.C. 154(b) by 0 days.

(21) Appl. No.: 15/816,083

(22) Filed: Nov. 17, 2017

(65) Prior Publication Data
US 2018/0119130 A1    May 3, 2018

Related U.S. Application Data

(62) Division of application No. 14/647,547, filed as application No. PCT/US2013/072236 on Nov. 27, 2013, now Pat. No. 9,822,355.

(60) Provisional application No. 61/889,174, filed on Oct. 10, 2013, provisional application No. 61/776,144, filed on Mar. 11, 2013, provisional application No. 61/730,323, filed on Nov. 27, 2012, provisional application No. 61/730,369, filed on Nov. 27, 2012.

(51) Int. Cl.

| | |
|---|---|
| C12N 15/12 | (2006.01) |
| A61K 35/28 | (2015.01) |
| C12N 5/078 | (2010.01) |
| C12N 15/01 | (2006.01) |
| C07K 14/805 | (2006.01) |
| C12N 15/10 | (2006.01) |
| C12N 15/63 | (2006.01) |
| C07K 14/47 | (2006.01) |
| A61K 35/12 | (2015.01) |
| A61K 38/46 | (2006.01) |
| C12N 9/22 | (2006.01) |

(52) U.S. Cl.
CPC ............ *C12N 15/01* (2013.01); *A61K 35/12* (2013.01); *A61K 38/465* (2013.01); *C07K 14/4702* (2013.01); *C07K 14/805* (2013.01); *C12N 9/22* (2013.01); *C12N 15/102* (2013.01); *C12N 15/63* (2013.01)

(58) Field of Classification Search
None
See application file for complete search history.

(56) References Cited

U.S. PATENT DOCUMENTS

| | | | |
|---|---|---|---|
| 5,928,638 A | 7/1999 | Uchida et al. | |
| 9,228,185 B2 | 1/2016 | Orkin et al. | |
| 9,885,041 B2 | 2/2018 | Orkin et al. | |
| 2005/0227917 A1 | 10/2005 | Williams et al. | |
| 2008/0051431 A1 | 2/2008 | Verhelle et al. | |
| 2010/0273213 A1 | 10/2010 | Mineno et al. | |
| 2011/0182867 A1 | 7/2011 | Orkin et al. | |
| 2014/0018410 A1 | 1/2014 | Novobrantseva et al. | |

FOREIGN PATENT DOCUMENTS

| | | |
|---|---|---|
| EP | 2334794 B1 | 11/2016 |
| EP | 2334794 B8 | 4/2017 |
| WO | 2009/007685 A2 | 1/2009 |
| WO | 2011/072086 A1 | 6/2011 |
| WO | 2012/073047 A2 | 6/2012 |
| WO | 2015/065964 A1 | 5/2015 |
| WO | 2016/182893 A1 | 11/2016 |

OTHER PUBLICATIONS

Hancarova et al, A Patient With De Novo 0.45 Mb Deletion of 2p16.1:The Role of BCL11A, PAPOLG, REL, and FLJ16341 in the 2p15-p16.1 Microdeletion Syndrome, Am J Med Genet Part A, 2013, 161A:865-870.*
Liu et al, Functional studies of BCL11A: characterization of the conserved BCL11A-XL splice variant and its interaction with BCL6 in nuclear paraspeckles of germinal center B cells, Molecular Cancer 2006, 5:18, pp. 1-16.*
Bauer et al, HbF-Associated Genetic Variation Marks an Erythroid Regulatory Element Essential for BCL11A Transcription and Subsequent Stage-Specific Globin Expression, Blood 2012 120:828; pp. 1-2.*
Akinsheye, I. et al., Blood,118(1):19-27 (Jul. 7, 2011). Prepublished online Apr. 13, 2011. doi: 10.1182/blood-2011-03-325258. "Fetal Hemoglobin in Sickle Cell Anemia."
Amaya et al., "Mi2β-mediated silencing of the fetal γ-globin gene in adult erythroid cells," Blood, 121(17):3493-501 (2013).
Amendah et al., "Sickle cell disease-related pediatric medical expenditures in the U.S.", Am J Prev Med, 38(4 Suppl): S550-6 (2010).
Atweh et al., Seminars in Hematology, 38(4):367-73 (2001). "Pharmacological induction of fetal hemoglobin in sickle cell disease and beta-thalassemia."
Bauer et al., "An Erythroid Enhancer of BCL11A Subject to Genetic Variation Determines Fetal Hemoglobin Level" Science, 342(6155):253-57 (2013).
Bauer et al., Blood 120(15):2945-2953 (2012). "Reawakening fetal hemoglobin: prospects for new therapies for the B-globin disorders".
Bohmer et al., Prenatal Diagnosis, 19:628-636 (1999). "Identification of fetal nucleated red cells in co-cultures from fetal and adult peripheral blood: differential effects of serum on fetal and adult erythropoiesis."
Bunn et al., New Engl. J. Med., 328(2):129-131 (1993). "Reversing ontogeny."
Canver et al., "BCL11A enhancer dissection by Cas9-meidated in situ saturating mutagenesis." Nature, 527(7577):192-7 (2015).

(Continued)

*Primary Examiner* — Maria Marvich
(74) *Attorney, Agent, or Firm* — Nixon Peabody, LLP

(57) ABSTRACT

Provided herein are methods and compositions for increasing fetal hemoglobin levels in a cell by disrupting BCL11A expression at the genomic level. Also provided herein are methods and compositions relating to the treatment of hemoglobinopathies by reinduction of fetal hemoglobin levels.

14 Claims, 12 Drawing Sheets

Specification includes a Sequence Listing.

(56) References Cited

OTHER PUBLICATIONS

Cao et al., Pediatric Reports 3(2):65-71 (2011). "Recent advances in B-thalassemias".
Chabchoub et al., "The facial dysmorphy in the newly recognised microdeletion 2p15-p16.1 refined to a 570 kb region in 2p15", J Med Genet, 45(3):189-92 (2008).
Coleman et al., Clinical Pediatrics, 46(5):386-391 (2007). "Sickle cell anemia: targeting the role of fetal hemoglobin in therapy."
Cox et al., "Therapeutic genome editing: porspects and challenges", Nature Medicine, 21(2):121-131 (2015).
Dixit et al., "Hydroxyurea in thalassemia intermedia—a promising therapy." Annals of Hematology 84(7):441-446 (2005).
Fenaux, "Inhibitors of DNA methylation: beyond myelodysplastic syndromes", Nat Clin Pract Oncol., 2:S36-S44 (2005).
Fischer et al., "Pulmonary Passage is a Major Obstacle for Intravenous Stem Cell Delivery: The Pulmonary First-Pass Effect", Stem Cells and Development, 18(5):683-91 (2009).
Flanagan et al., "Hydroxycarbamide alters erythroid gene expression in children with sickle cell anaemia." British Journal of Haematology 157(2):240-248 (2012).
GeneCard for BCL11A, retrieved from http://www.genecards.org/cgi-bin/carddisp.pl?gene=BCL11A on Jun. 22, 2012.
Goffin et al., "DNA methyltransferase inhibitors-state of the art", Ann Oncol.,13(11):1699-716 (2002).doi: 10.1093/annonc/mdf314.
Goldberg et al., "Treatment of sickle cell anemia with hydroxyurea and erythropoietin." New England Journal of Medicine 323(6):366-372 (1990).
Hackam "Translating animal research into clinical benefit", BMJ, 334:163-68 (2007).
Harding et al., "Large animal models for stem cell therapy", Stem Cell Research & Therapy 4:23:1-9 (2013).
Hebbel et al., "The HDAC inhibitors trichostatin A and suberoylanilide hydroxamic acid exhibit multiple modlaties of benefit for the vascular pathobiology of sickle transgenic mice", Blood, 115(12):2483-90 (2010).
Higgs et al., Proceedings of the National Academy of Sciences, 105(33):11595-11596 (2008). "Genetic complexity in sickle cell disease."
Ho et al., "In vitro induction of fetal hemoglobin in human erythroid progenitor cells." Experimental Hematology 31(7):586-591 (2003).
Hsieh et al., "Allogeneic hematopoietic stem-cell transplantation for sickle cell disease", N Engl J Med, 361(24):2309-17 (2009).
Jane et al., Br. J. Haematol., 102:415-422 (1998). "Understanding fetal globin gene expression: a step towards effective HbF reactivation in haemoglobinopathies."
Kauf et al., "The cost of health care for children and adults with sickle cell disease", Am J Hematol, 84(6):323-7 (2009).
Kirschner et al., "Genomic mapping of chromosomal region 2p15-p21 (D2S378-D2S391): integration of Genemap'98 within a framework of yeast and bacterial artificial chromosomes", Genomics, 62(1):21-33 (1999).
Koshy et al., "2-deoxy 5-azacytidine and fetal hemoglobin induction in sickle cell anemia", Blood, 96(7):2379-84 (2000).
Labie, Hematologie, 14(2):165-166 (2008). "Le controle en trans de la production dEhemoglobine flltale: une recherche qui dure deupis 20 ans."
Lettre, G. et al., PNAS, 105(33):11869-11874 (2008). "DNA polymorphisms at the BCL11A, HBS1L-MYB, and beta-globin loci associate with fetal hemoglobin levels and pain crises in sickle cell disease."
Liu et al., Nature Immun, 4:525-532 (2003). "Bcl11a is essential for normal lymphoid development." ((from Prov)).
Lulli et al., "MicroRNA-486-3p regulates γ-globin expression in human erythroid cells by directly modulating BCL11A," PLoS One, 8(4):e60436 (2013).
Makala et al., "Fetal Hemoglobin Induction to Treat b-Hemoglobinopathies: From Bench to Bedside", J Hematol Transfus, 2(2):1-2 (2014).

Martin-Subero et al., Blood, 99:1474-1477 (2002). "Recurrent involvement of the REL and BCL11A loci in classical Hodgkin lymphoma." ((from Prov)).
Menzel et al., Nature Genetics, 39(10):1197-1199 (2007). "A QTL influencing F cell production maps to a gene encoding a zinc-finger protein on chromosome 2p15."
Migliaccio et al., Blood 76(6):1150-1157 (1990). "Influence of recombinant hematopoietins and of fetal bovine serum on the globin synthetic pattern of human BFUe."
Nemudryi et al., "TALEN and CRISPR/Cas Genome Editing Systems: Tools of Discovery",Acta Naturae, 6(3):19-40 (2014).
Neven et al., "A Mendelian predisposition to B-cell lymphoma caused by IL-10R deficiency," Blood, 3713-22 (2013).
Orkin et al., Annals of the New York Academy of Sciences, 1368 (1):5-10 (2016). "Recent advances in globin research using genome-wide association studies and gene editing."
Papayannopoulou et al., Science, 199:1349-1350 (1978). "Erythroid progenitors circulating in the blood of adult individuals produce fetal hemoglobin in culture."
Pauling et al. "Sickle cell anemia a molecular disease", Science, 110(2865):543-8 (1949).
Pembrey et al., Br. J. Haematol., 40: 415-429 (1978). "Fetal haemoglobin production and the sickle gene in the bases of Eastern Saudi Arabia."
Perrine, "Fetal globin induction—can it cure beta thalassemia?", Hematology Am Soc Hematol Educ Program, pp. 38-44 (2005).
Platt et al., "Mortality in sickle cell disease. Life expectancy and risk factors for early death", N Engl J Med, 330(23):1639-44 (1994).
Purton et al., "All-trans retinoic acid enhances the long-term repopulating activity of cultured hematopoietic stem cells." Blood 95(2):470-477 (2000).
Ridley et al., "Erythropoietin: A Review", J Natl Med Assoc., 86(2):129-35 (1994).
Rodriguez et al., "A bioavailability and pharmacokinetic study of oral and intravenous hydroxyurea." Blood 91(5):1533-1541 (1998).
Rosenblum et al., Experimental Approaches for the Study of Hemoglobin, 397 (1985). "Peripheral blood erythroid progenitors from patients with sickle cell anemia: HPLC separation of hemoglobins and the effect of a HbF switching factor."
Saiki et al., "Human EVI9, a homologue of the mouse myeloid leukemia gene, is expressed in the hematopoietic progenitors and down-regulated during myeloid differentiation of HL60 cells." Genomics 70(3):387-391 (2000).
Sankaran et al., American Society of Hematology Education Program Book 2011, 1:459-465 (2011). "Targeted therapeutic strategies for fetal hemoglobin induction".
Sankaran et al., Nature, 460(7259):1093-7 (2009). "Developmental and species-divergent globin switching are diriven by BCL11A." ((from Prov)).
Sankaran, V.G., Science, 322:1839-1842 (2008). "Human fetal hemoglobin expression is regulated by the developmental stage-specific repressor BCL11A."
Satterwhite et al., Blood, 98:3413-3420 (2001). "The BCL11 gene family: involvement of BCL11A in lymphoid malignancies." ((from Prov)).
Sedgewick, A.E., Blood Cells, Molecules and Diseases, 41:255-258 (2008). "BCL11A is a major HbF quantitative trait locus in three different populations with beta-hemoglobinopathies."
Shen et al., Experimental Hematology, 35(8):1209-1218 (2007). "Modifcation of globin gene expression by RNA targeting strategies."
Taymans et al., "Radiation hybrid mapping of chromosomal region 2p15-p16: integration of expressed and polymorphic sequences maps at the Carney complex (CNC) and Doyne honeycomb retinal dystrophy (DHRD) loci", Genomics, 56:344-9 (1999).
Thein, British Journal of Haematology, 145:455-467 (2009). "Discovering the genetics underlying foetal haemoglobin production in adults."
Thein, S.L., British Journal of Haematology, 141:357-366 (2008). "Genetic modifiers of the beta-haemoglobinopathies." ((from Prov)).
Thompson, "Structure, Function, and Molecular Defects of Factor IX", Blood, 67(3):565-72 (1986).

(56) References Cited

OTHER PUBLICATIONS

Uda, M. et al., PNAS, 105(5):1620-1625 (2008). "FGenome-wide association study shows BCL11A associated with persistent fetal hemoglobin and amelioration of the phenotype of beta-thalassemia."

Wang et al., "In Vivo Delivery Systems for Therapeutic Genome Editing", International Journal of Molecular Sciences, 17(5):1-19 (2016).

White et al., "Factor VIII Gene and Hemphililia A", Blood, 73(1):1-12 (1989).

World Health Organization. "Sickle-cell anaemia. Report A59/9. Provisional agenda item 11.4." 59th World Health Assembly. www.who.int/gb/ebwha/pdf_files/WHA59/A59_9-en.pdf (2006).

Xu et al., "Reactivation of silenced human HbF in adult mice by inactivation of BCL11A", Blood, 116(21):282-283 (2010).

Xu et al., Correction of sickle cell disease in adult mice by interference with fetal hemoglobin, Science 334(6058);993-996 (2011).

Xu et al., Genes Dev. 24:783-798 (2010). "Transcriptional silencing of beta-globin by BCL11A involvs long-range interactions and cooperation with SOX6".

Hendel et al., "Chemically modified guide RNAs enhance CRISPR-Cas genome editing in human primary cells." Nature Biotechnology 33(9):985-989 (2015).

Bauer et al., "Supplementary Material: An Erythroid Enhancer of BCL11A Subject to Genetic Variation Determines Fetal Hemoglobin Level." Science 342(6155):253-257 (2013).

Bjurström et al. "Reactivating fetal hemoglobin expression in human adult erythroblasts through BCL11A knockdown using targeted endonucleases." Molecular Therapy-Nucleic Acids 5:e351 (2016).

Boettcher et al., "Choosing the right tool for the job: RNAi, TALEN, or CRISPR." Molecular Cell 58(4):575-585 (2015).

Doench et al., "Rational design of highly active sgRNAs for CRISPR-Cas9-mediated gene inactivation." Nature Biotechnology 32(12):1262-1267 (2014).

Doench et al., "Supplementary Material: Rational design of highly active sgRNAs for CRISPR-Cas9-mediated gene inactivation." Nature Biotechnology 32(12):1262-1267 (2014).

Schopman et al. "Optimization of shRNA inhibitors by variation of the terminal loop sequence." Antiviral Research 86(2):204-211 (2010).

Sebastiani et al., "BCL11A enhancer haplotypes and fetal hemoglobin in sickle cell anemia." Blood Cells, Molecules and Diseases 54(3):224-230 (2015).

Terasawa et al., "Synthetic pre-miRNA-based shRNA as potent RNAi triggers." Journal of Nucleic Acids (2011).

Wang et al. "Genetic screens in human cells using the CRISPR/Cas9 system." Science 343(6166):80-84 (2013).

Wang et al. "Supplementary Material: Genetic screens in human cells using the CRISPR/Cas9 system." Science 343(6166):80-84 (2013).

Wang et al., "Selection of hyperfunctional siRNAs with improved potency and specificity." Nucleic Acids Research 37(22):e152 (2009).

* cited by examiner

FIG. 4A
FIG. 4B
FIG. 4C
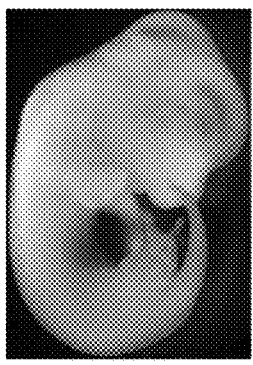
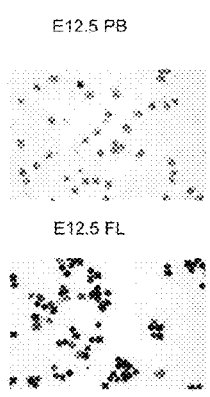
E12.5 PB
E12.5 FL
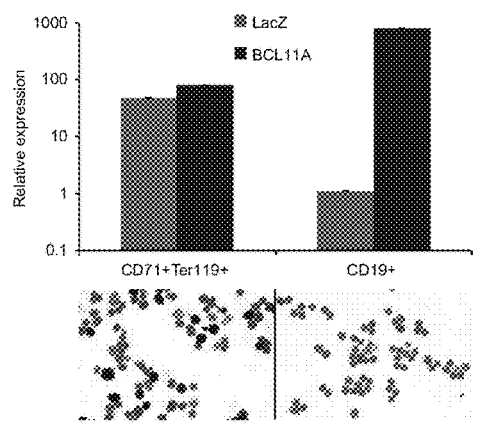

SEQUENCE LISTING

<160> NUMBER OF SEQ ID NOS: 215

<210> SEQ ID NO 1
<211> LENGTH: 9
<212> TYPE: PRT
<213> ORGANISM: Unknown
<220> FEATURE:

```
<223> OTHER INFORMATION: Description of Unknown:
      LAGLIDADG family meganuclease peptide

<400> SEQUENCE: 1

Leu Ala Gly Leu Ile Asp Ala Asp Gly
1               5

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cttaaggcaa gaatcact                                                 18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccatgccttt cccccct                                                  18

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gagttaaaat cagaaatct                                                19

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ctgactaatt gatcat                                                   16

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(12)
<223> OTHER INFORMATION: a, c, t, g, unknown or other

<400> SEQUENCE: 6
ctgnnnnnnn nngata                                                   16

<210> SEQ ID NO 7
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aaagagctgt ccgaagtcca                                                    20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gggcacttcc tagtccctct                                                    20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tttgagcagg agggaatttg                                                    20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atgttgtggt ccctgtggtt                                                    20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcaaggcagg taccaaacat                                                    20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tagagattcc aggccccttt                                                    20

<210> SEQ ID NO 13
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agcaaggaaa ggtgaagcag                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cccaatgtct tccgaactgt                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aggctggtct tgggattttt                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcctttaaca agggtgtcca                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
catagacctg ggtcctggaa                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ttgcagagtg actcctgtgg                                              20

<210> SEQ ID NO 19
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 19
ccagccatac ccaaaacaaa                                                    20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctttccctct tgccactcag                                                    20

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggcagagaag gcacagtga                                                     19

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggctgtcctg gcatgtaagt                                                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aacagaccca tgtgctaggc                                                    20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgtgtggact gccttttctg                                                    20

<210> SEQ ID NO 25
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 25
gggaaaaggg agaggaaaaa                                                    20

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctcagaaaaa tgacagcacc a                                                  21

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggactcagtg gcctcttttg                                                    20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gaagataatg gcagcccaga                                                    20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgtgtggcca acctgtaaaa                                                    20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctcgctctgt ttcccagttc                                                    20

<210> SEQ ID NO 31
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 31
ctctccgacg acctcttttg                                               20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gtagggaagg ggctacttgg                                               20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
agagccaaac tccgtctcaa                                               20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aaataccaca gcccaacagc                                               20

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gaacagagac cactactggc aat                                           23

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggggaagggg tattgaattg                                               20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 37
cttccactgg atggcacttt                                                 20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
acttcagcct ccagcactgt                                                 20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cctcccagca atgtaggtgt                                                 20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tggtgtggtc cactgtgact                                                 20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gcaagcttag ccccttcttt                                                 20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tgaggcagag tcagatgtgg                                                 20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 43
ccccgctcag agtaagtgag                                              20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ggaaactgcc tatcccatga                                              20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
caacaccccg atttcagact                                              20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gaatggtccc gatctcttga                                              20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tggtgaaggt cggtgtgaac                                              20

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ccatgtagtt gaggtcaatg aagg                                         24

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 49
aaccccagca cttaagcaaa                                                    20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
acaggtgaga aggtcgtggt                                                    20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gccccaaaca ggaacacata                                                    20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ggggcatatt ctgcactcat                                                    20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
atgcgagctg tgcaactatg                                                    20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gtaaacgtcc ttccccacct                                                    20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
```
cagctcaaaa gagggcagac                                               20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gagcttccat ccgaaaactg                                               20

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tggcctgtgg agtaaggtca a                                             21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gaagcagagg acaagttccc a                                             21

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tggacaacct caaggagacc                                               20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
acctctgggg tgaattcctt                                               20

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tttaacgatg gcctgaatca ctt                                              23

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cagcacaatc acgatcatat tgc                                              23

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gccaacattg agacacatgg                                                  20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tgtctctctg caccatcctg                                                  20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ttcaatgctg tcaggtgctc                                                  20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gccatgtgtc tcaatgttgg                                                  20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gtctgccctc ttttgagctg                                                  20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gactccagac aatcgccttt                                                     20

<210> SEQ ID NO 69
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
aaaggcgatt gtctggagtc aacctt                                              26

<210> SEQ ID NO 70
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
cttagcaccc acaaac                                                         16

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
catgttactg caacttgctt ttt                                                 23

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
agatccctcc gtccagctc                                                      19

<210> SEQ ID NO 73
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tgaaagttca agtagatatc agaagg                                              26

```
<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
agcaaaccac acagactgaa ga                                              22

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ccagagccat ttacgtcaca                                                 20

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cagaagggaa taaggtactc tgga                                            24

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gtttgggcct caaggtcttt                                                 20

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gaggttggga gtaagcattc tg                                              22

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
acgcatcaga atgcccatag                                                 20
```

```
<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ttttgaaaga aaacgctgac a                                              21

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ttccagctgg ttaaatttag gg                                             22

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
agaaggggcc agaagaacag                                                20

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83 ccttctttt ctttcttggt tgc                                             23

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ccctgcgtgc cattaaaata                                                20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
aaaggccttg ggaagaaaga                                                20

<210> SEQ ID NO 86
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gcaagtcagt tgggaacaca                                                   20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ggactcagtg gcctcttttg                                                   20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ctgtctctgt ctcccccaag                                                   20

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ccaatgctcc tgtaacaaag g                                                 21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
aatgcagtag gcaaagaagc a                                                 21

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gaaatttgga aggccacaga                                                   20

<210> SEQ ID NO 92
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
gcttgcaaca attaaaagat gg                                             22

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ggtgacaagg gagaaccact                                                20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
tgatttcctt gcagccttt                                                 20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
cacacccaca gcaacaaatg                                                20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
tgcagagatc ccccaaagta                                                20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
ctcagggagc aagggaaata                                                20

<210> SEQ ID NO 98
<211> LENGTH: 20
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 98
ccctcccaac agggatttat                                               20

<210> SEQ ID NO 99
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
caaaattgaa cacctatggt ctga                                          24

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
aggaagactt tggcctccat                                               20

<210> SEQ ID NO 101
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
ttccaaacaa ttatacacca acaaa                                         25

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
tttcatgggg aatagccaac                                               20

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ccctacttgt tatttgcttc tgc                                           23

<210> SEQ ID NO 104
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 104
agctgaagtt tcagggacca                                                20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ccacacctgc cttccttaga                                                20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
tgcatatgat ggggtagcag                                                20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
aagagaaggg ggaatttgga                                                20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
tggtgataag ggcaggaaac                                                20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
aggaagctgc agaaaggtga                                                20

<210> SEQ ID NO 110
<211> LENGTH: 20
<212> TYPE: DNA
<213> ORGANISM: Artificial Sequence
<220> FEATURE:
```

<223> OTHER INFORMATION: Description of Artificial Sequence: Synthetic
    primer

<400> SEQUENCE: 110
tgcttcccca ggtttagatg                                               20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 111
ccactgctac ccaaaacgat                                               20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 112
caagagcgaa actccacctc                                               20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 113
actgtgtgcc aagtgaccag                                               20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 114
cagcttcctt caggtgcttc                                               20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 115
catgctgcct ttgtcttctg                                               20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 116
tgtggagctc tggaatgatg                                                20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gagctccaca atccaactcc                                                20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
ccaggaagga aatgagaacg                                                20

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
acccacaaac atttcccttc t                                              21

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
tttgctcttc tccagggtgt                                                20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
tttaaacagc caccccacac                                                20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
accacgtagt tgggcttcac					20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
tttcaaccat ggtcatctgc					20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
ccctctggca tcaaaatgag					20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gaacctggga ggcagaagat					20

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
tttttggtga gacggagatt t					21

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
ccgggcaaca agagtaaatc					20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 128
atgcctaggg tgttttgacg                                               20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
ctccgtgttg agagccaagt                                               20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
tgtgtggact gccttttctg                                               20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
cagaaaaggc agtccacaca                                               20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
cctctccaga ttccctctca                                               20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
agcgagaccc tgtctcaaaa                                               20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
```

-continued tccagcaggc ttcaaaaagt                                               20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
ggtggataac cccatctcag                                               20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
ggaaatgaga atgcccttttg                                              20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
cagtctagaa agcccctca                                                20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138 gtggggttc agtggttaga                                                20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
tccatggtgt ggagtgtgtt                                               20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140

```
acccacatgg caaccaatag                                                    20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
ccattccctg gagagttcaa                                                    20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
ggggtctctt cccatcattt                                                    20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
atgggaagag accccaaaac                                                    20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
ggactccgaa caccacactt                                                    20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
gggatcagag gtgaacagga                                                    20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
tttaatcagc ttccgccact                                                    20
```

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
tggggagaga agagtggaaa                                              20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
ttgccaattg gagattaggg                                              20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
tgctccgagc ttgtgaacta                                              20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
gggaaagggc ctgataactt                                              20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
gagagtgcag acaggggaag                                              20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
cctctttcgg aaggctctct                                              20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 153
tggactttgc actggaatca                                          20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 154
gatggctgaa aagcgataca                                          20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 155
ggggagatga ttgaaagcaa                                          20

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 156
agaactttcc cggttctggt                                          20

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 157
gctctggaca cacagcaaaa                                          20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 158
tcaaatcctt gccttgaacc                                          20

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 159
cctcaaatct ccctcactgg     20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 160
gggaaatggg tcctgcttta     20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 161
agggagtaca ccgcagacac     20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 162
aaggaaggct gcaaggaaat     20

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 163
gacttaaact gccgctcctg     20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 164
tgactggtaa gagccgattg     20

<210> SEQ ID NO 165

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
gctggggtga gtcaaaagtc                                               20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
ggtcacctta aggagccaca                                               20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
gcacctgcat ttgttttca                                                20

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
gggtcagatc acctctgctc                                               20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
aggcatccaa agggaagaat                                               20

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
gaagataatg gcagcccaga                                               20

<210> SEQ ID NO 171
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
tgggaaaggt tgcacattct                                              20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
gggcctcagg ctctttatct                                              20

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
ccactgccag gctgtttact                                              20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
gaccgaaagg aggagaggag                                              20

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
cagttccccc attatgcact                                              20

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
cccttctctg aaggcacatc                                              20

<210> SEQ ID NO 177
<211> LENGTH: 20
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 177
ttcaagcctt ggtggatagg                                              20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
gccaggaaat tggtggtaga                                              20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
tgcccacatg agacatcttt                                              20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
aaattggctg ccattgaatc                                              20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
ccaccagaag tcctggaaaa                                              20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
ttggagggac ctgatctctg                                              20

<210> SEQ ID NO 183
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 183
ccaagatgga gaagccacat                                                    20

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
tctgtcttgg gtctcctggt                                                    20

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
gagaagccct cagcaaacac                                                    20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
ggttgcatct tggctcctaa                                                    20

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
gaaatgcagg aaaggaacga                                                    20

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
tctagcagat ggggttttgg                                                    20

<210> SEQ ID NO 189
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 189
agtctgggca acaaagtgag a                                                21

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
agaaactgag gagaaggatg                                                  20

<210> SEQ ID NO 191
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
atagaccatg agtagagggc agac                                             24

<210> SEQ ID NO 192
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
tgatcctgaa aacataggag tcaa                                             24

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
cagataactg ggccaaccat                                                  20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
attcacccct ttcccttgtc                                                  20

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
                                    primer

<400> SEQUENCE: 195
cgtagctcag gcctcaagac                                                 20

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
cgaacaggag gagcagagag                                                 20

<210> SEQ ID NO 197
<211> LENGTH: 23
<212> TYPE: DNA
<213> ORGANISM: Homo sapiens

<400> SEQUENCE: 197
caacagttcc cttctgatat cta                                             23

<210> SEQ ID NO 198
<211> LENGTH: 23
<212> TYPE: DNA
<213> ORGANISM: Homo sapiens

<400> SEQUENCE: 198
caacatttcc cttctgatat cta                                             23

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
gagggtgagg gtcaaccaac                                                 20

<210> SEQ ID NO 200
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
cttaaggcaa gaatcactgc ttagccaggg ccccaagggg gggaaaggca tgg            53

<210> SEQ ID NO 201
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
gagttaaaat cagaaatctc atctttcaca ggttatgatc aattagtcag                50
```

```
<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
cttagccagg tatgatcaat                                                    20

<210> SEQ ID NO 203
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
cttaaggcaa gaatcactgc ttagccaggt atgatcaatt agtcag                       46

<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
tacccctgtg acaggttatg                                                    20

<210> SEQ ID NO 205
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
acaggttatg atcaattagt cag                                                23

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
cttagccagg tatgatcaat                                                    20

<210> SEQ ID NO 207
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
cttaaggcaa gaatcactgc ttagccaggt atgatcaatt agtcag                       46

<210> SEQ ID NO 208
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
cactgcttag gttatgatca                                                   20

<210> SEQ ID NO 209
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
cttaaggcaa gaatcactgc ttaggttatg atcaattagt cag                         43

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
agaatcactg tcacaggtta                                                   20

<210> SEQ ID NO 211
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
cttaaggcaa gaatcactgt cacaggttat gatcaattag tcag                        44

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
gcttagccac gccaggttat                                                   20

<210> SEQ ID NO 213
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
cttaaggcaa gaatcactgc ttagccacgc caggttatga tcaattagtc ag               52

<210> SEQ ID NO 214
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
atcactgctt acaggttatg                                              20

<210> SEQ ID NO 215
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
cttaaggcaa gaatcactgc ttacaggtta tgatcaatta gtcag                  45
```

TARGETING BCL11A DISTAL REGULATORY ELEMENTS FOR FETAL HEMOGLOBIN REINDUCTION

CROSS REFERENCE TO RELATED APPLICATIONS

This application is a divisional application of U.S. Pat. No. 9,822,355 issued on Nov. 21, 2017, which is a 35 U.S.C. 371 National Stage Application of International Application No. PCT/US2013/072236 filed on Nov. 27, 2013, which designates the United States, and which claims the benefit under 35 U.S.C. § 119(e) of U.S. Provisional Application No. 61/730,323 filed Nov. 27, 2012, of U.S. Provisional Application No. 61/730,369 filed Nov. 27, 2012, of U.S. Provisional Application No. 61/776,144 filed Mar. 11, 2013, and of U.S. Provisional Application No. 61/889,174 filed Oct. 10, 2013, the contents of each of which are incorporated herein by reference in their entireties.

GOVERNMENT SUPPORT

This invention was made with government support under grant number HL032259 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Jun. 19, 2015, is named 701039-076205-US_SL.txt and is 49,435 bytes in size.

BACKGROUND

Normal adult hemoglobin comprises four globin proteins, two of which are alpha (α) proteins and two of which are beta (β) proteins. During mammalian fetal development, particularly in humans, the fetus produces fetal hemoglobin, which comprises two gamma (γ)-globin proteins instead of the two β-globin proteins. During the neonatal period, a globin switch occurs, referred to as the "fetal switch", at which point, erythroid precursors switch from making predominantly γ-globin to making predominantly β-globin. The developmental switch from production of predominantly fetal hemoglobin or HbF ($\alpha_2\gamma_2$) to production of adult hemoglobin or HbA ($\alpha_2\beta_2$) begins at about 28 to 34 weeks of gestation and continues shortly after birth until HbA becomes predominant. This switch results primarily from decreased transcription of the gamma-globin genes and increased transcription of beta-globin genes. On average, the blood of a normal adult contains less than 1% HbF, though residual HbF levels have a variance of over 20 fold in healthy adults and are genetically controlled.

Hemoglobinopathies encompass a number of anemias of genetic origin in which there is a decreased production and/or increased destruction (hemolysis) of red blood cells (RBCs). These also include genetic defects that result in the production of abnormal hemoglobins with a concomitant impaired ability to maintain oxygen concentration. Some such disorders involve the failure to produce normal β-globin in sufficient amounts, while others involve the failure to produce normal β-globin entirely. These disorders associated with the β-globin protein are referred to generally as β-hemoglobinopathies. For example, β-thalassemias result from a partial or complete defect in the expression of the β-globin gene, leading to deficient or absent HbA. Sickle cell anemia results from a point mutation in the β-globin structural gene, leading to the production of an abnormal (sickle) hemoglobin (HbS). HbS is prone to polymerization, particularly under deoxygenated conditions. HbS RBCs are more fragile than normal RBCs and undergo hemolysis more readily, leading eventually to anemia.

Recently, the search for treatment aimed at reduction of globin chain imbalance or predisposition to hemoglobin polymerization in patients with β-hemoglobinopathies has focused on the pharmacologic manipulation of fetal hemoglobin ($\alpha 2\gamma 2$; HbF). The therapeutic potential of such approaches is suggested by observations of the mild phenotype of individuals with co-inheritance of both homozygous β-thalassemia and hereditary persistence of fetal hemoglobin (HPFH), as well as by those patients with homozygous β-thalassemia who synthesize no adult hemoglobin, but in whom a reduced requirement for transfusions is observed in the presence of increased concentrations of fetal hemoglobin. Furthermore, it has been observed that certain populations of adult patients with β chain abnormalities have higher than normal levels of fetal hemoglobin (HbF), and have been observed to have a milder clinical course of disease than patients with normal adult levels of HbF. For example, a group of Saudi Arabian sickle-cell anemia patients who express 20-30% HbF have only mild clinical manifestations of the disease. It is now accepted that hemoglobin disorders, such as sickle cell anemia and the β-thalassemias, are ameliorated by increased HbF production.

As mentioned earlier, the switch from fetal hemoglobin to adult hemoglobin ($\alpha 2\gamma 2$; HbA) usually proceeds within six months after parturition. However, in the majority of patients with β-hemoglobinopathies, the upstream γ globin genes are intact and fully functional, so that if these genes become reactivated, functional hemoglobin synthesis could be maintained during adulthood, and thus ameliorate disease severity. Unfortunately, the in vivo molecular mechanisms underlying the globin switch are not well understood.

Evidence supporting the feasibility of reactivation of fetal hemoglobin production comes from experiments in which it was shown that peripheral blood, containing clonogenic cells, when given the appropriate combination of growth factors, produce erythroid colonies and bursts in semisolid culture. Individual cells in such colonies can accumulate fetal hemoglobin (HbF), adult hemoglobin (HbA) or a combination of both. In cultures from adult blood, nucleated red cells accumulate either HbA (F–A+) only, or a combination of HbF and HbA (F+A+). Importantly, individual colonies contain both F+ and F– cells, indicating that both types are progeny from the same circulating stem cells. Thus, during the early stages of development in culture, cells execute an option, through currently unknown mechanisms, whether or not to express HbF. The proportion of adult F+ cells developing in culture does not appear to be preprogrammed in vivo, but appears to depend on culture conditions: A shift into the combined HbF and HbA expression pathway can, for example, be achieved in vitro by high serum concentrations, due to the activity of an unidentified compound that can be absorbed on activated charcoal.

Overall, identification of molecules that play a role in the globin switch is important for the development of novel therapeutic strategies that interfere with adult hemoglobin and induce fetal hemoglobin synthesis. Such molecules would provide new targets for the development of therapeutic interventions for a variety of hemoglobinopathies in which reactivation of fetal hemoglobin synthesis would significantly ameliorate disease severity and morbidity.

SUMMARY

Provided herein are methods and compositions for increasing fetal β-globin levels in a cell by disrupting BCL11A expression at the genomic level. Also provided herein are methods and compositions relating to the treatment of hemoglobinopathies by reinduction of fetal β-globin levels.

One aspect described herein relates to a method for producing a progenitor cell having decreased BCL11A mRNA or protein expression, the method comprising contacting an isolated progenitor cell with an agent that binds the genomic DNA of the cell on chromosome 2 location 60,716,189-60,728,612 (according to UCSC Genome Browser hg 19 human genome assembly), thereby reducing the mRNA or protein expression of BCL11A.

Another aspect described herein relates to a method for producing a genetic engineered human cell having at least one genetic modification comprising contacting an isolated cell with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 causing at least one genetic modification therein.

Also provided herein in another aspect is an isolated genetic engineered human cell having at least one genetic modification on chromosome 2 location 60,716,189-60,728,612. In one embodiment, the at least one genetic modification is a deletion in the genomic DNA at the specified location. In one embodiment, the isolated genetic engineered human cell has reduced or decreased mRNA or protein expression of BCL11A compared to a control cell that has no one genetic modification on chromosome 2 location 60,716,189-60,728,612.

Another aspect described herein relates to a use of an isolated genetic engineered human cell having at least one genetic modification on chromosome 2 location 60,716,189-60,728,612 described herein for the purpose of increasing the fetal hemoglobin levels in a mammal.

Another aspect described herein relates to a use of an isolated genetic engineered human cell having at least one genetic modification on chromosome 2 location 60,716,189-60,728,612 described herein for the treatment a hemoglobinopathy in a mammal.

Another aspect described herein relates to a use of an isolated genetic engineered human cell having at least one genetic modification on chromosome 2 location 60,716,189-60,728,612 described herein for the manufacturer of medicament for the treatment a hemoglobinopathy in a mammal whereby the fetal hemoglobin levels in a mammal is increased.

Another aspect described herein is a composition comprising isolated genetic engineered human cells having at least one genetic modification on chromosome 2 location 60,716,189-60,728,612. In one embodiment, the composition further comprises a pharmaceutically acceptable carrier.

Another aspect described herein relates to a use of a composition comprising isolated genetic engineered human cells having at least one genetic modification on chromosome 2 location 60,716,189-60,728,612 for the purpose of increasing the fetal hemoglobin levels in a mammal.

Another aspect described herein relates to a use of a composition comprising isolated genetic engineered human cells having at least one genetic modification on chromosome 2 location 60,716,189-60,728,612 for the treatment a hemoglobinopathy in a mammal.

Another aspect described herein relates to a use of a composition comprising isolated genetic engineered human cells having at least one genetic modification on chromosome 2 location 60,716,189-60,728,612 for the manufacturer of medicament for the treatment a hemoglobinopathy in a mammal whereby the fetal hemoglobin levels in a mammal is increased.

Another aspect described herein is a composition comprising at least a DNA-targeting endonuclease or a vector carrying the coding sequence of a DNA-targeting endonuclease whereby the DNA-targeting endonuclease cleaves the genomic DNA of a human cell on chromosome 2 location 60,716,189-60,728,612 causing at least one genetic modification therein. In one embodiment, the composition further comprises a pharmaceutically acceptable carrier.

Another aspect described herein relates to a use of a composition comprising at least a DNA-targeting endonuclease or a vector carrying the coding sequence of a DNA-targeting endonuclease whereby the DNA-targeting endonuclease cleaves the genomic DNA of a human cell on chromosome 2 location 60,716,189-60,728,612 causing at least one genetic modification therein for the purpose of increasing the fetal hemoglobin levels in a mammal.

Another aspect described herein relates to a use of a composition comprising at least a DNA-targeting endonuclease or a vector carrying the coding sequence of a DNA-targeting endonuclease whereby the DNA-targeting endonuclease cleaves the genomic DNA of a human cell on chromosome 2 location 60,716,189-60,728,612 causing at least one genetic modification therein for the treatment a hemoglobinopathy in a mammal.

Another aspect described herein relates to a use of a composition comprising at least a DNA-targeting endonuclease or a vector carrying the coding sequence of a DNA-targeting endonuclease whereby the DNA-targeting endonuclease cleaves the genomic DNA of a human cell on chromosome 2 location 60,716,189-60,728,612 causing at least one genetic modification therein for the manufacturer of medicament for the treatment a hemoglobinopathy in a mammal whereby the fetal hemoglobin levels in a mammal is increased.

In one embodiment, provided herein is a use of an agent that binds the genomic DNA of the cell on chromosome 2 location 60,716,189-60,728,612 (according to UCSC Genome Browser hg 19 human genome assembly) for increasing the fetal hemoglobin in a mammal or for the treatment of a hemoglobinopathy in the mammal or for reducing the mRNA or expression of BCL11A, wherein the mRNA or protein expression of BCL11A is reduced.

In one embodiment, provided herein is a use of an effective amount of a composition comprising at least a DNA-targeting endonuclease or a vector carrying the coding sequence of a DNA-targeting endonuclease for increasing the fetal hemoglobin in a mammal or for the treatment of a hemoglobinopathy in the mammal or for reducing the mRNA or expression of BCL11A, wherein the DNA-targeting endonuclease cleaves the genomic DNA of the cell on chromosome 2 location 60,716,189-60,728,612 causing at least one genetic modification therein.

In one embodiment, provided herein is a use of an effective amount of a composition comprising at least a DNA-targeting enzyme or a vector carrying the coding sequence of a DNA-targeting enzyme for increasing the fetal hemoglobin in a mammal or for the treatment of a hemoglobinopathy in the mammal or for reducing the mRNA or expression of BCL11A, wherein the DNA-targeting enzyme produces at least one epigenetic modification in the genomic DNA of the cell on chromosome 2, thereby affecting the mRNA or expression of BCL11A. In one embodiment, the at least one epigenetic modification is at location 60,716,189-60,728,612. In another embodiment, the effect of the one epigenetic modification is reducing the mRNA or protein expression of BCL11A. In one embodiment, the at least one epigenetic modification in the genomic DNA of the cell on chromosome 2 indirectly or directly affects the location 60,716,189-60,728,612 of chromosome 2.

In one embodiment, provided herein is a use of any isolated cells described herein for increasing the fetal hemoglobin in a mammal or for the treatment of a hemoglobinopathy in the mammal.

In one embodiment, provided herein is a use of a composition comprising isolated genetic engineered human cells for increasing the fetal hemoglobin in a mammal or for the treatment of a hemoglobinopathy in the mammal, wherein the cells have at least one genetic modification on chromosome 2 location 60,716,189-60,728,612 (according to UCSC Genome Browser hg 19 human genome assembly) made by the process of contacting the cells with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 (according to UCSC Genome Browser hg 19 human genome assembly) causing at least one genetic modification therein.

In one embodiment, provided herein is a use of a composition comprising isolated genetic engineered human cells for increasing the fetal hemoglobin in a mammal or for the treatment of a hemoglobinopathy in the mammal, wherein the cells have at least one epigenetic modification on chromosome 2. In one embodiment, the at least one epigenetic modification on chromosome 2 is at location 60,716,189-60,728,612 (according to UCSC Genome Browser hg 19 human genome assembly). In another embodiment, at least one epigenetic modification on chromosome 2 is made by the process of contacting the cells with an effective amount of a composition comprising at least a DNA-targeting enzyme or a vector carrying the coding sequence of a DNA-targeting enzyme whereby the DNA-targeting enzyme produces at least one epigenetic modification in the genomic DNA of the cell on chromosome 2 which affects the location 60,716,189-60,728,612 (according to UCSC Genome Browser hg 19 human genome assembly) causing therein.

In one embodiment, provided herein is a use of any isolated cells described herein or any one of the compositions described herein for the manufacture of a medicament for increasing the fetal hemoglobin in a mammal in need thereof or for the treatment of a hemoglobinopathy in a mammal.

Another aspect described herein is a method of increasing fetal hemoglobin levels in a cell, the method comprising the steps of: contacting an isolated cell with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 causing at least one genetic modification therein, whereby fetal hemoglobin expression is increased in said cell, or its progeny, relative to the cell prior to the contacting.

Another aspect described herein is a method for increasing fetal hemoglobin levels in a mammal in need thereof, the method comprising the steps of contacting an isolated hematopoietic progenitor cell in said mammal with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 causing at least one genetic modification therein, whereby fetal hemoglobin expression is increased in said mammal, relative to expression prior to said contacting.

Another aspect described herein is a method for increasing fetal hemoglobin levels in a mammal in need thereof, the method comprising transplanting an isolated genetic engineered human cell having at least one genetic modification on chromosome 2 location 60,716,189-60,728,612 into the mammal.

In one embodiment, this disclosure provides a method for increasing fetal hemoglobin levels in a mammal in need thereof, the method comprising the steps of providing an isolated population of hematopoietic progenitor cells or hematopoietic stem cells from the mammal in ex vivo, and contacting the population of hematopoietic progenitor or stem cells with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 causing at least one genetic modification therein, whereby fetal hemoglobin expression is increased in the mammal, relative to expression prior to the contacting.

In one embodiment, this disclosure provides a method for increasing fetal hemoglobin levels in a mammal in need thereof, the method comprising the steps of isolating a population of hematopoietic progenitor cells or hematopoietic stem cells from the mammal, and contacting in ex vivo the population of hematopoietic progenitor or stem cells with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 causing at least one genetic modification therein, whereby fetal hemoglobin expression is increased in the mammal, relative to expression prior to the contacting.

In one embodiment, this disclosure provides a method for increasing fetal hemoglobin levels in a mammal in need thereof, the method comprising the steps of providing isolating a population of hematopoietic progenitor cells or hematopoietic stem cells from the mammal and deleting the genomic DNA of the cells on chromosome 2 location 60,716,189-60,728,612 causing at least one genetic modification therein, whereby fetal hemoglobin expression is increased in the mammal, relative to expression prior to the contacting.

In one embodiment, this disclosure provides a method for increasing fetal hemoglobin levels in a mammal in need thereof, the method comprising the steps of isolating a population of hematopoietic progenitor cells or hematopoietic stem cells from the mammal and ex vivo deleting the genomic DNA of the cells on chromosome 2 location 60,716,189-60,728,612 causing at least one genetic modification therein, whereby fetal hemoglobin expression is increased in the mammal, relative to expression prior to the contacting.

In one embodiment, this disclosure provides a method of treatment of a hemoglobinopathy in a mammal comprising the steps of (a) providing hematopoietic progenitor cells or hematopoietic stem cells or iPSCs; (b) contacting the cells ex vivo or in vitro with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 causing at least one genetic modification therein, whereby fetal hemoglobin expression is increased in the mammal, relative to expression prior to the contacting; and (c) administering the cells of step (b) into the mammal.

In one embodiment, this disclosure provides a method of treatment of a hemoglobinopathy in a mammal comprising the steps of (a) isolating hematopoietic progenitor cells or hematopoietic stem cells from the mammal; (b) contacting the cells ex vivo or in vitro with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 causing at least one genetic modification therein, whereby fetal hemoglobin expression is increased in the mammal, relative to expression prior to the contacting; and (c) administering the cells of step (b) into the mammal.

In one embodiment, this disclosure provides a method of treatment of a hemoglobinopathya in a mammal comprising the steps of: (a) providing hematopoietic progenitor cells or hematopoietic stem cells or iPSCs; (b) ex vivo deleting the genomic DNA of the cells on chromosome 2 location 60,716,189-60,728,612 causing at least one genetic modification therein, whereby fetal hemoglobin expression is increased in the mammal, relative to expression prior to the contacting; and (c) administering the cells of step (b) into the mammal.

In one embodiment, this disclosure provides a method of treatment of a hemoglobinopathy in a mammal comprising the steps of (a) isolating hematopoietic progenitor cells or hematopoietic stem cells from the mammal; (b) ex vivo deleting the genomic DNA of the cells on chromosome 2 location 60,716,189-60,728,612 causing at least one genetic modification therein, whereby fetal hemoglobin expression is increased in the mammal, relative to expression prior to the contacting; and (c) administering the cells of step (b) into the mammal.

In one embodiment, this disclosure provides a method of treatment of a hemoglobinopathy in a mammal (e.g. a human) comprising introducing a composition described herein comprising isolated genetic engineered cells having at least one genetic modification on chromosome 2 location 60,716,189-60,728,612 whereby fetal hemoglobin expression is increased in the mammal.

In one embodiment, this disclosure provides a method of treatment of a hemoglobinopathy in a mammal (e.g. a human) comprising increasing fetal hemoglobin expression in the mammal by method described herein.

In one embodiment of this aspect and all other aspects described herein, the isolated cell or isolated population of cells is/are human cell(s).

In one embodiment of this aspect and all other aspects described herein, the isolated cell or isolated population of cells is/are progenitor cell(s).

In one embodiment of this aspect and all other aspects described herein, the human cell is a hematopoietic progenitor cell.

In one embodiment of this aspect and all other aspects described herein, the human cell is an induced pluripotent stem cell.

In one embodiment of this aspect and all other aspects described herein, the induced pluripotent stem cell is hematopoietic progenitor cell.

In one embodiment of this aspect and all other aspects described herein, the hematopoietic progenitor is a cell of the erythroid lineage.

In one embodiment of this aspect and all other aspects described herein, the hematopoietic progenitor cell or isolated is contacted ex vivo or in vitro or in vivo.

In one embodiment of this aspect and all other aspects described herein, the at least one genetic modification is a deletion.

In one embodiment of this aspect and all other aspects described herein, the deletion removes the entire region between chromosome 2 location 60,716,189-60,728,612 or removes a portion of the region resulting in disruption of one or more DNAse 1-hypersensitive sites (DHS).

In another embodiment of this aspect and all other aspects described herein, the deletion comprises one or more of the DNAse 1-hypersensitive sites (DHS) +62, +58, and +55 as described herein in the Examples section.

In another embodiment of this aspect and all other aspects described herein, the deletion comprises one or more of the SNP markers described in Table 2.

In another embodiment of this aspect and all other aspects described herein, the deletion comprises one or more of the fragments listed in Table 7.

In another embodiment of this aspect and all other aspects described herein, the deletion removes the entire region between chromosome 2 location 60,716,189-60,728,612 or removes a portion of the region resulting in disruption of one or more DNAse 1-hypersensitive sites (DHS). In one embodiment, as used herein, the term "portion" in the context of genomic deletion is at least 20%-80% of the specified region.

In further embodiment of any treatment method, the method comprises chemotherapy and/or radiation therapy to remove or reduced the endogenous hematopoietic progenitor or stem cells in the mammal.

In one embodiment of any method, the contacted cells having at least one genetic modification can be cryopreserved and stored until the cells are needed for administration into a mammal.

In one embodiment of any described method, the hematopoietic progenitor or stem cells or isolated cells can be substituted with an iPSCs described herein.

In one embodiment of any described method, the hematopoietic progenitor or stem cells or iPSCs or isolated cells are autologous to the mammal, meaning the cells are derived from the same mammal. In another of the embodiments of the described method, the hematopoietic progenitor or stem cells or iPSCs or isolated cells are non-autologous to the mammal, meaning the cells are not derived from the same mammal, but another mammal of the same species. For example, the mammal is a human.

In one embodiment of any treatment method, the method further comprises selecting a mammal in need of increased fetal hemoglobin expression.

In one embodiment of any treatment method, the method further comprises selecting a mammal in need of treatment of a hemoglobinopathy.

In any embodiment of any treatment method described, the hemoglobinopathy is a β-hemoglobinopathy.

In any embodiment of any treatment method described, the hemoglobinopathy is β-thalassemia.

In any embodiment of any treatment method described, the hemoglobinopathy is sickle cell anemia.

BRIEF DESCRIPTION OF DRAWINGS

FIGS. 4A-4C show data from a 12.4-kb fragment of BCL11A intron-2 encompassing the DHSs +62, +58 and +55 (encompassing +52.0-64.4 kb from TSS) cloned upstream of an Hsp68 minimal promoter and lacZ reporter gene flanked by H19 insulator elements. Transient transgenic murine embryos generated by nuclear injection at the one-cell stage.

FIG. 4A shows E12.5 transient transgenic embryo stained with X-gal.

FIG. 4B shows cell suspensions isolated from the peripheral blood and fetal liver of stable transgenic E12.5 embryos. Cytospins were stained with X-gal and counterstained with Nuclear Red.

FIG. 4C shows data from bone marrow erythroblasts (CD71+/Ter119+) and splenic lymphocytes (CD19+ for B-lymphocytes and CD3+ for T-lymphocytes) that were isolated and sorted from young adult stable transgenics. Cells were subject to X-gal staining or RNA isolation followed by RT-qPCR. Gene expression normalized to GAPDH, and expressed relative to T-lymphocytes, which express neither BCL11A nor lacZ.

FIG. 5A shows RT-qPCR performed of Bcl11a with primer pairs recognizing sequences upstream, spanning, and downstream of intron-2.

FIG. 5B shows an immunoblot of Δ50.4-60.4 with anti-BCL11A.

FIG. 5C shows globin gene expression in Δ50.4-60.4 MEL clones. A common primer pair recognizes the adult β-globins β2 and β1, while independent primers recognize the embryonic β-globins εy and βH1.

DETAILED DESCRIPTION

Figure 1A:
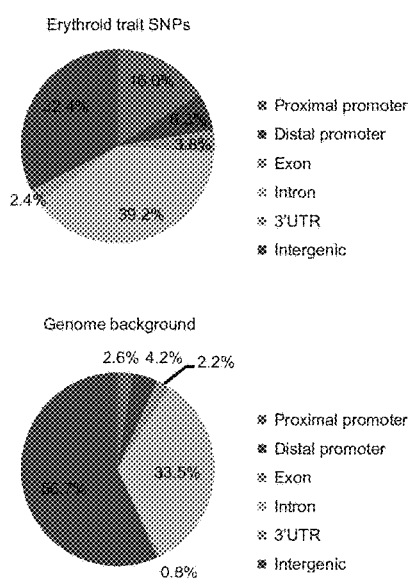
FIG. 1A shows the distribution of 636 SNPs previously published to be associated with erythroid traits at $P<5\times10^{-8}$ with respect to promoter, exonic, intronic, 3'UTR, and intergenic sequences. For comparison, genomic distribution of these regions is displayed.

The methods and compositions described herein relate, in part, to the discovery of a distal regulatory region upstream of the BCL11A gene that can regulate expression of the BCL11A protein. The BCL11A protein acts as a stage specific regulator of fetal hemoglobin expression by repressing γ-globin induction. Accordingly, the methods and compositions provided herein are novel methods for the regulation of γ-globin expression in eythroid cells. More specifically, these activities can be harnessed in methods for the treatment of β-hemoglobinopathies by induction of γ-globin via inhibition of the BCL11A gene product.

In one embodiment, provided herein is a method for producing an isolated progenitor cell having decreased BCL11A mRNA or protein expression, the method comprising contacting an isolated progenitor cell with an agent that binds the genomic DNA of the cell on chromosome 2 location 60,716,189-60,728,612 (according to UCSC Genome Browser hg 19 human genome assembly), thereby reducing the mRNA or protein expression of BCL11A.

In one embodiment, provided herein is a method for producing an isolated progenitor cell having decreased BCL11A mRNA or protein expression, the method comprising providing an isolated progenitor cell and contacting the isolated progenitor cell with an agent that binds the genomic DNA of the cell on chromosome 2 location 60,716,189-60,728,612 (according to UCSC Genome Browser hg 19 human genome assembly), thereby reducing the mRNA or protein expression of BCL11A.

In one embodiment, provided herein is a method for producing an isolated progenitor cell having decreased BCL11A mRNA or protein expression, the method comprising contacting an isolated progenitor cell with an agent that produces an epigenetic modification in the genomic DNA of the cell on chromosome 2 thereby reducing the mRNA or protein expression of BCL11A. In one embodiment, the epigenetic modification in the genomic DNA is at chromosome 2location 60,716,189-60,728,612 (according to UCSC Genome Browser hg 19 human genome assembly).

In one embodiment, provided herein is a method for producing an isolated progenitor cell having decreased BCL11A mRNA or protein expression, the method comprising providing an isolated progenitor cell and contacting the isolated progenitor cell with an agent that produces an epigenetic modification in the genomic DNA of the cell on chromosome 2 thereby reducing the mRNA or protein expression of BCL11A. In one embodiment, the epigenetic modification in the genomic DNA is at chromosome 2location 60,716,189-60,728,612 (according to UCSC Genome Browser hg 19 human genome assembly).

The disclosure described herein, in a preferred embodiment, does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

One aspect described herein relates to a method for producing an isolated genetic engineered human cell having at least one genetic modification comprising contacting the cell with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 (according to UCSC Genome Browser hg 19 human genome assembly) causing at least one genetic modification therein.

Another aspect provided herein relates to a method of increasing fetal hemoglobin levels in an isolated cell, the method comprising decreasing the BCL11A mRNA or protein expression in the cell. In one aspect, the decrease of BCL11A mRNA or protein expression is achieved by causing at least one genetic modification at the genomic DNA of the cell on chromosome 2 location 60,716,189-60,728,612 (according to UCSC Genome Browser hg 19 human genome assembly). In another aspect, the decrease of BCL11A mRNA or protein expression is achieved by causing at least one genetic modification at the genomic DNA of the cell on chromosome 2 location 60,716,189-60,728,612 that results in epigenetic modification of the genetic function at chromosome 2 location 60,716,189-60,728,612. In this aspect, the BCL11A enhancer activity located within this chromosome 2 location 60,716,189-60,728,612 is reduce. By decrease in this aspect, the enhancer activity in enhancing BCL11A mRNA or protein expression in the cell is at least 5% lower is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more compared to a control cell that is not treated in any method disclosed herein. By decrease of the BCL11A mRNA or protein expression in the cell means that protein expression is at least 5% lower is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more compared to a control cell that is not treated in any method disclosed herein.

Another aspect provided herein relates to a method of increasing fetal hemoglobin levels in an isolated cell, the method comprising providing an isolated human cell or progenitor cell and decreasing the BCL11A mRNA or protein expression in the cell.

Another aspect provided herein relates to a method of increasing fetal hemoglobin levels in a cell, the method comprising the steps of: contacting an isolated human cell with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 (according to UCSC Genome Browser hg 19 human genome assembly) causing at least one genetic modification therein, whereby fetal hemoglobin expression is increased in the cell, or its progeny, relative to the cell prior to the contacting.

Another aspect provided herein relates to a method of increasing fetal hemoglobin levels in a cell, the method comprising the steps of providing an isolated human cell or progenitor cell, contacting an isolated human cell or progenitor cell with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 (according to UCSC Genome Browser hg 19 human genome assembly) causing at least one genetic modification therein, whereby fetal hemoglobin expression is increased in the cell, or its progeny, relative to the cell prior to the contacting.

Another aspect described herein relates to a method for increasing fetal hemoglobin levels in a mammal in need thereof, the method comprising decreasing the BCL11A mRNA or protein expression in a hematopoietic progenitor cell in the mammal. In one aspect, the decrease of BCL11A mRNA or protein expression is achieved by causing at least one genetic modification at the genomic DNA of the cell on chromosome 2 location 60,716,189-60,728,612 (according to UCSC Genome Browser hg 19 human genome assembly). In another aspect, the decrease of BCL11A mRNA or protein expression is achieved by causing at least one epigenetic modification at the genomic DNA of the cell on chromosome 2. In another aspect, the decrease of BCL11A mRNA or protein expression is achieved by causing at least one epigenetic modification at the genomic DNA of the cell on chromosome 2 location 60,716,189-60,728,612.

Another aspect described herein relates to a method for increasing fetal hemoglobin levels in a mammal in need thereof, the method comprising providing an isolated human cell or progenitor cell from a mammal and decreasing the BCL11A mRNA or protein expression in the cell. In one aspect, the method further comprises selecting a mammal in need of increasing fetal hemoglobin levels therein.

Another aspect described herein relates to a method for increasing fetal hemoglobin levels in a mammal in need thereof, the method comprising the steps of contacting a hematopoietic progenitor cell in the mammal with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 (according to UCSC Genome Browser hg 19 human genome assembly) causing at least one genetic modification therein, whereby fetal hemoglobin expression is increased in the mammal, relative to expression prior to the contacting.

Another aspect described herein relates to a method for increasing fetal hemoglobin levels in a mammal in need thereof, the method comprising the steps of providing an isolated human cell or progenitor cell or an isolated population of hematopoietic progenitor cells from a mammal contacting the human cell or progenitor cell or hematopoietic progenitor cell with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 (according to UCSC Genome Browser hg 19 human genome assembly) causing at least one genetic modification therein, whereby fetal hemoglobin expression is increased in said mammal, relative to expression prior to the contacting.

Another aspect provided herein relates to a method for increasing fetal hemoglobin levels in a mammal in need thereof, the method comprising transplanting a genetic engineered human cell as described herein into the mammal.

In one embodiment of this aspect and all other aspects described herein, the method further comprises providing an isolated cell or an isolated progenitor cell or an isolated population of cells which can be progenitor cell or hematopoietic progenitor cell.

In one embodiment of this aspect and all other aspects described herein, the isolated cell is an isolated progenitor cell.

In one embodiment of this aspect and all other aspects described herein, the isolated progenitor cell is an isolated human cell.

In one embodiment of this aspect and all other aspects described herein, the isolated human cell is a hematopoietic progenitor cell.

In another embodiment of this aspect and all other aspects described herein, the hematopoietic cell is a cell of the erythroid lineage. Methods of isolating hematopoietic progenitor cell are well known in the art, e.g., by flow cytometric purification of CD34+ or CD133+ cells, microbeads conjugated with antibodies against CD34 or CD133, markers of hematopoietic progenitor cell. Commercial kits are also available, e.g., MACS® Technology CD34 MicroBead Kit, human, and CD34 MultiSort Kit, human, and STEMCELL™ Technology EasySep™ Mouse Hematopoietic Progenitor Cell Enrichment Kit.

In another embodiment of this aspect and all other aspects described herein, the human cell is an induced pluripotent stem cell (iPSC).

In another embodiment of this aspect and all other aspects described herein, the contacting of any cell described herein can be ex vivo or in vitro or in vivo.

In another embodiment of this aspect and all other aspects described herein, the contacting of any cell described herein comprises contacting with an agent that binds the genomic DNA of the cell on chromosome 2 and produces an epigenetic modification in the genome of the cell on chromosome 2, thereby reducing the mRNA or protein expression of BCL11A. In one embodiment, the epigenetic modification is on chromosome 2 location 60,716,189-60,728,612 (according to UCSC Genome Browser hg 19 human genome assembly).

In one embodiment of this aspect and all other aspects described herein, the at least one epigenetic modification in the genomic DNA of the cell on chromosome 2 indirectly or directly affects the location 60,716,189-60,728,612 of chromosome 2.

As used herein, "indirectly affecting the location 60,716, 189-60,728,612 of chromosome 2" refers to long distance effects of epigenetic modification in the genomic DNA of the cell on chromosome 2 the location 60,716,189-60,728,612 of chromosome 2.

In another embodiment of this aspect and all other aspects described herein, the contacting of any cell described herein comprises contact with an agent that binds the genomic DNA of the cell on chromosome 2 location 60,716,189-60, 728,612 (according to UCSC Genome Browser hg 19 human genome assembly), and produces an epigenetic modification on chromosome 2, thereby reducing the mRNA or protein expression of BCL11A.

In another embodiment of this aspect and all other aspects described herein, the contacting of any cell described herein comprises contact with an effective amount of a composition comprising at least a DNA-targeting enzyme or a vector carrying the coding sequence of a DNA-targeting enzyme whereby the DNA-targeting enzyme produces an epigenetic modification on chromosome 2, thereby reducing the mRNA or protein expression of BCL11A.

In another embodiment of this aspect and all other aspects described herein, the contacting of any cell described herein comprises contact with an effective amount of a composition comprising at least a DNA-targeting enzyme or a vector carrying the coding sequence of a DNA-targeting enzyme whereby the DNA-targeting enzyme produces an epigenetic modification on chromosome 2 location 60,716,189-60,728, 612 (according to UCSC Genome Browser hg 19 human genome assembly) thereby reducing the mRNA or protein expression of BCL11A. In one aspect, fetal hemoglobin expression is increased in the mammal, relative to expression prior to the contacting.

In another embodiment of this aspect and all other aspects described herein, the hematopoietic progenitor cell, the isolated human cell, or isolated cell is contacted ex vivo or in vitro.

In another embodiment of this aspect and all other aspects described herein, the at least one genetic modification is a deletion.

In another embodiment of this aspect and all other aspects described herein, the deletion comprises one or more of the DNAse 1-hypersensitive sites (DHS) +62, +58, and +55 as described herein in the Examples section. In another embodiment of this aspect and all other aspects described herein, the deletion consists essentially of one or more of the DNAse 1-hypersensitive sites (DHS) +62, +58, and +55 as described herein in the Examples section. In another embodiment, the deletion consists of one or more of the DNAse 1-hypersensitive sites (DHS) +62, +58, and +55 as described herein in the Examples section.

In another embodiment of this aspect and all other aspects described herein, the epigenetic modification comprises or affects one or more of the DNAse 1-hypersensitive sites (DHS) +62, +58, and +55 as described herein in the Examples section. As used herein, the phrase "affects one or more of the DNAse 1-hypersensitive sites" means natural function of these DNAse 1-hypersensitive sites (DHS) +62, +58, and +55 are reduce, for example, access to transcription factors or DNA degradation enzymes such as DNase I. In general, DNase I hypersensitive sites (DHSs) are regions of chromatin which are sensitive to cleavage by the DNase I enzyme. In these specific regions of the genome, chromatin has lost its condensed structure, exposing the DNA, and making it accessible. This raises the availability of DNA to degradation by enzymes, like DNase I. These accessible chromatin zones are functionally related to transcriptional activity, since this remodeled state is necessary for the binding of proteins such as transcription factors. Accordingly, the epigenetic modification contemplated herein results in reduced access to DNA degradation enzymes that is at least 5% lower is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more compared to a control cell that is not treated in any method disclosed herein.

In another embodiment of this aspect and all other aspects described herein, the deletion comprises one or more of the SNP markers described in Table 2. In another embodiment of this aspect and all other aspects described herein, the deletion consists essentially of one or more of the SNP markers described in Table 2. In another embodiment of this aspect and all other aspects described herein, the deletion consists of one or more of the SNP markers described in Table 2.

In another embodiment of this aspect and all other aspects described herein, the epigenetic modification comprises or affects one or more of the SNP markers described in Table 2. As used herein, the phrase "affects one or more of the SNP markers" means natural function(s) of these SNPs are reduce, for example, access to transcription factors. For example, methylation of these SNPs would reduce the binding of transcription factors, leading to reduced mRNA or protein expression of BCL11A.

In another embodiment of this aspect and all other aspects described herein, the deletion comprises one or more of the fragments listed in Table 7. In another embodiment of this aspect and all other aspects described herein, the deletion consists essentially of one or more of the fragments listed in Table 7. In another embodiment of this aspect and all other aspects described herein, the deletion consists of one or more of the fragments listed in Table 7. In another embodiment of this aspect and all other aspects described herein, the deletion is from 60,716,189 to 60,728,612, from 60,716,189 to 60,723,870, from 60,722,992 to 60,728,612, from 60,717, 236 to 60,719,036, from 60,722,006 to 60,723,058, from 60,724,917 to 60,726,282, from 60,616,396 to 60,618,032, from 60,623,536 to 60,624,989, from 60,626,565 to 60,628, 177, from 60,717,236 to 60,719,036, from 60,721,212 to 60,722,958, from 60,724,780 to 60,726,471, from 60,739, 075 to 60,740,154, from 60,748,003 to 60,749,009, from 60,826,438 to 60,827,601, or from 60,831,589 to 60,833,556.

In another embodiment of this aspect and all other aspects described herein, the epigenetic modification comprises or affects one or more of the fragments listed in Table 7. As used herein, the phrase "affects one or more of the fragments listed in Table 7" means natural function(s) of these fragments are reduce, for example, access to transcription factors. For example, methylation of these fragments would reduce the binding of transcription factors, leading to reduced mRNA or protein expression of BCL11A.

In another embodiment of this aspect and all other aspects described herein, the epigenetic modification is from 60,716,189 to 60,728,612, from 60,716,189 to 60,723,870, from 60,722,992 to 60,728,612, from 60,717,236 to 60,719,036, from 60,722,006 to 60,723,058, from 60,724,917 to 60,726,282, from 60,616,396 to 60,618,032, from 60,623,536 to 60,624,989, from 60,626,565 to 60,628,177, from 60,717,236 to 60,719,036, from 60,721,212 to 60,722,958, from 60,724,780 to 60,726,471, from 60,739,075 to 60,740,154, from 60,748,003 to 60,749,009, from 60,826,438 to 60,827,601, or from 60,831,589 to 60,833,556.

In another embodiment of this aspect and all other aspects described herein, the deletion removes the entire region between chromosome 2 location 60,716,189-60,728,612 or removes a portion of the region resulting in disruption of one or more DNAse 1-hypersensitive sites (DHS). As used herein, the term "disruption" refers to a decrease in erythroid transcription of BCL11A in a cell comprising a disruption of one or more DNAse -1 hypersensitive sites by at least 10% (e.g., at least 20%, at least 30%, at least 40%, at least 50%, at least 60%, at least 70%, at least 80%, at least 90%, at least 95%, at least 99% or even 100% (i.e., no detectable erythroid transcription)) compared to a cell not having such a disruption. In one embodiment, the disruption comprises an inability of a modified DNAse-1hypersensitive site to bind to its native transcription factors (e.g., GATA1 and TAL1).

In another embodiment of this aspect and all other aspects described herein, the epigenetic modification that interferes with the establishment and/or maintenance of the epigenetic signature at the enhancer region on chromosome 2 location 60,716,189-60,728,612 (according to UCSC Genome Browser hg 19 human genome assembly) thereby leading to reduced mRNA or protein expression of BCL11A, and increasing fetal hemoglobin expression in the mammal.

In one embodiment of this aspect and all other aspects described herein, the epigenetic modification that interferes with the establishment and/or maintenance of the epigenetic signature at the enhancer region on chromosome 2 location 60,716,189-60,728,612 (according to UCSC Genome Browser hg 19 human genome assembly) includes but is not limited to epigenetic modifications that affects DNase I sensitivity, epigenetic modifications that affects histone modifications, epigenetic modifications that affects GATA1/TAL1 binding, and epigenetic modifications that affects long-range promoter interaction of the promoter of BCL11A.

For example, an epigenetic modification that interferes with the establishment and/or maintenance of the epigenetic signature at the enhancer region on chromosome 2 location 60,716,189-60,728,612 include but is not limited to at least one deletion within chromosome 2 location 60,716,189-60,728,612 such that the overall function of this region is affected whereby the mRNA and expression of BCL11A is reduced or decreased. For example, the deletion is at the DNaseI sensitivity regions chromosome 2 location 60,716,189-60,728,612, e.g., +62, +58, and +55. The deletion could be at +62 or +58 or +55 or combination thereof. For examples, at +62 and +58, +58 and +55, +62 and +55, or at all three +62, +58, and +55.

As another example, an epigenetic modification that interferes with the establishment and/or maintenance of the epigenetic signature at the enhancer region on chromosome 2 location 60,716,189-60,728,612 include but is not limited to changes in the histone modifications on chromosome 2 that is not at location 60,716,189-60,728,612, or changes in the histone modifications on chromosome 2 at location 60,716,189-60,728,612, or both histone modifications on chromosome 2 not at location 60,716,189-60,728,612 as well as at location 60,716,189-60,728,612 such that the overall function of this region is affected whereby the mRNA and expression of BCL11A is reduced or decreased.

In another embodiment, an epigenetic modification that interferes with the establishment and/or maintenance of the epigenetic signature at the enhancer region on chromosome 2 location 60,716,189-60,728,612 include but is not limited to an insertion of at least one engineered specific-repressor sequence that change the epigenetic features of noncoding elements at chromosome 2 location 60,716,189-60,728,612 and thus result in repression of target gene expression. The first is specifically focused on epigenetically repressing individual enhancers. In other words, insertion of engineered specific-repressor sequences into chromosome 2 would prospectively interfering with epigenetic modification at the BCL11A erythroid enhancer which eventually leads to reduced BCL11A gene expression.

Any methods known in the art can be used to produce the epigenetic modification contemplated. For example, as described in Mendenhall E. M. et al., Nat. Biotechnol. 08 Sep. 2013, and Maeder M L et al., Nat Biotechnol. 09 Oct. 2013 2013.

In one embodiment of this aspect and all other aspects described herein, the insertion of at least one engineered specific-repressor sequence on any location chromosome 2 results in but is not limited to reduced DNaseI sensitivity regions at chromosome 2 location 60,716,189-60,728,612, e.g., +62, +58, and +55; increased histone modifications on chromosome 2 location 60,716,189-60,728,612; reduced transcription factors binding to the GATA1/TAL1 of the enhancer region on chromosome 2 location 60,716,189-60,728,612; and reduced or weakened interaction between the chromosome 2 location 60,716,189-60,728,612 with the BCL11A promoter.

In one embodiment of this aspect and all other aspects described herein, the overall effects of the insertion of at least one engineered specific-repressor sequence on any location chromosome 2 is reduced or decreased mRNA and expression of BCL11A.

In some embodiments, as used in the context of mRNA and expression of BCL11A, interaction between the chromosome 2 location 60,716,189-60,728,612 or BCL11A enhancer with the BCL11A promoter, and transcription factors binding to the GATA1/TAL1 of the enhancer region, the term "reduced" or "decreased" refers to at least 5% lower is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more compared to the control situation that is in the absence of the epigenetic modification or insertion of engineered sequences disclosed herein. By decrease of the BCL11A mRNA or protein expression in the cell means that protein expression is at least 5% lower is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more compared to a control cell that does not have the epigenetic modification or insertion of engineered sequences disclosed herein.

In one embodiment of this aspect and all other aspects described herein, the insertion of at least one engineered specific-repressor sequence occurs within the DNaseI sensitivity regions of chromosome 2 location 60,716,189-60,728,612, e.g., +62, +58, and +55. The insertion could be at the 5'end of +62 or +58 or +55 or at the 3' end of +62 or +58 or +55, or between +62 and +58, or between +58 and +55, or between +55 and +62.

In one embodiment of this aspect and all other aspects described herein, the insertion of at least one engineered specific-repressor sequence changes the DNaseI sensitivity regions of chromosome 2 location 60,716,189-60,728,612.

In one embodiment of this aspect and all other aspects described herein, the epigenetic modifications changes the DNaseI sensitivity regions of chromosome 2 location 60,716,189-60,728,612.

In one embodiment of this aspect and all other aspects described herein, the epigenetic modifications changes the histone modifications on chromosome 2 location 60,716,189-60,728,612.

In one embodiment of this aspect and all other aspects described herein, the insertion of at least one engineered specific-repressor sequence changes the histone modifications on chromosome 2 location 60,716,189-60,728,612.

In one embodiment of this aspect and all other aspects described herein, the epigenetic modifications changes the GATA1/TAL1 binding of the enhancer region on chromosome 2 location 60,716,189-60,728,612 such that the overall function of this region is affected whereby the mRNA and expression of BCL11A is reduced or decreased. For example, the binding of transcription factors to the GATA1/TAL1.

In one embodiment of this aspect and all other aspects described herein, the insertion of at least one engineered specific-repressor sequence occurs within the GATA1/TAL1 as described herein. The insertion can be at the 5' end or 3'end of GATA1/TAL1. The insertion can be between GATA1 and TAL1. The insertion changes the GATA1/TAL1 binding of the enhancer region on chromosome 2 location 60,716,189-60,728,612 such that the overall function of this region is affected whereby the mRNA and expression of BCL11A is reduced or decreased. For example, the binding of transcription factors to the GATA1/TAL1.

In one embodiment of this aspect and all other aspects described herein, the epigenetic modification changes the interaction between the BCL11A enhancer and the BCL11A promoter. In one embodiment, the interaction is reduced or weakened such that the overall function of this region is affected whereby the mRNA and expression of BCL11A is reduced or decreased.

In one embodiment of this aspect and all other aspects described herein, the epigenetic modifications changes the interaction between the chromosome 2 location 60,716,189-60,728,612 with the BCL11A promoter. In one embodiment, the interaction is reduced or weakened such that the overall function of this region is affected whereby the mRNA and expression of BCL11A is reduced or decreased.

Also provided herein in another aspect is an isolated genetic engineered human cell having at least one genetic modification on chromosome 2 location 60,716,189-60,728,612 (according to UCSC Genome Browser hg 19 human genome assembly) made by the process of contacting the cell with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 causing at least one genetic modification therein.

In one embodiment of this aspect and all other aspects described herein, the isolated genetic engineered human cell having at least one epigenetic modification at the genomic DNA of the cell on chromosome 2. In another of this aspect and all other aspects described herein, the isolated genetic engineered human cell having at least one epigenetic modification at the genomic DNA of the cell on chromosome 2 location 60,716,189-60,728,612.

In some aspects of any of these isolated genetic engineered human cells having at least one epigenetic modification, the cells are transplanted into a mammal for use in increasing the fetal hemoglobin in the mammal.

In one embodiment of this aspect and all other aspects described herein, the isolated genetic engineered human cell having at least one genetic modification at the genomic DNA of the cell on chromosome 2 location 60,716,189-60,728,612 is transplanted into a mammal for use in increasing the fetal hemoglobin in the mammal.

In one embodiment of this aspect and all other aspects described herein, the isolated genetic engineered human cell having at least one genetic modification at the genomic DNA of the cell on chromosome 2 location 60,716,189-60,728,612 is stored for later use by cryopreservation.

In some aspects of any of those isolated genetic engineered human cells having at least one epigenetic modification, the cells are stored for later use by cryopreservation.

In one embodiment of this aspect and all other aspects described herein, the isolated genetic engineered human cell having at least one genetic modification at the genomic DNA of the cell on chromosome 2 location 60,716,189-60,728,612 is cryopreserved, thawed and transplanted into mammal for use in increasing the fetal hemoglobin in the mammal.

In some aspects of any of those isolated genetic engineered human cells having at least one epigenetic modification, cryopreserved, thawed and transplanted into mammal for use in increasing the fetal hemoglobin in the mammal.

Another aspect provided herein relates to a composition comprising isolated genetic engineered human cells, wherein the cells have at least one genetic modification on chromosome 2 location 60,716,189-60,728,612 (according to UCSC Genome Browser hg 19 human genome assembly) made by the process of contacting the cells with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 (according to UCSC Genome Browser hg 19 human genome assembly) causing at least one genetic modification therein.

Another aspect provided herein relates to a composition comprising isolated genetic engineered human cells, wherein the cells have at least one epigenetic modification on chromosome 2. In one embodiment, the at least one epigenetic modification on chromosome 2 is at location 60,716,189-60,728,612 (according to UCSC Genome Browser hg 19 human genome assembly). In another embodiment, at least one epigenetic modification on chromosome 2 is made by the process of contacting the cells with an effective amount of a composition comprising at least a DNA-targeting enzyme or a vector carrying the coding sequence of a DNA-targeting enzyme whereby the DNA-targeting enzyme produces at least one epigenetic modification in the genomic DNA of the cell on chromosome 2 which affects the location 60,716,189-60,728,612 (according to UCSC Genome Browser hg 19 human genome assembly) causing therein.

In one embodiment of this aspect and all other aspects described herein, the composition causes an increase in fetal hemoglobin mRNA or protein expression in the contact cell.

In one embodiment of this aspect and all other aspects described herein, the cells of any compositions described are autologous, to the mammal who is the recipient of the cells in a transplantation procedure, ie., the cells of the composition are derived or harvested from the mammal prior to any described modification.

In one embodiment of this aspect and all other aspects described herein, the cells of any compositions described are non-autologous to the mammal who is the recipient of the cells in a transplantation procedure, ie., the cells of the composition are not derived or harvested from the mammal prior to any described modification.

In one embodiment of this aspect and all other aspects described herein, the cells of any compositions described are at the minimum HLA type matched with to the mammal who is the recipient of the cells in a transplantation procedure.

In one embodiment of this aspect and all other aspects described herein, the cells of any compositions described are isolated progenitor cells prior to any described modification.

In one embodiment of this aspect and all other aspects described herein, the cells of any compositions described are isolated hematopoietic progenitor cells prior to any described modification.

In one embodiment of this aspect and all other aspects described herein, the cells of any compositions described are isolated induced pluripotent stem cells prior to any described modification.

In another embodiment of this aspect and all other aspects described herein, the deletion comprises one or more of the DNAse 1-hypersensitive sites (DHS) +62, +58, and +55 as described herein in the Examples section. In another embodiment of this aspect and all other aspects described herein, the deletion consists essentially of one or more of the DNAse 1-hypersensitive sites (DHS) +62, +58, and +55 as described herein in the Examples section. In another embodiment, the deletion consists of one or more of the DNAse 1-hypersensitive sites (DHS) +62, +58, and +55 as described herein in the Examples section. In one embodiment, as used herein, the term "portion" in the context of genomic deletion is at least 10% to about 100% of the specified region. In other embodiments, the portion deleted is at least 20%, at least 30%, at least 40%, at least 50%, at least 60%, at least 70%, at least 80%, at least 90%, at least 95%, at least 99% or even 100% of the specified region.

In another embodiment of this aspect and all other aspects described herein, the deletion comprises one or more of the SNP markers described in Table 2. In another embodiment of this aspect and all other aspects described herein, the deletion consists essentially of one or more of the SNP markers described in Table 2. In another embodiment of this aspect and all other aspects described herein, the deletion consists of one or more of the SNP markers described in Table 2.

In another embodiment of this aspect and all other aspects described herein, the deletion comprises one or more of the fragments listed in Table 7. In another embodiment of this aspect and all other aspects described herein, the deletion consists essentially of one or more of the fragments listed in Table 7. In another embodiment of this aspect and all other aspects described herein, the deletion consists of one or more of the fragments listed in Table 7. In another embodiment of this aspect and all other aspects described herein, the deletion is from 60,716,189 to 60,728,612, from 60,716,189 to 60,723,870, from 60,722,992 to 60,728,612, from 60,717,236 to 60,719,036, from 60,722,006 to 60,723,058, from 60,724,917 to 60,726,282, from 60,616,396 to 60,618,032, from 60,623,536 to 60,624,989, from 60,626,565 to 60,628,177, from 60,717,236 to 60,719,036, from 60,721,212 to 60,722,958, from 60,724,780 to 60,726,471, from 60,739,075 to 60,740,154, from 60,748,003 to 60,749,009, from 60,826,438 to 60,827,601, or from 60,831,589 to 60,833,556.

In another embodiment of this aspect and all other aspects described herein, the deletion removes the entire region between chromosome 2 location 60,716,189-60,728,612 (according to UCSC Genome Browser hg 19 human genome assembly) or removes a portion of the region resulting in disruption of one or more DNAse 1-hypersensitive sites (DHS).

In one embodiment of this aspect and all other aspects described herein, the method further comprises selecting a mammal in need of increasing fetal hemoglobin.

In one embodiment of this aspect and all other aspects described herein, the mammal has been diagnosed with a hemoglobinopathy.

In one embodiment of this aspect and all other aspects described herein, the mammal in need of increasing fetal hemoglobin has been diagnosed with a hemoglobinopathy.

In one embodiment of this aspect and all other aspects described herein, the hemoglobinopathy is a β-hemoglobinopathy.

In one embodiment of this aspect and all other aspects described herein, the hemoglobinopathy is sickle cell disease.

In one embodiment of this aspect and all other aspects described herein, the hemoglobinopathy is β-thalassemia.

In one embodiment of this aspect and all other aspects described herein, the contacted cell, human cell, hematopoietic progenitor cell or its progeny is administered to the mammal.

In one embodiment, this disclosure provides a method for increasing fetal hemoglobin levels in a mammal in need thereof, the method comprising the steps of providing an isolated population of hematopoietic progenitor cells or hematopoietic stem cells from the mammal in ex vivo, and contacting the population of hematopoietic progenitor or stem cells with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 causing at least one genetic modification therein, whereby fetal hemoglobin expression is increased in the mammal, relative to expression prior to the contacting. In further embodiment of this method, the contacted population of hematopoietic progenitor or stem cells having increased fetal hemoglobin expression is cryopreserved and stored or reintroduced into the mammal. In another embodiment, the cryopreserved population of hematopoietic progenitor or stem cells having increased fetal hemoglobin expression is thawed and then reintroduced into the mammal. In further embodiment of this method, the method comprises chemotherapy and/or radiation therapy to remove or reduced the endogenous hematopoietic progenitor or stem cells in the mammal. In any of the embodiment of the described method, the hematopoietic progenitor or stem cells can be substituted with an iPSCs described herein.

In one embodiment, this disclosure provides a method for increasing fetal hemoglobin levels in a mammal in need thereof, the method comprising the steps of isolating a population of hematopoietic progenitor cells or hematopoietic stem cells from the mammal, and contacting in ex vivo the population of hematopoietic progenitor or stem cells with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 causing at least one genetic modification therein, whereby fetal hemoglobin expression is increased in the mammal, relative to expression prior to the contacting. In further embodiment of this method, the ex vivo contacted population of hematopoietic progenitor or stem cells having increased fetal hemoglobin expression is cryopreserved and stored or reintroduced into the mammal. In another embodiment, the cryopreserved population of hematopoietic progenitor or stem cells having increased fetal hemoglobin expression is thawed and then reintroduced into the mammal. In further embodiment of this method, the method comprises chemotherapy and/or radiation therapy to remove or reduced the endogenous hematopoietic progenitor or stem cells in the mammal. In any of the embodiment of the described method, the hematopoietic progenitor or stem cells can be substituted with an iPSCs derived from the mammal. In any embodiment of the method, the method further comprises selecting a mammal in need of increased fetal hemoglobin expression.

In one embodiment, this disclosure provides a method for increasing fetal hemoglobin levels in a mammal in need thereof, the method comprising the steps of providing isolating a population of hematopoietic progenitor cells or hematopoietic stem cells from the mammal and deleting the genomic DNA of the cells on chromosome 2 location 60,716,189-60,728,612 causing at least one genetic modification therein, whereby fetal hemoglobin expression is increased in said mammal, relative to expression prior to said contacting. In further embodiment of this method, the population of hematopoietic progenitor or stem cells with deleted genomic DNA and having increased fetal hemoglobin expression is cryopreserved and stored or reintroduced into the mammal. In another embodiment, the population of hematopoietic progenitor or stem cells with deleted genomic DNA and having increased fetal hemoglobin expression is thawed and then reintroduced into the mammal. In further embodiment of this method, the method comprises chemotherapy and/or radiation therapy to remove or reduced the endogenous hematopoietic progenitor or stem cells in the mammal. In any of the embodiment of the described method, the hematopoietic progenitor or stem cells can be substituted with an iPSCs described herein. In any of the embodiment of the described method, the hematopoietic progenitor or stem cells or iPSCs are analogous to the mammal, meaning the cells are derived from the same mammal. In another of the embodiment of the described method, the hematopoietic progenitor or stem cells or iPSCs are non-analogous to the mammal, meaning the cells are not derived from the same mammal, but another mammal of the same species. For example, the mammal is a human. In any embodiment of the method, the method further comprises selecting a mammal in need of increased fetal hemoglobin expression.

In one embodiment, this disclosure provides a method for increasing fetal hemoglobin levels in a mammal in need thereof, the method comprising the steps of isolating a population of hematopoietic progenitor cells or hematopoietic stem cells from the mammal and ex vivo deleting the genomic DNA of the cells on chromosome 2 location 60,716,189-60,728,612 causing at least one genetic modification therein, whereby fetal hemoglobin expression is increased in said mammal, relative to expression prior to said contacting. In further embodiment of this method, the population of hematopoietic progenitor or stem cells with deleted genomic DNA and having increased fetal hemoglobin expression is cryopreserved and stored or reintroduced into the mammal. In another embodiment, the cryopreserved population of hematopoietic progenitor or stem cells having increased fetal hemoglobin expression is thawed and then reintroduced into the mammal. In further embodiment of this method, the method comprises chemotherapy and/or radiation therapy to remove or reduced the endogenous hematopoietic progenitor or stem cells in the mammal. In any of the embodiment of the described method, the hematopoietic progenitor or stem cells can be substituted with an iPSCs derived from the mammal. In any embodiment of the method, the method further comprises selecting a mammal in need of increased fetal hemoglobin expression.

In one embodiment of any method described, the method further comprises selecting a mammal in need of increased fetal hemoglobin expression. Exemplary mammal in need of increased fetal hemoglobin expression is one that has been diagnosed with a hemoglobinopathy.

In one embodiment, this disclosure provides a method of treatment of a hemoglobinopathy in a mammal comprising the steps of (a) providing hematopoietic progenitor cells or hematopoietic stem cells or iPSCs; (b) contacting the cells ex vivo or in vitro with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 causing at least one genetic modification therein, whereby fetal hemoglobin expression is increased in said mammal, relative to expression prior to said contacting; and (c) administering the cells of step (b) into the mammal.

In one embodiment of any method, the cells after step (b) can be cryopreserved till they are needed for administration into the mammal. In further embodiment of this method, the method comprises chemotherapy and/or radiation therapy to remove or reduced the endogenous hematopoietic progenitor or stem cells in the mammal. In any of the embodiment of the described method, the hematopoietic progenitor or stem cells or iPSCs are autologous to the mammal, meaning the cells are derived from the same mammal. In another of the embodiment of the described method, the hematopoietic progenitor or stem cells or iPSCs are non-autologous to the mammal, meaning the cells are not derived from the same mammal, but another mammal of the same species. For example, the mammal is a human.

In one embodiment of any method described, the method further comprises selecting a mammal in need of treatment of a hemoglobinopathy.

In one embodiment, this disclosure provides a method of treatment of a hemoglobinopathy in a mammal comprising the steps of (a) isolating hematopoietic progenitor cells or hematopoietic stem cells from the mammal;(b) contacting the cells ex vivo or in vitro with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 causing at least one genetic modification therein, whereby fetal hemoglobin expression is increased in the mammal, relative to expression prior to said contacting; and (c) administering the cells of step (b) into the mammal.

In one embodiment, the cells after step (b) can be cryopreserved till they are needed for administration into the mammal. In any embodiment of the method, the method further comprises selecting a mammal in need of treatment of a hemoglobinopathy.

In one embodiment, this disclosure provides a method of treatment of a hemoglobinopathy in a mammal comprising the steps of: (a) providing hematopoietic progenitor cells or hematopoietic stem cells or iPSCs; (b) ex vivo deleting the genomic DNA of the cells on chromosome 2 location 60,716,189-60,728,612 causing at least one genetic modification therein, whereby fetal hemoglobin expression is increased in said mammal, relative to expression prior to said contacting; and (c) administering the cells of step (b) into the mammal.

In one embodiment, the cells after step (b) can be cryopreserved till they are needed for administration into the mammal. In further embodiment of this method, the method comprises chemotherapy and/or radiation therapy to remove or reduced the endogenous hematopoietic progenitor or stem cells in the mammal. In any of the embodiment of the described method, the hematopoietic progenitor or stem cells or iPSCs are analogous to the mammal, meaning the cells are derived from the same mammal. In another of the embodiments of the described method, the hematopoietic progenitor or stem cells or iPSCs are non-analogous to the mammal, meaning the cells are not derived from the same mammal, but another mammal of the same species. For example, the mammal is a human. In any embodiment of the method, the method further comprises selecting a mammal in need of treatment of a hemoglobinopathy.

In one embodiment, this disclosure provides a method of treatment of a hemoglobinopathy in a mammal comprising the steps of: (a) isolating hematopoietic progenitor cells or hematopoietic stem cells from the mammal; (b) ex vivo deleting the genomic DNA of the cells on chromosome 2 location 60,716,189-60,728,612 causing at least one genetic modification therein, whereby fetal hemoglobin expression is increased in the mammal, relative to expression prior to said contacting; and (c) administering the cells of step (b) into the mammal.

In one embodiment, the cells after step (b) can be cryopreserved till they are needed for administration into the mammal. In further embodiment of this method, the method comprises chemotherapy and/or radiation therapy to remove or reduced the endogenous hematopoietic progenitor or stem cells in the mammal. In any embodiment of the method, the method further comprises selecting a mammal in need of treatment of a hemoglobinopathy.

In one embodiment, this disclosure provides a method of treatment of a hemoglobinopathy in a mammal (e.g. a human) comprising introducing a composition described herein comprising isolated genetic engineered cells having at least one genetic modification on chromosome 2 location 60,716,189-60,728,612 whereby fetal hemoglobin expression is increased in the mammal. In further embodiment of this method, the method comprises chemotherapy and/or radiation therapy to remove or reduced the endogenous hematopoietic progenitor or stem cells in the mammal. In any embodiment of the method, the method further comprises selecting a mammal in need of treatment of a hemoglobinopathy.

In one embodiment, this disclosure provides a method of treatment of a hemoglobinopathy in a mammal (e.g. a human) comprising increasing fetal hemoglobin expression in the mammal by method described herein.

In any embodiment of any treatment method described, the hemoglobinopathy is a β-hemoglobinopathy.

In any embodiment of any treatment method described, the hemoglobinopathy is β-thalassemia.

In any embodiment of any treatment method described, the hemoglobinopathy is sickle cell anemia.

In one of embodiment of any described method, the hematopoietic progenitor or stem cells or iPSCs are autologous to the mammal, meaning the cells are derived from the same mammal. In another of the embodiment of any described method, the hematopoietic progenitor or stem cells or iPSCs are non-autologous to the mammal, meaning the cells are not derived from the same mammal, but another mammal of the same species. For example, the mammal is a human.

In one of embodiment of any described method, the contacting of any cell described herein can be ex vivo or in vitro or in vivo.

In another embodiment of any described method, the contacting of any cell described herein comprises contact with an agent that binds the genomic DNA of the cell on chromosome 2 and produces an epigenetic modification in the genome of the cell on chromosome 2, thereby reducing the mRNA or protein expression of BCL11A. In one embodiment, the epigenetic modification is on chromosome 2 location 60,716,189-60,728,612 (according to UCSC Genome Browser hg 19 human genome assembly).

In another embodiment of any described method, the contacting of any cell described herein comprises contact with an agent that binds the genomic DNA of the cell on chromosome 2 location 60,716,189-60,728,612 (according to UCSC Genome Browser hg 19 human genome assembly), and produces an epigenetic modification on chromosome 2, thereby reducing the mRNA or protein expression of BCL11A.

In another embodiment of any described method, the contacting of any cell described herein comprises contact with an effective amount of a composition comprising at least a DNA-targeting enzyme or a vector carrying the coding sequence of a DNA-targeting enzyme whereby the DNA-targeting enzyme produces an epigenetic modification on chromosome 2, thereby reducing the mRNA or protein expression of BCL11A.

In another embodiment of any described method, the contacting of any cell described herein comprises contact with an effective amount of a composition comprising at least a DNA-targeting enzyme or a vector carrying the coding sequence of a DNA-targeting enzyme whereby the DNA-targeting enzyme produces an epigenetic modification on chromosome 2 location 60,716,189-60,728,612 (according to UCSC Genome Browser hg 19 human genome assembly) thereby reducing the mRNA or protein expression of BCL11A. In one aspect, fetal hemoglobin expression is increased in the mammal, relative to expression prior to the contacting.

In another embodiment of any described method, the hematopoietic progenitor cell, the isolated human cell, or isolated cell is contacted ex vivo or in vitro.

In another embodiment of any described method, the at least one genetic modification is a deletion. In another embodiment of this aspect and all other aspects described herein, the at least one epigenetic modification is a deletion.

In one embodiment, provided herein is a use of an agent that binds the genomic DNA of the cell on chromosome 2 location 60,716,189-60,728,612 (according to UCSC Genome Browser hg 19 human genome assembly) for increasing the fetal hemoglobin in a mammal or for the treatment of a hemoglobinopathy in the mammal or for reducing the mRNA or expression of BCL11A, wherein the mRNA or protein expression of BCL11A is reduced.

In one embodiment, provided herein is a use of an effective amount of a composition comprising at least a DNA-targeting endonuclease or a vector carrying the coding sequence of a DNA-targeting endonuclease for increasing the fetal hemoglobin in a mammal or for the treatment of a hemoglobinopathy in the mammal or for reducing the mRNA or expression of BCL11A, wherein the DNA-targeting endonuclease cleaves the genomic DNA of the cell on chromosome 2 location 60,716,189-60,728,612 causing at least one genetic modification therein.

In one embodiment, provided herein is a use of an effective amount of a composition comprising at least a DNA-targeting enzyme or a vector carrying the coding sequence of a DNA-targeting enzyme for increasing the fetal hemoglobin in a mammal or for the treatment of a hemoglobinopathy in the mammal or for reducing the mRNA or expression of BCL11A, wherein the DNA-targeting enzyme produces at least one epigenetic modification in the genomic DNA of the cell on chromosome 2, thereby affecting the mRNA or expression of BCL11A. In one embodiment, the at least one epigenetic modification is at location 60,716, 189-60,728,612. In another embodiment, the effect of the one epigenetic modification is reducing the mRNA or protein expression of BCL11A.

In one embodiment, provided herein is a use of any isolated cells described herein for increasing the fetal hemoglobin in a mammal or for the treatment of a hemoglobinopathy in the mammal.

In one embodiment, provided herein is a use of a composition comprising isolated genetic engineered human cells for increasing the fetal hemoglobin in a mammal or for the treatment of a hemoglobinopathy in the mammal, wherein the cells have at least one genetic modification on chromosome 2 location 60,716,189-60,728,612 (according to UCSC Genome Browser hg 19 human genome assembly) made by the process of contacting the cells with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 (according to UCSC Genome Browser hg 19 human genome assembly) causing at least one genetic modification therein.

In one embodiment, provided herein is a use of a composition comprising isolated genetic engineered human cells for increasing the fetal hemoglobin in a mammal or for the treatment of a hemoglobinopathy in the mammal, wherein the cells have at least one epigenetic modification on chromosome 2. In one embodiment, the at least one epigenetic modification on chromosome 2 is at location 60,716,189-60,728,612 (according to UCSC Genome Browser hg 19 human genome assembly). In another embodiment, at least one epigenetic modification on chromosome 2 is made by the process of contacting the cells with an effective amount of a composition comprising at least a DNA-targeting enzyme or a vector carrying the coding sequence of a DNA-targeting enzyme whereby the DNA-targeting enzyme produces at least one epigenetic modification in the genomic DNA of the cell on chromosome 2 which affects the location 60,716,189-60,728,612 (according to UCSC Genome Browser hg 19 human genome assembly) causing therein.

In one embodiment, provided herein is a use of any isolated cells described herein or any one of the compositions described herein for the manufacture of a medicament for increasing the fetal hemoglobin in a mammal or for the treatment of a hemoglobinopathy in the mammal.

In one embodiment of use of the composition described herein, the composition causes an increase in fetal hemoglobin mRNA or protein expression in the contact cell.

In one embodiment of use of the composition described herein, the cells of any compositions described are autologous, to the mammal who is the recipient of the cells in a transplantation procedure, ie., the cells of the composition are derived or harvested from the mammal prior to any described modification.

In one embodiment of use of the composition described herein, the cells of any compositions described are non-autologous to the mammal who is the recipient of the cells in a transplantation procedure, ie., the cells of the composition are not derived or harvested from the mammal prior to any described modification.

In one embodiment of use of the composition described herein, the cells of any compositions described are at the minimum HLA type matched with to the mammal who is the recipient of the cells in a transplantation procedure.

In one embodiment of use of the composition described herein, the cells of any compositions described are isolated progenitor cells prior to any described modification.

In one embodiment of use of the composition described herein, the cells of any compositions described are isolated hematopoietic progenitor cells prior to any described modification.

In one embodiment of use of the composition described herein, the cells of any compositions described are isolated induced pluripotent stem cells prior to any described modification.

In one embodiment of use of the composition described herein, the cells of any compositions described are cryopreserved prior to use.

Figure 2A:
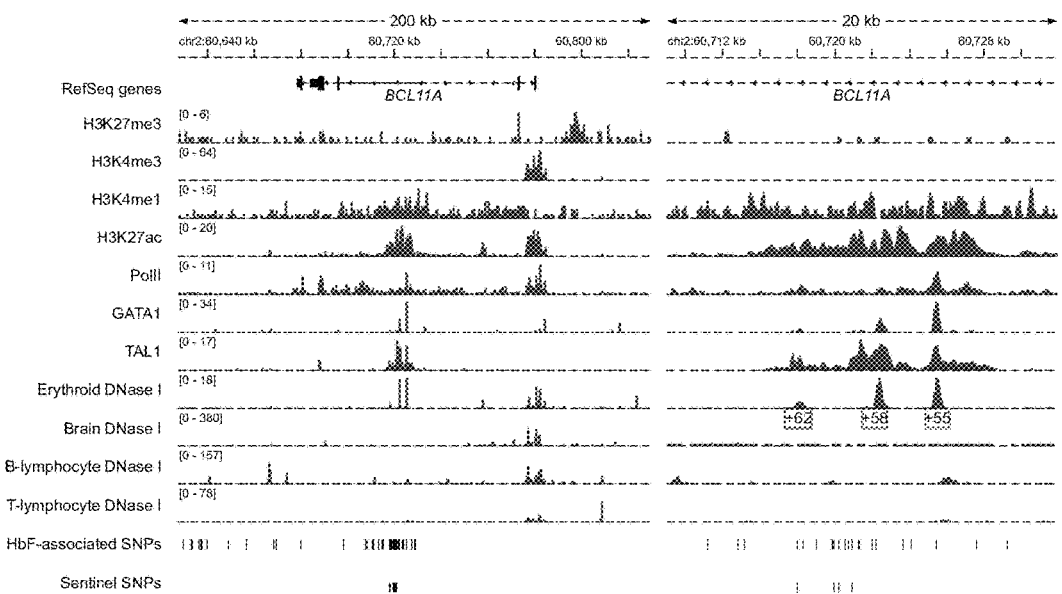
FIG. 2A shows ChIP followed by massively parallel sequencing performed from CD34+-cell-derived erythroid precursors with antibodies to H3K27me3, H3K4me3, H3K4me1, H3K27ac, GATA1, TAL1, and PolII. Nuclei isolated from erythroid precursors, fetal brain, and B- and T-lymphocytes subject to DNase I treatment with sites of cleavage determined by massively parallel sequencing. HbF-associated SNPs includes those associated with HbF level or F-cell number at $P<5\times10^{-8}$ and sentinel SNPs those with highest association to HbF or F-cell number in a given GWAS. Three adjacent erythroid DHS are labeled as +62, +58, and +55 based on distance in kb from BCL11A TSS.
Figure 11A:
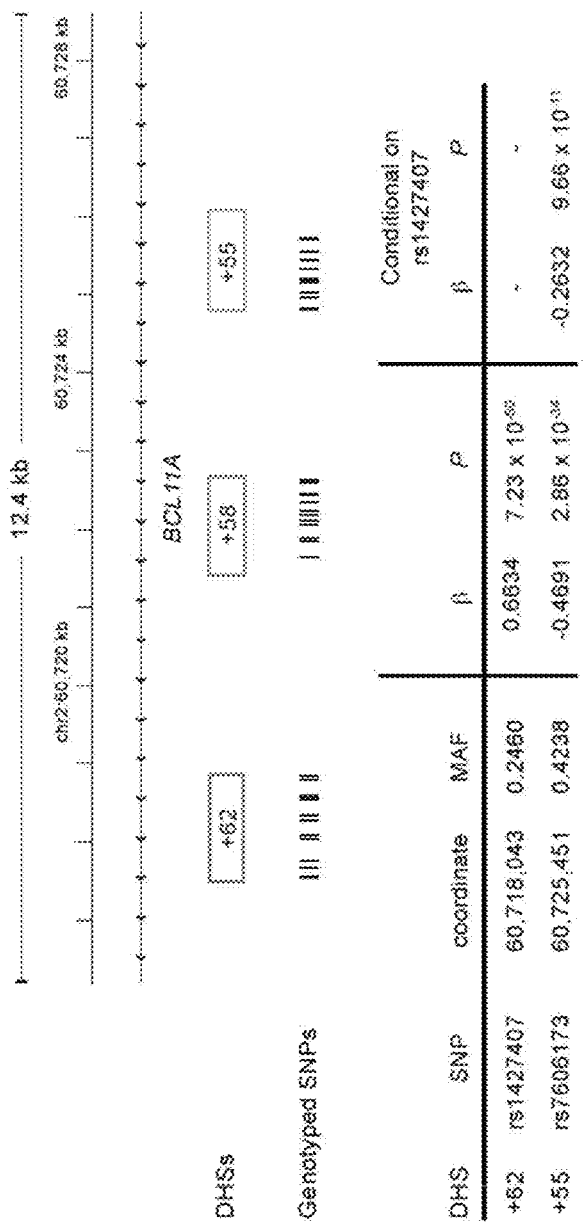
FIG. 11A shows the genotype data obtained in 1,178 individuals from CSSCD for 38 variants within BCL11A +62, +58 or +55 DHSs. Most highly significant associations to HbF level among common (MAF>1%) SNPs (n=10) prior to (rs1427407) or following (rs7606173) conditional analysis on rs1427407. SNP coordinates chromosome 2, building19.
Figure 11B:
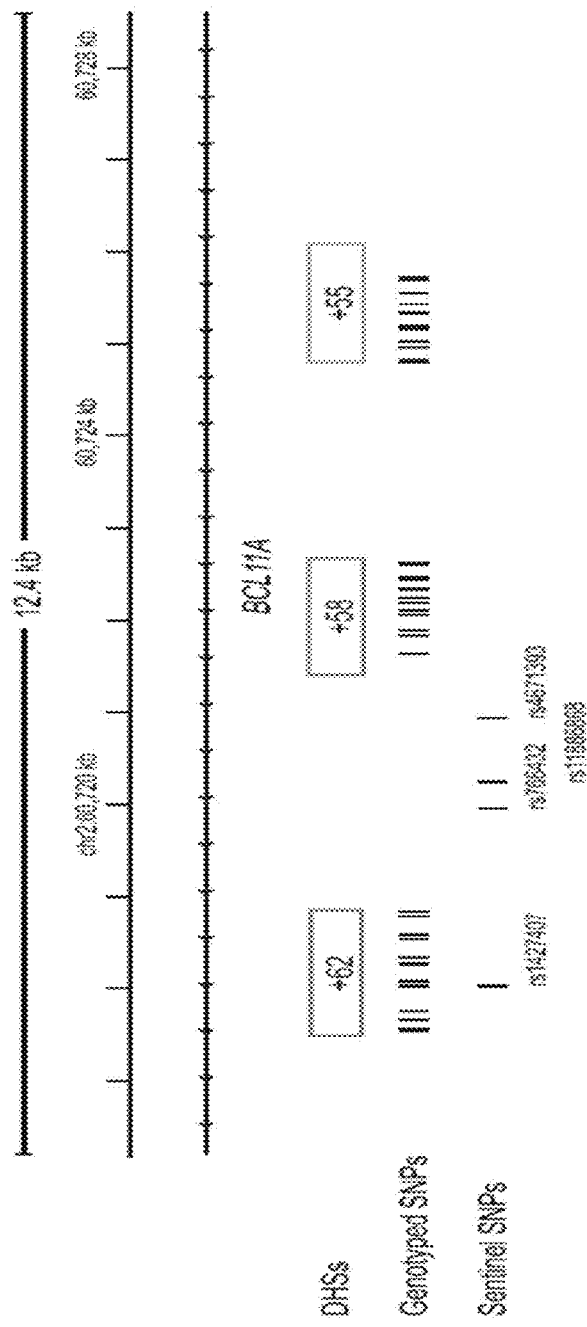
FIG. 11B the HbF association analyses at BCL11A. Genotype data obtained in 1,178 individuals from CSSCD for 38 variants within BCL11A +62, +58 or +55 DHSs. Sentinel SNPs are those with the highest association to HbF level or F-cell number in prior GWAS (7-12). These SNPs are shown with respect to BCL11A intron-2 with the 3 DHSs +62, +58 and +55 indicated.

It is known that there are HbF-associated variations at BCL11A. Six GWAS of HbF level (or the highly correlated trait F-cell number) have been conducted in individuals of European, African and Asian descent, each identifying trait-associated variants within BCL11A (7-12). The same variants are associated with the clinical severity of SCD and β-thalassemia (9, 10, 50), consistent with HbF as a major modifier of these disorders. Variation at BCL11A is estimated to explain ~15% of the trait variance in HbF level (7, 12, 43). Four different SNPs have been identified as most highly associated with the trait (rs1427407 (7), rs11886868 (8), rs4671393 (9) and rs766432 (10-12)); these sentinel SNPs cluster within 3 kb of each other in BCL11A intron-2 (FIGS. 2A and 11B). Haplotypes including the sentinel SNPs appear to better explain the HbF association than any individual SNP (12, 43). Fifty SNPs at the BCL11A locus and twenty-seven SNPs within intron-2 have been associated with HbF level with genome-wide significance ($P<5\times 10^{-8}$). Despite large-scale resequencing efforts, coding variants of BCL11A have not been described (43).

Previously, the inventors used the CSSCD to fine-map the association signal with HbF at the BCL11A locus and reported a strong association with rs4671393 (43). In that study, rs1427407 was imputed. Two additional SNPs, rs766432 and rs11886868 have also been identified in prior studies as sentinel SNPs most highly trait-associated (8, 10, 11, 51). In a subset of individuals (n=728) for which genotypes at all four sentinel SNPs were available, the association result was not significant at rs4671393, rs766432 or rs11886868 following conditioning on genotypes at rs1427407; conversely, the association remained highly significant for rs1427407 upon conditioning on rs4671393, rs766432 or rs11886868 (Table 4). Therefore, rs1427407 is the SNP most strongly associated with HbF level within the erythroid DHSs and better accounts for the trait association than other previously described sentinel SNPs.

Conditional analysis demonstrated associations that remained significant after conditioning on rs1427407. The most significant residual association was for rs7606173 in DHS +55 ($P=9.66\times10^{-11}$); rs7599488 in DHS +62, which we had previously reported (43), was only slightly less significant ($P=2.43\times10^{-10}$) (Table 1). Analysis of rare DNA sequence variants within the three DHSs did not yield additional independent HbF-associated signals (Table 5).

Figure 2B:
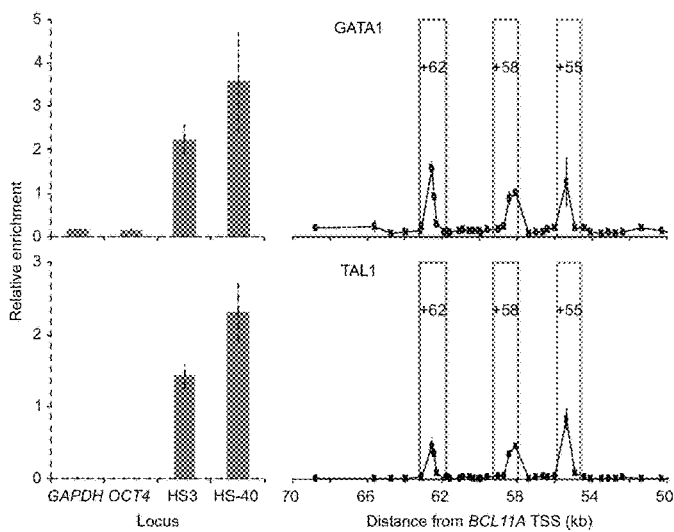
FIG. 2B shows ChIP-qPCR of primary human erythroid precursors at BCL11A intron-2, normalized to 1% input chromatin. DHS +62, +58, and +55 from FIG. 2A shaded. Enrichment at negative control (GAPDH, OCT4) and positive control (β-globin LCR HS3 and α-globin HS-40) loci displayed for comparison.

The inventors have found that allele-specific transcription factor (TF) binding are involved with BCL11A expression. Allele-specific biochemical studies were performed using informative heterozygotes to control for trans-acting differences between samples and to ensure equal abundance of both alleles, substantiated by equal representation of alleles in paired gDNA (FIGS. 2B and 2C). rs1427407 is found directly at the center of a GATA1 and TAL1 binding peak at DHS +62 (FIG. 2B). In the ChIP assays performed, chromatin was sonicated to approximately 500-bp fragments. The five primary human erythroid precursor samples heterozygous for rs1427407 used for ChIP-qPCR were Sanger sequenced at the erythroid DHSs. The only other heterozygous SNP within 500-bp of rs1427407 in any of these samples was rs7599488 (304-bp 3' of rs1427407) which was heterozygous in just two of the five samples. This SNP does not fall within GATA1 or TAL1 binding motifs. It therefore appears unlikely that another SNP within DHS +62 could account for the observed allele-specific TF binding.

Figure 3A:
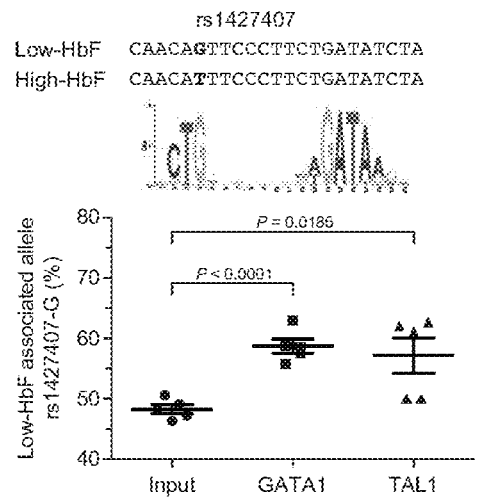
FIG. 3A shows Healthy anonymous donors from whom hematopoietic stem/progenitor cells were available were genotyped at rs1427407 to identify heterozygous individuals. Five donors were identified. The hematopoietic stem/progenitor cells were subject to erythroid differentiation culture. Chromatin was isolated from erythroblasts, and immunoprecipitated by GATA1 or TAL 1. ChIP DNA or input DNA was subject to a pyrosequencing reaction to quantify the relative abundance of the rs1427407 G-allele. Figure discloses SEQ ID NOS 197 and 198, respectively, in order of appearance.
Figure 3B:
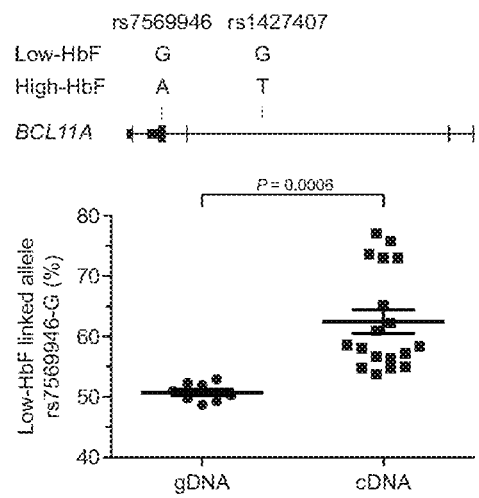
FIG. 3B shows data from Healthy anonymous donors from whom hematopoietic stem/progenitor cells were available were genotyped at rs1427407, rs7606173, and rs7569946 to identify individuals heterozygous for the rs1427407-rs7606173 haplotype as well as rs7569946. Three donors were identified. Haplotyping revealed that the rs7569946 G-allele was on the same chromosome as the rs1427407 G-allele and rs7606173 C-allele in each. The hematopoietic stem/progenitor cells were subject to erythroid differentiation culture. RNA and genomic DNA were isolated, and cDNA was produced by reverse transcription. Paired gDNA and cDNA samples were subject to a pyrosequencing reaction to quantify the relative abundance of the 7569946 G-allele.
Figure 3C:
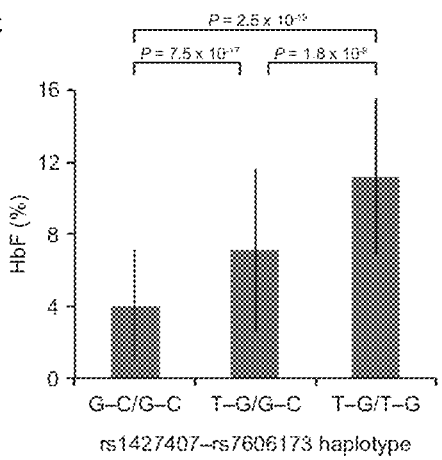
FIG. 3C shows mean HbF for rs1427407-rs7606173 haplotypes in the CSSCD cohort. The mean HbF level was 4.05% (SD 3.10) in 213 rs1427407-rs7606173 G-C individuals, 7.08% (SD 4.50) in 254 rs1427407-rs7606173 T-G/G-C heterozygotes, and 11.21% (SD 4.37) in 60 rs1427407-rs7606173 T-G individuals. The P-values correspond to one-tailed student t-tests. The haplotype frequencies in CSSCD are: TG: 24.5%, TC 0.085%, GC 42.3%, GG 33.1%.

In addition, the inventors have found that there is an association between BCL11A expression and HbF level. The inventors' studies provide an estimate of the change in BCL11A expression that may result in a clinically meaningful increase in HbF level. Among a limited set of human lymphoblastoid cell lines were previously reported correlation of the high HbF-associated A-allele of rs4671393 with reduced BCL11A expression (13). Extension of these experiments to a larger collection of genotyped lines failed to confirm this observation. Hence, The inventors have found that the HbF-associated rs1427407-rs7606173 haplotype influence BCL11A expression in an erythroid-specific context, a possibility consistent with the DNase I sensitivity findings BCL11A mRNA expression in primary erythroid precursors differed by 1.7-fold between the high-HbF rs1427407-rs7606173 T-G and low-HbF G-C haplotypes (FIG. 3B); correspondingly, median HbF levels were 10.6% and 3.1% in T-G and G-C homozygotes, respectively (FIG. 3C). Of note, the results demonstrating allele-specific expression of BCL11A in primary human erythroid cells were observed in cells modigygous for the rs1427407-rs7606173 haplotype, and thus the modest effects on BCL11A expression reflect the combined effects of all functional SNPs within the haplotype. While inheritance of a protective BCL11A haplotype is clinically beneficial on a population basis (9, 10, 50), the average level of HbF in T-G homozygotes remains below that required to prevent morbidity from SCD. The sensitivity of HbF level to BCL11A expression, however, predicts that relief of disease severity might require only a modest further reduction in BCL11A expression.

The inventors further investigated the developmental regulation of globin genes and BCL11A. During human development, yolk sac-derived ε-globin is superseded in the first trimester by fetal liver-derived γ-globin. Following birth, as erythropoiesis shifts from the liver to the bone marrow, γ-globin is gradually silenced and β-globin predominates. Only a single switch in globin gene expression occurs in mouse ontogeny. During this transition, which occurs at mid-gestation, the circulating yolk sac-derived primitive erythrocytes express embryonic-stage globins εy and βH1, whereas the fetal liver definitive erythroblasts express adult-stage globins β1 and β2. Concordant with this developmental switch, BCL11A is expressed in the definitive but not primitive-stage erythroid lineage and required for the change in globin gene expression (16, 52).

Figure 6A:
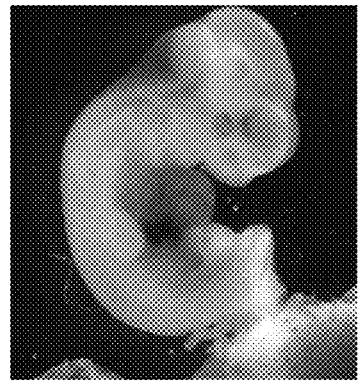
FIG. 6 shows mouse zygote pronuclei injected with lacZ reporter construct. Transgenic embryos were isolated at E12.5. Embryos were genotyped by lacZ PCR. The fraction of transgenic embryos with X-gal staining of fetal liver is reported.

In the stable transgenic BCL11A +52.0-64.4 reporter lines at 10.5 dpc, lacZ expression was observed only in the fetal liver primordium and not in the circulating blood within the embryo, placenta or yolk sac (FIG. 6A). These results, coupled with the finding of lacZ expression in the 12.5 dpc definitive fetal liver erythroblasts but not yolk sac-derived primitive circulating erythrocytes (FIG. 4B), demonstrate that the BCL11A composite enhancer sequences drive expression in a developmentally-specific pattern concordant with endogenous globin gene switching.

Figure 6B:
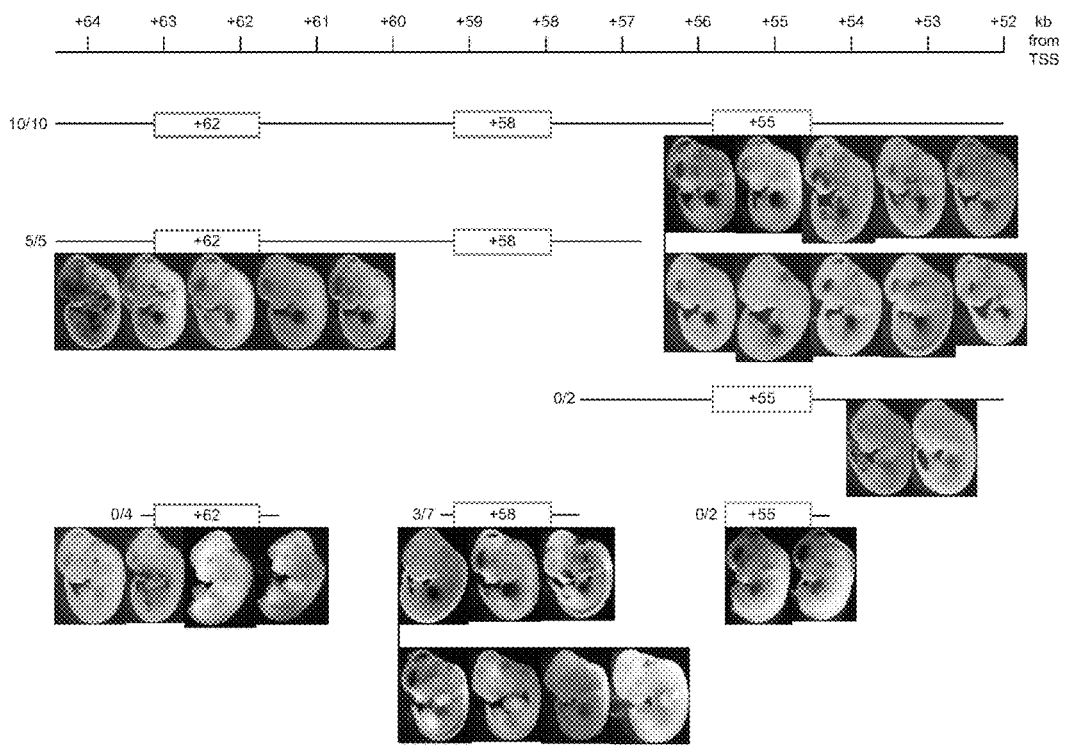
Figure 7:
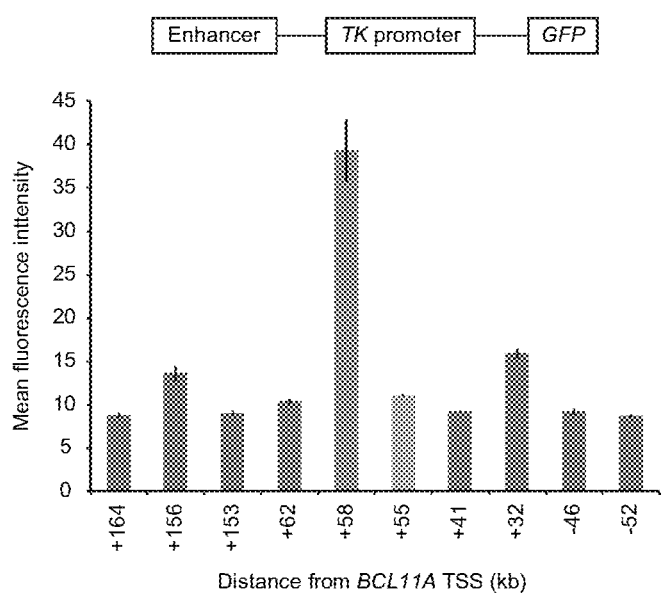
FIG. 7 shows one to two kb sequence fragments cloned into enhancer construct with TK minimal promoter and GFP Enhancer reporter constructs were delivered by lentiviral vectors to primary human erythroid precursors. Transfected cells were selected by puromycin resistance. Mean GFP fluorescence intensity was measured.

A series of deletion mutants was generated to refine the minimal elements required for erythroid enhancer activity. Sequences containing the central +58 DHS were sufficient for erythroid enhancer activity. Those sequences containing only the flanking +62 or +55 elements were unable to direct erythroid gene expression (FIG. 6B). To test the ability of the DHSs to enhance gene expression in primary human erythroid precursors, we used lentiviral delivery of a GFP reporter system as previously described (39). Similarly, the +58 DHS enhanced gene expression in this reporter assay (FIG. 7).

Figure 8:
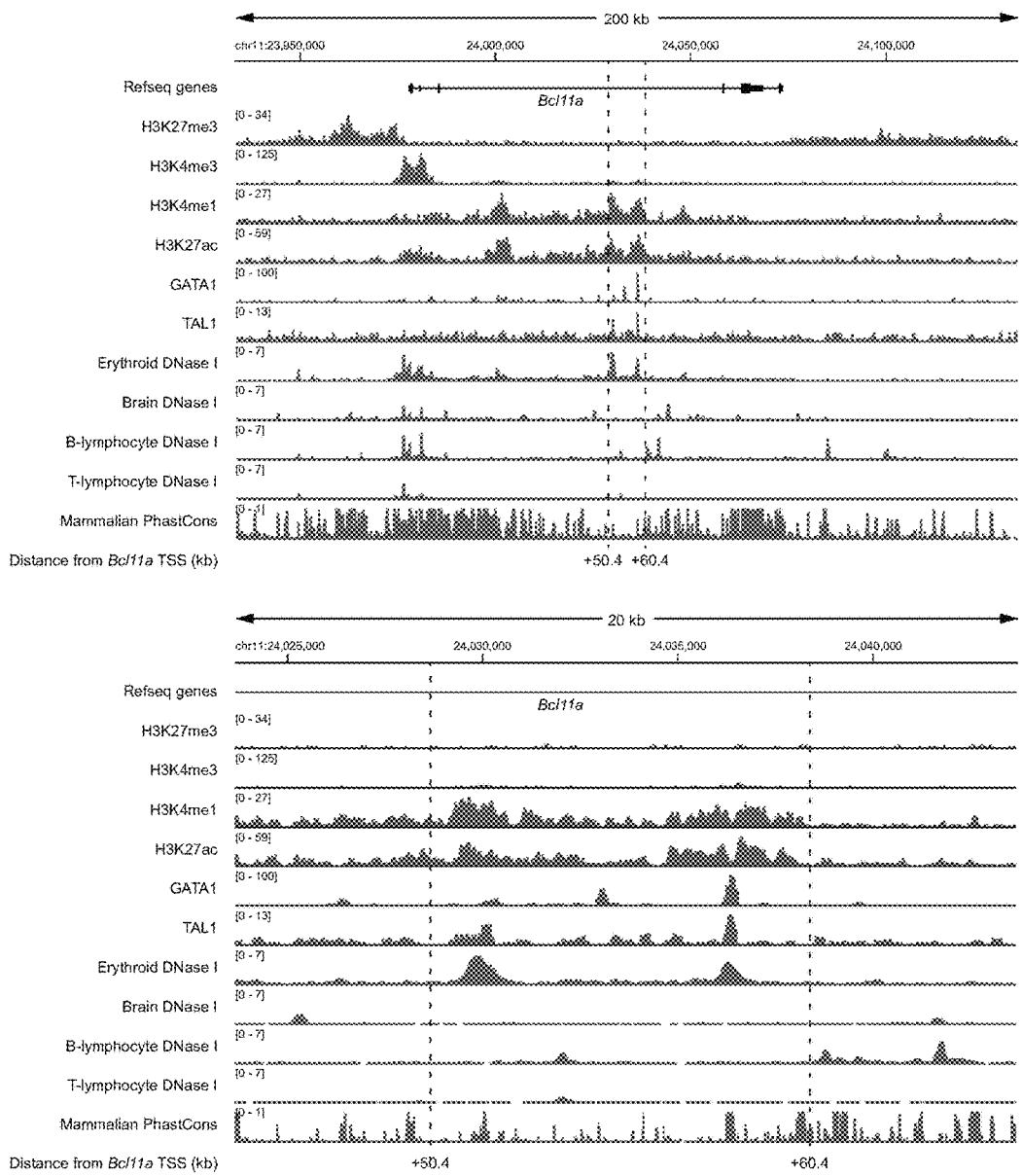
FIG. 8 shows data relating to chromatin profiling of mouse erythroid cells that reveals an orthologous enhancer signature at Bcl11a intron-2. Mouse tracks obtained from previously published global mouse erythroid chromatin profiling, with histone modifications and DNase-I cleavage from and GATA1 and TAL1 ChIP-seq from. Dotted rectangle bounds orthologous enhancer signature defining Δ50.4-60.4 element targeted for TALEN-mediated deletion.
Figure 9A:
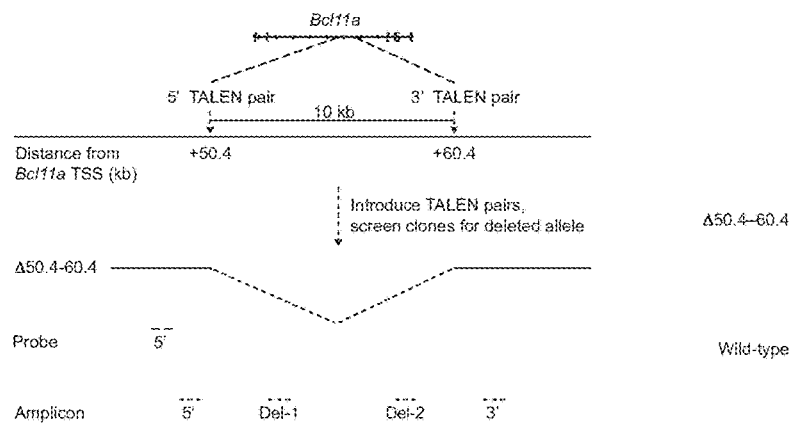
FIG. 9A is a schematic of a TALEN-mediated genome engineering strategy used herein. TALENs are sequence-specific nucleases. Two pairs of TALENs were engineered to generate double strand breaks, one at Bcl11a +50.4 and the other at +60.4. Clones were isolated that had repaired the two DSBs by NHEJ with excision of the intervening 10-kb segment. Clones were screened by PCR with primers 5', 3', internal and spanning the 10-kb deletion.
Figure 9B:
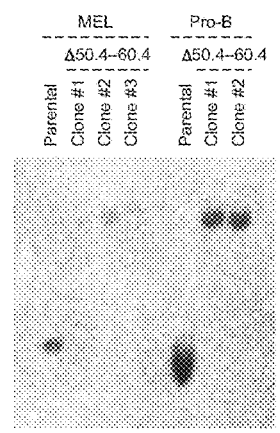
FIG. 9B shows Southern blotting of HindIII digested genomic DNA from Δ50.4-60.4 clones corroborated that these clones had expected excision allele and lacked a non-excised allele.
Figure 9C:
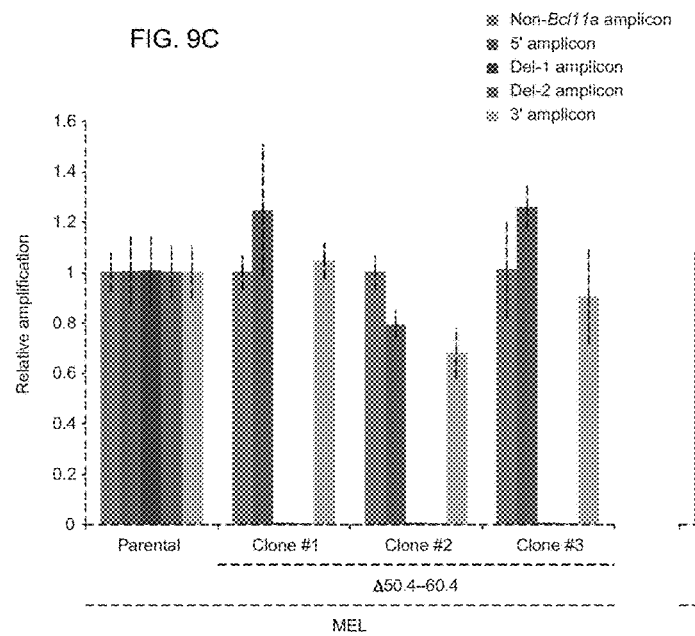
FIG. 9C shows the Δ50.4-60.4 clones having biallelic BCL11A enhancer deletion produced by TALEN-mediated NHEJ in mouse erythroleukemia (MEL) cells and pro-B lymphoid cells. The histograms show PCR amplification produced using the primers 5', 3', internal and spanning the 10-kb deletion (see amplicons in FIG. 9A). All Δ50.4-60.4 clones were missing Del-1 and Del-2 amplification, indicating the presence of a biallelic deletion of the 10 kb BCL11A intron-2 erythroid enhancer from +50.4-+60.4 kb.
Figure 9C:
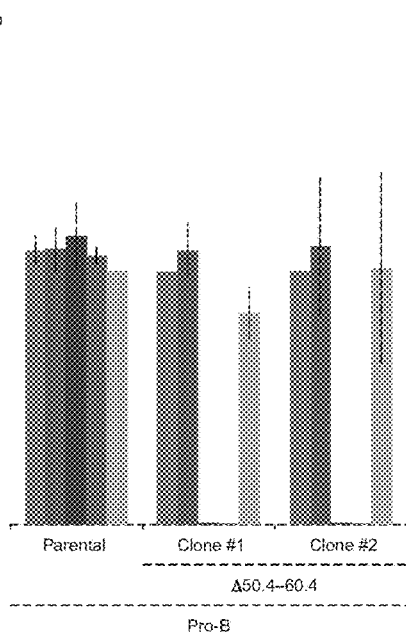

The inventors decided to generate cell lines with a Bcl11a enhancer deletion to investigate the requirement of the enhancer for BCL11A expression. Stable erythroid cells with disruption of the enhancer were generated. Since there are no suitable adult-stage human erythroid cell lines, and as proof of principle, the inventors turned to the murine system. Mouse erythroleukemia (MEL) cells depend on BCL11A for an adult-stage pattern of globin gene expression (14). The inventors identified an orthologous erythroid composite enhancer at mouse Bcl11a intron-2. Like the human GWAS-marked intron-2 BCL11A enhancer, these sequences possessed a series of erythroid-specific DHSs. In addition, these sequences were decorated by H3K4me1 and H3K27ac, lacked H3K4me3 and H3K27me3, and occupied by both GATA1 and TAL1 in mouse erythroid chromatin (FIG. 8). Composite regulatory elements including a series of adjacent DHSs have been shown to be critical for gene expression at numerous loci, including among others the β-globin locus control region, α-globin multispecies conserved sequences, and IgH regulatory region (53-55). We observed species-specific unique features of the composite enhancer. For example, The inventors identified the conserved mouse sequences to each of the three human DHSs +62, +58 and +55, and found erythroid DNase I hypersensitivity at the +62 and +55 conserved sequences, however the +58 conserved sequences lacked DNase I hypersensitivity.

Figure 5A:
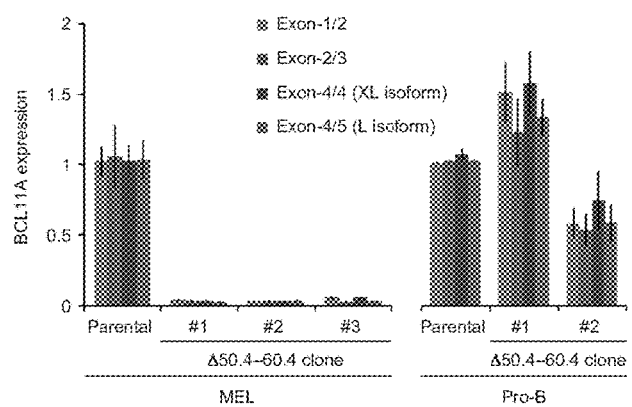
FIGS. 5A-5C show mouse erythroleukemia (MEL) cells and pro-B lymphoid cells transfected with two pairs of TALENs each designed to generate a DSB on either end of the orthologous 10 kb BCL11A intron-2 erythroid enhancer from +50.4-+60.4 kb. Clones (called Δ50.4-60.4) were isolated with biallelic deletion of the 10-kb segment.
Figure 10:
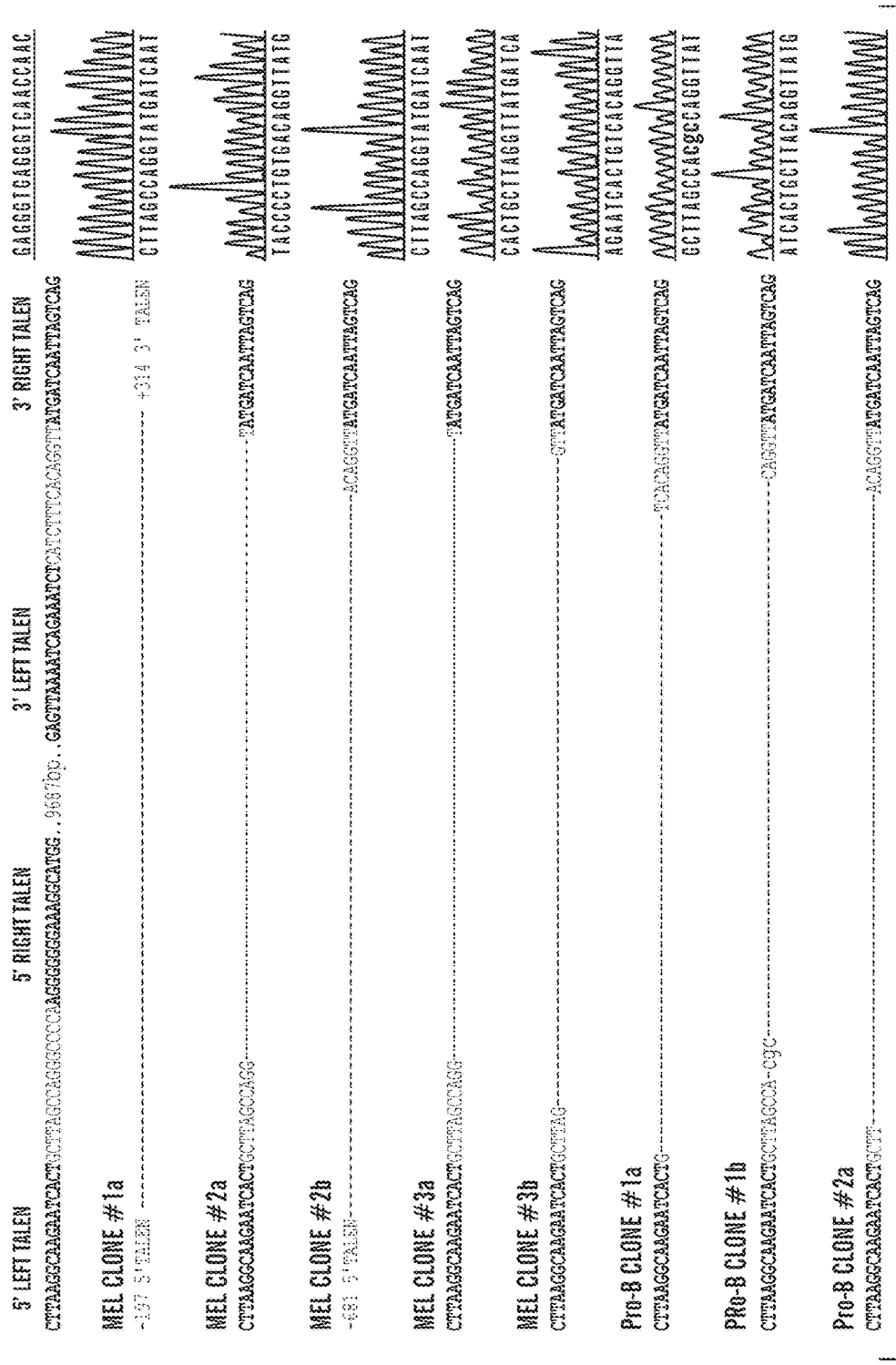
FIG. 10 shows Sanger sequencing of PCR products from Δ50.4-60.4 clones. 5' (+50.4) and 3' (+60.4) left and right TALEN recognition sequences with intervening spacers is shown. Some alleles showed evidence of end-joining directly from each digested spacer sequence whereas other alleles showed loss of hundreds of additional nucleotides. Only one allele each was isolated from MEL clone #1 and pro-B clone #2. Figure discloses SEQ ID NOS 199-215, top to bottom, respectively, in order of appearance.

PCR and Southern blotting verified excision of the +50.4-60.4 kb intronic segment of Bcl11a in three unique MEL clones and two unique pre-B lymphocyte clones (FIG. 9). Sanger-sequenced breakpoints were characteristic of TALEN-mediated cleavage with subsequent NHEJ repair (FIG. 10). Upon deletion of the intronic segment, we observed dramatic reduction in BCL11A transcript in the MEL cell clones by RT-qPCR, using primer pairs detecting exon junctions upstream, spanning or downstream of the deletion (FIG. 5A).

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

As used herein, the phrase "agent that binds the genomic DNA of the cell on chromosome 2 location 60,716,189-60,728,612" refers to small molecules, nucleic acids, proteins, peptides or oligonucleotides that can bind to the location within the genomic DNA (e.g., chromosome 2 location 60,716,189-60,728,612) and represses mRNA or protein expression of BCL11A in a cell by at least 20% compared to the mRNA or protein level of BCL11A in a cell not treated with such an agent. In one embodiment, the agent "interferes with BCL11A interactions with BCL11A binding partners," as that phrase is used herein.

As used herein, the term "small molecule" refers to a chemical agent including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

A "nucleic acid", as described herein, can be RNA or DNA, and can be single or double stranded, and can be selected, for example, from a group including: nucleic acid encoding a protein of interest, oligonucleotides, nucleic acid analogues, for example peptide-nucleic acid (PNA), pseudo-complementary PNA (pc-PNA), locked nucleic acid (LNA) etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc.

By "interferes with BCL11A interactions with BCL11A binding partners" is meant that the amount of interaction of BCL11A with the BCL11A binding partner is at least 5% lower in populations treated with a BCL11A inhibitor, than a comparable, control population, wherein no BCL11A inhibitor is present. It is preferred that the amount of interaction of BCL11A with the BCL11A binding partner in a BCL11A-inhibitor treated population is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population in which no BCL11A inhibitor is added. At a minimum, BCL11A interaction can be assayed by determining the amount of BCL11A binding to the BCL11A binding partner using techniques standard in the art, including, but not limited to, mass spectrometry, immunoprecipitation, or gel filtration assays. Alternatively, or in addition, BCL11A activity can be assayed by measuring fetal hemoglobin expression at the mRNA or protein level following treatment with a candidate BCL11A inhibitor.

In one embodiment, BCL11A activity is the interaction of BCL11A with its binding partners: GATA-1, FOG-1, components of the NuRD complex, matrin-3, MTA2 and RBBP7. Accordingly, any antibody or fragment thereof, small molecule, chemical or compound that can block this interaction is considered an inhibitor of BCL11A activity.

As used herein, the term "genetic engineered cell" refers to a cell that comprises at least one genetic modification, as that term is used herein.

As used herein, the term "genetic modification" refers to a disruption at the genomic level resulting in a decrease in BCL11A expression or activity in a cell. Exemplary genetic modifications can include deletions, frame shift mutations, point mutations, exon removal, removal of one or more DNAse 1-hypersensitive sites (DHS) (e.g., 2, 3, 4 or more DHS regions), etc.

By "inhibits BCL11A expression" is meant that the amount of expression of BCL11A is at least 5% lower in a cell or cell population treated with a DNA-targeting endonuclease, than a comparable, control cell or cell population, wherein no DNA-targeting endonuclease is present. It is preferred that the percentage of BCL11A expression in a treated population is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population in which no DNA-targeting endonuclease is added.

By "inhibits BCL11A activity" is meant that the amount of functional activity of BCL11A is at least 5% lower in a cell or cell population treated with the methods described herein, than a comparable, control cell or population, wherein no DNA-targeting endonuclease is present. It is preferred that the percentage of BCL11A activity in a BCL11A-inhibitor treated population is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population in which no DNA-targeting endonuclease is added. At a minimum, BCL11A activity can be assayed by determining the amount of BCL11A expression at the protein or mRNA levels, using techniques standard in the art. Alternatively, or in addition, BCL11A activity can be determined using a reporter construct, wherein the reporter construct is sensitive to BCL11A activity. The γ-globin locus sequence is recognizable by the nucleic acid-binding motif of the BCL11A construct.

In one embodiment, as used herein, the term "DNA targeting endonuclease" refers to an endonuclease that generates a double-stranded break at a desired position in the genome (e.g., chromosome 2 location 60,716,189-60,728,612) without producing undesired off-target double-stranded breaks. The DNA targeting endonuclease can be a naturally occurring endonuclease (e.g., a bacterial meganuclease) or it can be artificially generated (e.g., engineered meganucleases, TALENs, or ZFNs, among others).

In another embodiment, as used herein, the term "DNA targeting endonuclease" refers to an endonuclease that generates a single-stranded break or a "nick" or break on one strand of the DNA phosphate sugar backbone at a desired position in the genome (e.g., chromosome 2 location 60,716,189-60,728,612) without producing undesired off-target DNA stranded breaks.

As used herein, the term "vector" refers to a nucleic acid molecule capable of transporting another nucleic acid to which it has been linked. One type of vector is a "plasmid", which refers to a circular double stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors", or more simply "expression vectors." In general, expression vectors of utility in recombinant DNA techniques are often in the form of plasmids. In the present specification, "plasmid" and "vector" can be used interchangeably as the plasmid is the most commonly used form of vector. However, the methods and compositions described herein can include such other forms of expression vectors, such as viral vectors (e.g., replication defective retroviruses, lentiviruses, adenoviruses and adeno-associated viruses), which serve equivalent functions.

Within an expression vector, "operably linked" is intended to mean that the nucleotide sequence of interest is linked to the regulatory sequence(s) in a manner which allows for expression of the nucleotide sequence (e.g., in an in vitro transcription/translation system or in a target cell when the vector is introduced into the target cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). Furthermore, the DNA-targeting endonuclease can be delivered by way of a vector comprising a regulatory sequence to direct synthesis of the DNA-targeting endonuclease at specific intervals, or over a specific time period. It will be appreciated by those skilled in the art that the design of the expression vector can depend on such factors as the choice of the target cell, the level of expression desired, and the like.

As used herein the term "cleaves" generally refers to the generation of a double-stranded break in the DNA genome at a desired location.

As used herein, the term "effective amount of a composition comprising at least a DNA-targeting endonuclease" refers to an amount of a DNA-targeting endonuclease that yields sufficient endonuclease activity to generate a double-stranded break in the desired location of the genome. In one embodiment, the effective amount of a DNA-targeting endonuclease generates a double-stranded break at the desired genetic locus in at least 20% of the cells in a population contacted with the composition (e.g., at least 30%, at least 40%, at least 50%, at least 60%, at least 70%, at least 80%, at least 90%, at least 95%, at least 99%, or even 100% of the cells in the population comprise a genetic modification produced by the DNA-targeting endonuclease composition).

As used herein the term "increasing the fetal hemoglobin levels" in a cell indicates that fetal hemoglobin is at least 5% higher in populations treated with an agent that disrupts BCL11A mRNA or protein expression (e.g., a DNA-targeting endonuclease) by binding to genomic DNA at chromosome 2 location 60,716,189-60,728,612, than in a comparable, control population, wherein no agent is present. It is preferred that the percentage of fetal hemoglobin expression in a population treated with such an agent that binds the genomic DNA at chromosome 2 location 60,716,189-60,728,612 is at least 10% higher, at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher, or more than a control treated population of comparable size and culture conditions. The term "control treated population" is used herein to describe a population of cells that has been treated with identical media, viral induction, nucleic acid sequences, temperature, confluency, flask size, pH, etc., with the exception of the addition of the agent that binds genomic DNA at chromosome 2 location 60,716,189-60,728,612. In one embodiment, any method known in the art can be used to measure an increase in fetal hemoglobin expression, e. g. Western Blot analysis of fetal γ-globin protein and quantifying mRNA of fetal γ-globin.

The term "isolated cell" as used herein refers to a cell that has been removed from an organism in which it was originally found, or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched. In some embodiments, the isolated population is an isolated population of human hematopoietic progenitor cells, e.g., a substantially pure population of human hematopoietic progenitor cells as compared to a heterogeneous population of cells comprising human hematopoietic progenitor cells and cells from which the human hematopoietic progenitor cells were derived.

The term "substantially pure," with respect to a particular cell population, refers to a population of cells that is at least about 75%, preferably at least about 85%, more preferably at least about 90%, and most preferably at least about 95% pure, with respect to the cells making up a total cell population. That is, the terms "substantially pure" or "essentially purified," with regard to a population of hematopoietic progenitor cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not hematopoietic progenitor cells as defined by the terms herein.

As used herein, the term "treating" includes reducing or alleviating at least one adverse effect or symptom of a condition, disease or disorder. For example, the term "treating" and "treatment" refers to administering to a subject an effective amount of a composition, e.g., an effective amount of a composition comprising a population of hematopoietic progenitor cells so that the subject has a reduction in at least one symptom of the disease or an improvement in the disease, for example, beneficial or desired clinical results. For purposes of this disclosure, beneficial or desired clinical results include, but are not limited to, alleviation of one or more symptoms, diminishment of extent of disease, disease stabilization (e.g., not worsening), delay or slowing of disease progression, amelioration or palliation of the disease state, and remission (whether partial or total), whether detectable or undetectable. In some embodiments, treating can refer to prolonging survival as compared to expected survival if not receiving treatment. Thus, one of skill in the art realizes that a treatment can improve the disease condition, but may not be a complete cure for the disease. In some embodiments, treatment can include prophylaxis. However, in alternative embodiments, treatment does not include prophylaxis.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used with the methods described herein that will be effective in the treatment of a particular disorder or condition will depend on the nature of the disorder or condition, and can be determined by standard clinical techniques.

As used herein, "prevention" or "preventing," when used in reference to a disease, disorder or symptoms thereof, refers to a reduction in the likelihood that an individual will develop a disease or disorder, e.g., a hemoglobinopathy. The likelihood of developing a disease or disorder is reduced, for example, when an individual having one or more risk factors for a disease or disorder either fails to develop the disorder or develops such disease or disorder at a later time or with less severity, statistically speaking, relative to a population having the same risk factors and not receiving treatment as described herein. The failure to develop symptoms of a disease, or the development of reduced (e.g., by at least 10% on a clinically accepted scale for that disease or disorder) or delayed (e.g., by days, weeks, months or years) symptoms is considered effective prevention.

In connection with contacting a cell with a DNA-targeting endonuclease to decrease BCL11A expression, the phrase "increasing fetal hemoglobin levels in a cell" indicates that fetal hemoglobin in a cell or population of cells is at least 5% higher in the cell or population of cells treated with the DNA-targeting endonuclease, than a comparable, control population, wherein no DNA-targeting endonuclease is present. It is preferred that the fetal hemoglobin expression in a DNA-targeting endonuclease treated cell is at least 10% higher, at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher, or more than a comparable control treated population. The term "control treated population" is used herein to describe a population of cells that has been treated with identical media, viral induction, nucleic acid sequences, temperature, confluency, flask size, pH, etc., with the exception of the addition of the BCL11A inhibitor.

The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and bears. In some preferred embodiments, a mammal is a human.

Accordingly, in one embodiment, the mammal has been diagnosed with a hemoglobinopathy. In a further embodiment, the hemoglobinopathy is a β-hemoglobinopathy. In one preferred embodiment, the hemoglobinopathy is a sickle cell disease. As used herein, "sickle cell disease" can be sickle cell anemia, sickle-hemoglobin C disease (HbSC), sickle beta-plus-thalassaemia (HbS/β+), or sickle beta-zero-thalassaemia (HbS/β0). In another preferred embodiment, the hemoglobinopathy is a β-thalassemia.

As used herein, the term "hemoglobinopathy" means any defect in the structure or function of any hemoglobin of an individual, and includes defects in the primary, secondary, tertiary or quaternary structure of hemoglobin caused by any mutation, such as deletion mutations or substitution mutations in the coding regions of the β-globin gene, or mutations in, or deletions of, the promoters or enhancers of such genes that cause a reduction in the amount of hemoglobin produced as compared to a normal or standard condition. The term further includes any decrease in the amount or effectiveness of hemoglobin, whether normal or abnormal, caused by external factors such as disease, chemotherapy, toxins, poisons, or the like.

In one embodiment, the term "effective amount", as used herein, refers to the amount of a cell composition that is safe and sufficient to treat, lesson the likelihood of, or delay the development of a hemoglobinopathy. The amount can thus cure or result in amelioration of the symptoms of the hemoglobinopathy, slow the course of hemoglobinopathy disease progression, slow or inhibit a symptom of a hemoglobinopathy, slow or inhibit the establishment of secondary symptoms of a hemoglobinopathy or inhibit the development of a secondary symptom of a hemoglobinopathy. The effective amount for the treatment of the hemoglobinopathy depends on the type of hemoglobinopathy to be treated, the severity of the symptoms, the subject being treated, the age and general condition of the subject, the mode of administration and so forth. Thus, it is not possible or prudent to specify an exact "effective amount". However, for any given case, an appropriate "effective amount" can be determined by one of ordinary skill in the art using only routine experimentation.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Hemoglobinopathies

Fetal hemoglobin (HbF) is a tetramer of two adult α-globin polypeptides and two fetal β-like γ-globin polypeptides. During gestation, the duplicated γ-globin genes constitute the predominant genes transcribed from the β-globin locus. Following birth, γ-globin becomes progressively replaced by adult β-globin, a process referred to as the "fetal switch" (3). The molecular mechanisms underlying this switch have remained largely undefined and have been a subject of intense research. The developmental switch from production of predominantly fetal hemoglobin or HbF (α2γ2) to production of adult hemoglobin or HbA (α2γ2) begins at about 28 to 34 weeks of gestation and continues shortly after birth at which point HbA becomes predominant. This switch results primarily from decreased transcription of the gamma-globin genes and increased transcription of beta-globin genes. On average, the blood of a normal adult contains only about 2% HbF, though residual HbF levels have a variance of over 20 fold in healthy adults (Atweh, Semin. Hematol. 38(4):367-73 (2001)).

Hemoglobinopathies encompass a number of anemias of genetic origin in which there is a decreased production and/or increased destruction (hemolysis) of red blood cells (RBCs). These disorders also include genetic defects that result in the production of abnormal hemoglobins with a concomitant impaired ability to maintain oxygen concentration. Some such disorders involve the failure to produce normal β-globin in sufficient amounts, while others involve the failure to produce normal β-globin entirely. These disorders specifically associated with the β-globin protein are referred to generally as β-hemoglobinopathies. For example, β-thalassemias result from a partial or complete defect in the expression of the β-globin gene, leading to deficient or absent HbA. Sickle cell anemia results from a point mutation in the β-globin structural gene, leading to the production of an abnormal (sickled) hemoglobin (HbS). HbS RBCs are more fragile than normal RBCs and undergo hemolysis more readily, leading eventually to anemia (Atweh, Semin. Hematol. 38(4):367-73 (2001)). Moreover, the presence of a BCL11A genetic variant, HBS1L-MYB variation, ameliorates the clinical severity in beta-thalassemia. This variant has been shown to be associated with HbF levels. It has been shown that there is an odds ratio of 5 for having a less severe form of beta-thalassemia with the high-HbF variant (Galanello S. et al., 2009, Blood, in press).

The search for treatment aimed at reduction of globin chain imbalance in patients with β-hemoglobinopathies has focused on the pharmacologic manipulation of fetal hemoglobin (α2γ2; HbF). The important therapeutic potential of such approaches is suggested by observations of the mild phenotype of individuals with co-inheritance of both homozygous β-thalassemia and hereditary persistence of fetal hemoglobin (HPFH), as well as by those patients with homozygous β-thalassemia who synthesize no adult hemoglobin, but in whom a reduced requirement for transfusions is observed in the presence of increased concentrations of fetal hemoglobin. Furthermore, it has been observed that certain populations of adult patients with β chain abnormalities have higher than normal levels of fetal hemoglobin (HbF), and have been observed to have a milder clinical course of disease than patients with normal adult levels of HbF. For example, a group of Saudi Arabian sickle-cell anemia patients who express 20-30% HbF have only mild clinical manifestations of the disease (Pembrey, et al., Br. J. Haematol. 40: 415-429 (1978)). It is now accepted that β-hemoglobinopathies, such as sickle cell anemia and the β-thalassemias, are ameliorated by increased HbF production. (Reviewed in Jane and Cunningham Br. J. Haematol. 102: 415-422 (1998) and Bunn, N. Engl. J. Med. 328: 129-131 (1993)).

While the molecular mechanisms controlling the in vivo developmental switch from γ- to β-globin gene expression are currently unknown, there is accumulating evidence that external factors can influence γ-globin gene expression. The first group of compounds discovered having HbF reactivation activity were cytotoxic drugs. The ability to cause de novo synthesis of HbF by pharmacological manipulation was first shown using 5-azacytidine in experimental animals (DeSimone, Proc Natl Acad Sci USA. 79(14):4428-31 (1982)). Subsequent studies confirmed the ability of 5-azacytidine to increase HbF in patients with β-thalassemia and sickle cell disease (Ley, et al., N. Engl. J. Medicine, 307: 1469-1475 (1982), and Ley, et al., Blood 62: 370-380 (1983)). Additional experiments demonstrated that baboons treated with cytotoxic doses of arabinosylcytosine (ara-C) responded with striking elevations of F-reticulocytes (Papayannopoulou et al., Science. 224(4649):617-9 (1984)), and that treatment with hydroxyurea led to induction of γ-globin in monkeys or baboons (Letvin et. al., N Engl J Med. 310(14):869-73 (1984)).

The second group of compounds investigated for the ability to cause HbF reactivation activity was short chain fatty acids. The initial observation in fetal cord blood progenitor cells led to the discovery that γ-aminobutyric acid can act as a fetal hemoglobin inducer (Perrine et al., Biochem Biophys Res Commun.148(2):694-700 (1987)). Subsequent studies showed that butyrate stimulated globin production in adult baboons (Constantoulakis et al., Blood. Dec; 72(6):1961-7 (1988)), and it induced γ-globin in erythroid progenitors in adult animals or patients with sickle cell anemia (Perrine et al., Blood. 74(1):454-9 (1989)). Derivatives of short chain fatty acids such as phenylbutyrate (Dover et al., Br J Haematol. 88(3):555-61 (1994)) and valproic acid (Liakopoulou et al., 1: Blood. 186(8):3227-35 (1995)) also have been shown to induce HbF in vivo. Given the large number of short chain fatty acid analogs or derivatives of this family, there are a number of potential compounds of this family more potent than butyrate. Phenylacetic and phenylalkyl acids (Torkelson et al., Blood Cells Mol Dis. 22(2):150-8. (1996)), which were discovered during subsequent studies, were considered potential HbF inducers as they belonged to this family of compounds. Presently, however, the use of butyrate or its analogs in sickle cell anemia and β-thalassemia remains experimental and cannot be recommended for treatment outside of clinical trials.

Clinical trials aimed at reactivation of fetal hemoglobin synthesis in sickle cell anemia and β-thalassemia have included short term and long term administration of such compounds as 5-azacytidine, hydroxyurea, recombinant human erythropoietin, and butyric acid analogs, as well as combinations of these agents. Following these studies, hydroxyurea was used for induction of HbF in humans and later became the first and only drug approved by the Food and Drug Administration (FDA) for the treatment of hemoglobinopathies. However, varying drawbacks have contraindicated the long term use of such agents or therapies, including unwanted side effects and variability in patient responses. For example, while hydroxyurea stimulates HbF production and has been shown to clinically reduce sickling crisis, it is potentially limited by myelotoxicity and the risk of carcinogenesis. Potential long term carcinogenicity would also exist in 5-azacytidine-based therapies. Erythropoietin-based therapies have not proved consistent among a range of patient populations. The short half-lives of butyric acid in vivo have been viewed as a potential obstacle in adapting these compounds for use in therapeutic interventions. Furthermore, very high dosages of butyric acid are necessary for inducing γ-globin gene expression, requiring catheritization for continuous infusion of the compound. Moreover, these high dosages of butyric acid can be associated with neurotoxicity and multiorgan damage (Blau, et al., Blood 81: 529-537 (1993)). While even minimal increases in HbF levels are helpful in sickle cell disease, β-thalassemias require a much higher increase that is not reliably, or safely, achieved by any of the currently used agents (Olivieri, Seminars in Hematology 33: 24-42 (1996)).

Identifying natural regulators of HbF induction and production could provide a means to devise therapeutic interventions that overcome the various drawbacks of the compounds described above. Recent genome-wide association studies have yielded insights into the genetic basis of numerous complex diseases and traits (McCarthy et al., Nat Rev Genet 9, 356 (2008) and Manolio et. al. J Clin Invest 118, 1590 (2008)). However, in the vast majority of instances, the functional link between a genetic association and the underlying pathophysiology remains to be uncovered. The level of fetal hemoglobin (HbF) is inherited as a quantitative trait and clinically important, given its above-mentioned and well-characterized role in ameliorating the severity of the principal β-hemoglobinopathies, sickle cell disease and β-thalassemia (Nathan et. al., Nathan and Oski's hematology of infancy and childhood ed. 6th, pp. 2 v. (xiv, 1864, xli p.) 2003)). Two genome-wide association studies have identified three major loci containing a set of five common single nucleotide polymorphisms (SNPs) that account for ~20% of the variation in HbF levels (Lettre et al., Proc Natl Acad Sci USA (2008); Uda et al., Proc Natl Acad Sci USA 105, 1620 (2008); Menzel et al., Nat Genet 39, 1197 (2007)). Moreover, several of these variants appear to predict the clinical severity of sickle cell disease (Lettre et al., Proc Natl Acad Sci USA (2008)) and at least one of these SNPs may also affect clinical outcome in β-thalassemia (Uda et al., Proc Natl Acad Sci USA 105, 1620 (2008)). The SNP with the largest effect size, explaining over 10% of the variation in HbF, is located in the second intron of a gene on chromosome 2, BCL11A. Whereas BCL11A, a C2H2-type zinc finger transcription factor, has been investigated for its role in lymphocyte development (Liu et al., Nat Immunol 4, 525 (2003) and Liu et al., Mol Cancer 5, 18 (2006)), its role in red blood cell production or globin gene regulation has not been previously assessed.

At the onset of the recombinant DNA era, studies of globin gene structure provided a strong molecular foundation for interrogating the fetal globin switch. Considerable effort has focused on delineating the cis-elements within the β-globin locus necessary for proper regulation of the genes within the β-like globin cluster. These studies relied on naturally occurring mutations and deletions that dramatically influence HbF levels in adults, and have been complemented by generation of transgenic mice harboring portions of the cluster (Nathan et. al., Nathan and Oski's hematology of infancy and childhood ed. 6th, pp. 2 v. (xiv, 1864, xli p.) 2003) and G. Stamatoyannopoulos, Exp Hematol 33, 259 (2005)). Although the precise cis-elements required for globin switching remain ill-defined, findings in transgenic mice have strongly indicated that the γ-globin genes are autonomously silenced in the adult stage, a finding that is most compatible with the absence of fetal-stage specific activators or the presence of a stage-specific repressor. The results of recent genetic association studies provide candidate genes to interrogate for their involvement in control of the γ-globin genes, such as BCL11A.

Hematopoietic Progenitor Cells

In one embodiment, the hematopoietic progenitor cell is contacted ex vivo or in vitro. In a specific embodiment, the cell being contacted is a cell of the erythroid lineage. In one embodiment, the cell composition comprises cells having decreased BCL11A expression.

"Hematopoietic progenitor cell" as the term is used herein, refers to cells of a stem cell lineage that give rise to all the blood cell types including the myeloid (monocytes and macrophages, neutrophils, basophils, eosinophils, erythrocytes, megakaryocytes/platelets, dendritic cells), and the lymphoid lineages (T-cells, B-cells, NK-cells). A "cell of the erythroid lineage" indicates that the cell being contacted is a cell that undergoes erythropoeisis such that upon final differentiation it forms an erythrocyte or red blood cell (RBC). Such cells belong to one of three lineages, erythroid, lymphoid, and myeloid, originating from bone marrow haematopoietic progenitor cells. Upon exposure to specific growth factors and other components of the haematopoietic microenvironment, haematopoietic progenitor cells can mature through a series of intermediate differentiation cellular types, all intermediates of the erythroid lineage, into RBCs. Thus, cells of the "erythroid lineage", as the term is used herein, comprise hematopoietic progenitor cells, rubriblasts, prorubricytes, erythroblasts, metarubricytes, reticulocytes, and erythrocytes.

In some embodiment, the hematopoietic progenitor cell has at least one of the cell surface marker characteristic of hematopoietic progenitor cells: CD34+, CD59+, Thy1/CD90+,CD38lo/−, and C-kit/CD117+. Preferably, the hematopoietic progenitor cells have several of these markers.

In some embodiments, the hematopoietic progenitor cells of the erythroid lineage have the cell surface marker characteristic of the erythroid lineage: CD71 and Ter119.

Stem cells, such as hematopoietic progenitor cells, are capable of proliferation and giving rise to more progenitor cells having the ability to generate a large number of mother cells that can in turn give rise to differentiated or differentiable daughter cells. The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one embodiment, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Generally, "progenitor cells" have a cellular phenotype that is more primitive (i.e., is at an earlier step along a developmental pathway or progression than is a fully differentiated cell). Often, progenitor cells also have significant or very high proliferative potential. Progenitor cells can give rise to multiple distinct differentiated cell types or to a single differentiated cell type, depending on the developmental pathway and on the environment in which the cells develop and differentiate.

In the context of cell ontogeny, the adjective "differentiated", or "differentiating" is a relative term. A "differentiated cell" is a cell that has progressed further down the developmental pathway than the cell it is being compared with. Thus, stem cells can differentiate to lineage-restricted precursor cells (such as a hematopoietic progenitor cell), which in turn can differentiate into other types of precursor cells further down the pathway (such as an erthyrocyte precursor), and then to an end-stage differentiated cell, such as an erthyrocyte, which plays a characteristic role in a certain tissue type, and may or may not retain the capacity to proliferate further.

Induced Pluripotent Stem Cells

In some embodiments, the genetic engineered human cells described herein are derived from isolated pluripotent stem cells. An advantage of using iPSCs is that the cells can be derived from the same subject to which the progenitor cells are to be administered. That is, a somatic cell can be obtained from a subject, reprogrammed to an induced pluripotent stem cell, and then re-differentiated into a hematopoietic progenitor cell to be administered to the subject (e.g., autologous cells). Since the progenitors are essentially derived from an autologous source, the risk of engraftment rejection or allergic responses is reduced compared to the use of cells from another subject or group of subjects. In some embodiments, the hematopoeitic progenitors are derived from non-autologous sources. In addition, the use of iPSCs negates the need for cells obtained from an embryonic source. Thus, in one embodiment, the stem cells used in the disclosed methods are not embryonic stem cells.

Although differentiation is generally irreversible under physiological contexts, several methods have been recently developed to reprogram somatic cells to induced pluripotent stem cells. Exemplary methods are known to those of skill in the art and are described briefly herein below.

As used herein, the term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. Thus, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture.

The cell to be reprogrammed can be either partially or terminally differentiated prior to reprogramming. In some embodiments, reprogramming encompasses complete reversion of the differentiation state of a differentiated cell (e.g., a somatic cell) to a pluripotent state or a multipotent state. In some embodiments, reprogramming encompasses complete or partial reversion of the differentiation state of a differentiated cell (e.g., a somatic cell) to an undifferentiated cell (e.g., an embryonic-like cell). Reprogramming can result in expression of particular genes by the cells, the expression of which further contributes to reprogramming. In certain embodiments described herein, reprogramming of a differentiated cell (e.g., a somatic cell) causes the differentiated cell to assume an undifferentiated state (e.g., is an undifferentiated cell). The resulting cells are referred to as "reprogrammed cells," or "induced pluripotent stem cells (iPSCs or iPS cells)."

Reprogramming can involve alteration, e.g., reversal, of at least some of the heritable patterns of nucleic acid modification (e.g., methylation), chromatin condensation, epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent, although the compositions and methods described herein can also be of use for such purposes, in some embodiments.

The specific approach or method used to generate pluripotent stem cells from somatic cells (broadly referred to as "reprogramming") is not critical to the claimed invention. Thus, any method that re-programs a somatic cell to the pluripotent phenotype would be appropriate for use in the methods described herein.

Reprogramming methodologies for generating pluripotent cells using defined combinations of transcription factors have been described induced pluripotent stem cells. Yamanaka and Takahashi converted mouse somatic cells to ES cell-like cells with expanded developmental potential by the direct transduction of Oct4, Sox2, Klf4, and c-Myc (Takahashi and Yamanaka, 2006). iPSCs resemble ES cells as they restore the pluripotency-associated transcriptional circuitry and muc of the epigenetic landscape. In addition, mouse iPSCs satisfy all the standard assays for pluripotency: specifically, in vitro differentiation into cell types of the three germ layers, teratoma formation, contribution to chimeras, germline transmission (Maherali and Hochedlinger, 2008), and tetraploid complementation (Woltjen et al., 2009).

Subsequent studies have shown that human iPS cells can be obtained using similar transduction methods (Lowry et al., 2008; Park et al., 2008; Takahashi et al., 2007; Yu et al., 2007b), and the transcription factor trio, OCT4, SOX2, and NANOG, has been established as the core set of transcription factors that govern pluripotency (Jaenisch and Young, 2008). The production of iPS cells can be achieved by the introduction of nucleic acid sequences encoding stem cell-associated genes into an adult, somatic cell, historically using viral vectors.

iPS cells can be generated or derived from terminally differentiated somatic cells, as well as from adult stem cells, or somatic stem cells. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., Cell Stem Cell, 2010 Nov. 5; 7(5):618-30). Reprogramming can be achieved by introducing a combination of nucleic acids encoding stem cell-associated genes including, for example Oct-4 (also known as Oct-3/4 or Pouf51), Sox1, Sox2, Sox3, Sox 15, Sox 18, NANOG, Klf1, Klf2, Klf4, Klf5, NR5A2, c-Myc, 1-Myc, n-Myc, Rem2, Tert, and LIN28. In one embodiment, reprogramming using the methods and compositions described herein can further comprise introducing one or more of Oct-3/4, a member of the Sox family, a member of the Klf family, and a member of the Myc family to a somatic cell. In one embodiment, the methods and compositions described herein further comprise introducing one or more of each of Oct 4, Sox2, Nanog, c-MYC and Klf4 for reprogramming. As noted above, the exact method used for reprogramming is not necessarily critical to the methods and compositions described herein. However, where cells differentiated from the reprogrammed cells are to be used in, e.g., human therapy, in one embodiment the reprogramming is not effected by a method that alters the genome. Thus, in such embodiments, reprogramming is achieved, e.g., without the use of viral or plasmid vectors.

The efficiency of reprogramming (i.e., the number of reprogrammed cells) derived from a population of starting cells can be enhanced by the addition of various small molecules as shown by Shi, Y., et al (2008) *Cell-Stem Cell* 2:525-528, Huangfu, D., et al (2008) *Nature Biotechnology* 26(7):795-797, and Marson, A., et al (2008) *Cell-Stem Cell* 3:132-135. Thus, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide hydroxamic acid (SAHA), vitamin C, and trichostatin (TSA), among others.

Other non-limiting examples of reprogramming enhancing agents include: Suberoylanilide Hydroxamic Acid (SAHA (e.g., MK0683, vorinostat) and other hydroxamic acids), BML-210, Depudecin (e.g., (−)-Depudecin), HC Toxin, Nullscript (4-(1,3-Dioxo-1H,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (e.g., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-Cl-UCHA (e.g., 6-(3-chlorophenylureido) caproic hydroxamic acid), AOE (2-amino-8-oxo-9,10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Aton Pharma, Titan Pharmaceuticals, Schering A G, Pharmion, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbx15, Ecat1, Esg1, Eras, Gdf3, Fgf4, Cripto, Dax1, Zpf296, Slc2a3, Rex1, Utf1, and Nat1. In one embodiment, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. In some embodiments, detection does not involve only RT-PCR, but also includes detection of protein markers. Intracellular markers may be best identified via RT-PCR, while cell surface markers are readily identified, e.g., by immunocytochemistry.

The pluripotent stem cell character of isolated cells can be confirmed by tests evaluating the ability of the iPSCs to differentiate to cells of each of the three germ layers. As one example, teratoma formation in nude mice can be used to evaluate the pluripotent character of the isolated clones. The cells are introduced to nude mice and histology and/or immunohistochemistry is performed on a tumor arising from the cells. The growth of a tumor comprising cells from all three germ layers, for example, further indicates that the cells are pluripotent stem cells.

Somatic Cells for Reprogramming

Somatic cells, as that term is used herein, refer to any cells forming the body of an organism, excluding germline cells. Every cell type in the mammalian body—apart from the sperm and ova, the cells from which they are made (gametocytes) and undifferentiated stem cells—is a differentiated somatic cell. For example, internal organs, skin, bones, blood, and connective tissue are all made up of differentiated somatic cells.

Additional somatic cell types for use with the compositions and methods described herein include: a fibroblast (e.g., a primary fibroblast), a muscle cell (e.g., a myocyte), a cumulus cell, a neural cell, a mammary cell, an hepatocyte and a pancreatic islet cell. In some embodiments, the somatic cell is a primary cell line or is the progeny of a primary or secondary cell line. In some embodiments, the somatic cell is obtained from a human sample, e.g., a hair follicle, a blood sample, a biopsy (e.g., a skin biopsy or an adipose biopsy), a swab sample (e.g., an oral swab sample), and is thus a human somatic cell.

Some non-limiting examples of differentiated somatic cells include, but are not limited to, epithelial, endothelial, neuronal, adipose, cardiac, skeletal muscle, immune cells, hepatic, splenic, lung, circulating blood cells, gastrointestinal, renal, bone marrow, and pancreatic cells. In some embodiments, a somatic cell can be a primary cell isolated from any somatic tissue including, but not limited to brain, liver, gut, stomach, intestine, fat, muscle, uterus, skin, spleen, endocrine organ, bone, etc. Further, the somatic cell can be from any mammalian species, with non-limiting examples including a murine, bovine, simian, porcine, equine, ovine, or human cell. In some embodiments, the somatic cell is a human somatic cell.

When reprogrammed cells are used for generation of hematopoietic progenitor cells to be used in the therapeutic treatment of disease, it is desirable, but not required, to use somatic cells isolated from the patient being treated. For example, somatic cells involved in diseases, and somatic cells participating in therapeutic treatment of diseases and the like can be used. In some embodiments, a method for selecting the reprogrammed cells from a heterogeneous population comprising reprogrammed cells and somatic cells they were derived or generated from can be performed by any known means. For example, a drug resistance gene or the like, such as a selectable marker gene can be used to isolate the reprogrammed cells using the selectable marker as an index.

Reprogrammed somatic cells as disclosed herein can express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECATS, E-cadherin; β-III-tubulin; α-smooth muscle actin (α-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPAS/ECAT2; ECAT3; ECAT6; ECAT7; ECAT8; ECAT9; ECAT10; ECAT15-1; ECAT15-2; Fthl17; Sal14; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tcl1); DPPA3/Stella; DPPA4; other general markers for pluripotency, etc. Other markers can include Dnmt3L; Sox15; Stat3; Grb2; β-catenin, and Bmi1. Such cells can also be characterized by the down-regulation of markers characteristic of the somatic cell from which the induced pluripotent stem cell is derived.

Genome Editing and DNA-targeting Endonucleases

As used herein, the term "genome editing" refers to a reverse genetics method using artificially engineered nucleases to cut and create specific double-stranded breaks at a desired location(s) in the genome, which are then repaired by cellular endogenous processes such as, homologous recombination (HR), homology directed repair (HDR) and non-homologous end-joining (NHEJ). NHEJ directly joins the DNA ends in a double-stranded break, while HDR utilizes a homologous sequence as a template for regenerating the missing DNA sequence at the break point.

Genome editing cannot be performed using traditional restriction endonucleases since most restriction enzymes recognize a few base pairs on the DNA as their target and the probability is very high that the recognized base pair combination will be found in many locations across the genome resulting in multiple cuts (i.e., not limited to a desired location). To overcome this challenge and create site-specific double-stranded breaks, several distinct classes of nucleases have been discovered and bioengineered to date. These are the meganucleases, Zinc finger nucleases (ZFNs), Cas9/CRISPR system, and transcription-activator like effector nucleases (TALENs).

Meganucleases are commonly grouped into four families: the LAGLIDADG (SEQ ID NO: 1) family, the GIY-YIG family, the His-Cys box family and the HNH family. These families are characterized by structural motifs, which affect catalytic activity and recognition sequence. For instance, members of the LAGLIDADG (SEQ ID NO: 1) family are characterized by having either one or two copies of the conserved LAGLIDADG (SEQ ID NO: 1) motif (see Chevalier et al. (2001), Nucleic Acids Res. 29(18): 3757-3774). The LAGLIDADG (SEQ ID NO: 1) meganucleases with a single copy of the LAGLIDADG (SEQ ID NO: 1) motif form homodimers, whereas members with two copies of the LAGLIDADG (SEQ ID NO: 1) are found as monomers. Similarly, the GIY-YIG family members have a GIY-YIG module, which is 70-100 residues long and includes four or five conserved sequence motifs with four invariant residues, two of which are required for activity (see Van Roey et al. (2002), Nature Struct. Biol. 9: 806-811). The His-Cys box meganucleases are characterized by a highly conserved series of histidines and cysteines over a region encompassing several hundred amino acid residues (see Chevalier et al. (2001), Nucleic Acids Res. 29(18): 3757-3774). In the case of the NHN family, the members are defined by motifs containing two pairs of conserved histidines surrounded by asparagine residues (see Chevalier et al. (2001), Nucleic Acids Res. 29(18): 3757-3774). The four families of meganucleases are widely separated from one another with respect to conserved structural elements and, consequently, DNA recognition sequence specificity and catalytic activity.

Meganucleases are found commonly in microbial species and have the unique property of having very long recognition sequences (>14 bp) thus making them naturally very specific for cutting at a desired location. This can be exploited to make site-specific double-stranded breaks in genome editing. One of skill in the art can use these naturally occurring meganucleases, however the number of such naturally occurring meganucleases is limited. To overcome this challenge, mutagenesis and high throughput screening methods have been used to create meganuclease variants that recognize unique sequences. For example, various meganucleases have been fused to create hybrid enzymes that recognize a new sequence. Alternatively, DNA interacting amino acids of the meganuclease can be altered to design sequence specific meganucleases (see e.g., U.S. Pat. No. 8,021,867). Meganucleases can be designed using the methods described in e.g., Certo, M T et al. *Nature Methods* (2012) 9:073-975; U.S. Pat. Nos. 8,304,222; 8,021,867; 8,119,381; 8,124,369; 8,129,134; 8,133,697; 8,143,015; 8,143,016; 8,148,098; or 8,163,514, the contents of each are incorporated herein by reference in their entirety. Alternatively, meganucleases with site specific cutting characteristics can be obtained using commercially available technologies e.g., Precision BioSciences' Directed Nuclease Editor™ genome editing technology.

ZFNs and TALENs restriction endonuclease technology utilizes a non-specific DNA cutting enzyme which is linked to a specific DNA sequence recognizing peptide(s) such as zinc fingers and transcription activator-like effectors (TALEs). Typically, an endonuclease whose DNA recognition site and cleaving site are separate from each other is selected and the its cleaving portion is separated and then linked to a sequence recognizing peptide, thereby yielding an endonuclease with very high specificity for a desired sequence. An exemplary restriction enzyme with such properties is FokI. Additionally, FokI has the advantage of requiring dimerization to have nuclease activity and this means the specificity increases dramatically as each nuclease partner recognizes a unique DNA sequence. To enhance this effect, FokI nucleases have been engineered that can only function as heterodimers and have increased catalytic activity. The heterodimer functioning nucleases avoid the possibility of unwanted homodimer activity and thus increase specificity of the double-stranded break.

Although the nuclease portions of both ZFNs and TALENs have similar properties, the difference between these engineered nucleases is in their DNA recognition peptide. ZFNs rely on Cys2-His2 zinc fingers and TALENs on TALEs. Both of these DNA recognizing peptide domains have the characteristic that they are naturally found in combinations in their proteins. Cys2-His2 Zinc fingers typically happen in repeats that are 3 bp apart and are found in diverse combinations in a variety of nucleic acid interacting proteins such as transcription factors. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others. ZFNs for use with the methods and compositions described herein can be obtained commercially from e.g., Sangamo Biosciences™ (Richmond, Calif.).

It is contemplated herein that the Cas9/CRISPR system of genome editing be employed with the methods and compositions described herein. Clustered regularly interspaced short palindromic repeats (CRISPR)/CRISPR-associated (Cas) systems is useful for RNA-programmable genome editing (see e.g., Jinek, M. et al. *Science* (2012) 337(6096): 816-821).

Alternatively, genome editing can be performed using recombinant adeno-associated virus (rAAV) based genome engineering, which is a genome-editing platform centered around the use of rAAV vectors that enables insertion, deletion or substitution of DNA sequences into the genomes of live mammalian cells. The rAAV genome is a single-stranded deoxyribonucleic acid (ssDNA) molecule, either positive- or negative-sensed, which is about 4.7 kilobase long. These single-stranded DNA viral vectors have high transduction rates and have a unique property of stimulating endogenous homologous recombination in the absence of causing double strand DNA breaks in the genome. One of skill in the art can design a rAAV vector to target a desired genomic locus and perform both gross and/or subtle endogenous gene alterations in a cell, such as a deletion. rAAV genome editing has the advantage in that it targets a single allele and does not result in any off-target genomic alterations. rAAV genome editing technology is commercially available, for example, the rAAV GENESIS™ system from Horizon™ (Cambridge, UK).

Pharmaceutically Acceptable Carriers

The methods of administering human hematopoietic progenitors to a subject as described herein involve the use of therapeutic compositions comprising hematopoietic progenitor cells. Therapeutic compositions contain a physiologically tolerable carrier together with the cell composition and optionally at least one additional bioactive agent as described herein, dissolved or dispersed therein as an active ingredient. In a preferred embodiment, the therapeutic composition is not substantially immunogenic when administered to a mammal or human patient for therapeutic purposes, unless so desired.

In general, the hematopoietic progenitor cells described herein are administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the hematopoietic progenitor cells as described herein using routine experimentation.

A cell composition can also be emulsified or presented as a liposome composition, provided that the emulsification procedure does not adversely affect cell viability. The cells and any other active ingredient can be mixed with excipients which are pharmaceutically acceptable and compatible with the active ingredient and in amounts suitable for use in the therapeutic methods described herein.

Additional agents included in a cell composition as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions as described herein that is effective in the treatment of a particular disorder or condition will depend on the nature of the disorder or condition, and can be determined by standard clinical techniques.

Administration & Efficacy

As used herein, the terms "administering," "introducing" and "transplanting" are used interchangeably in the context of the placement of cells, e.g. hematopoietic progenitor cells, as described herein into a subject, by a method or route which results in at least partial localization of the introduced cells at a desired site, such as a site of injury or repair, such that a desired effect(s) is produced. The cells e.g. hematopoietic progenitor cells, or their differentiated progeny can be administered by any appropriate route which results in delivery to a desired location in the subject where at least a portion of the implanted cells or components of the cells remain viable. The period of viability of the cells after administration to a subject can be as short as a few hours, e.g., twenty-four hours, to a few days, to as long as several years, i.e., long-term engraftment. For example, in some embodiments of the aspects described herein, an effective amount of hematopoietic progenitor cells is administered via a systemic route of administration, such as an intraperitoneal or intravenous route.

When provided prophylactically, hematopoietic progenitor cells described herein can be administered to a subject in advance of any symptom of a hemoglobinopathy, e.g., prior to the switch from fetal γ-globin to predominantly β-globin. Accordingly, the prophylactic administration of a hematopoietic progenitor cell population serves to prevent a hemoglobinopathy, as disclosed herein.

When provided therapeutically, hematopoietic progenitor cells are provided at (or after) the onset of a symptom or indication of a hemoglobinopathy, e.g., upon the onset of sickle cell disease.

In some embodiments of the aspects described herein, the hematopoietic progenitor cell population being administered according to the methods described herein comprises allogeneic hematopoietic progenitor cells obtained from one or more donors. As used herein, "allogeneic" refers to a hematopoietic progenitor cell or biological samples comprising hematopoietic progenitor cells obtained from one or more different donors of the same species, where the genes at one or more loci are not identical. For example, a hematopoietic progenitor cell population being administered to a subject can be derived from umbilical cord blood obtained from one more unrelated donor subjects, or from one or more non-identical siblings. In some embodiments, syngeneic hematopoietic progenitor cell populations can be used, such as those obtained from genetically identical animals, or from identical twins. In other embodiments of this aspect, the hematopoietic progenitor cells are autologous cells; that is, the hematopoietic progenitor cells are obtained or isolated from a subject and administered to the same subject, i.e., the donor and recipient are the same.

For use in the various aspects described herein, an effective amount of hematopoietic progenitor cells, comprises at least $10^2$ hematopoietic progenitor cells, at least $5 \times 10^2$ hematopoietic progenitor cells, at least $10^3$ hematopoietic progenitor cells, at least $5 \times 10^3$ hematopoietic progenitor cells, at least $10^4$ hematopoietic progenitor cells, at least $5 \times 10^4$ hematopoietic progenitor cells, at least $10^5$ hematopoietic progenitor cells, at least $2 \times 10^5$ hematopoietic progenitor cells, at least $3 \times 10^5$ hematopoietic progenitor cells, at least $4 \times 10^5$ hematopoietic progenitor cells, at least $5 \times 10^5$ hematopoietic progenitor cells, at least $6 \times 10^5$ hematopoietic progenitor cells, at least $7 \times 10^5$ hematopoietic progenitor cells, at least $8 \times 10^5$ hematopoietic progenitor cells, at least $9 \times 10^5$ hematopoietic progenitor cells, at least $1 \times 10^6$ hematopoietic progenitor cells, at least $2 \times 10^6$ hematopoietic progenitor cells, at least $3 \times 10^6$ hematopoietic progenitor cells, at least $4 \times 10^6$ hematopoietic progenitor cells, at least $5 \times 10^6$ hematopoietic progenitor cells, at least $6 \times 10^6$ hematopoietic progenitor cells, at least $7 \times 10^6$ hematopoietic progenitor cells, at least $8 \times 10^6$ hematopoietic progenitor cells, at least $9 \times 10^6$ hematopoietic progenitor cells, or multiples thereof. The hematopoietic progenitor cells can be derived from one or more donors, or can be obtained from an autologous source. In some embodiments of the aspects described herein, the hematopoietic progenitor cells are expanded in culture prior to administration to a subject in need thereof.

In one embodiment, the term "effective amount" as used herein refers to the amount of a population of human hematopoietic progenitor cells or their progeny needed to alleviate at least one or more symptom of a hemoglobinopathy, and relates to a sufficient amount of a composition to provide the desired effect, e.g., treat a subject having a hemoglobinopathy. The term "therapeutically effective amount" therefore refers to an amount of hematopoietic progenitor cells or a composition comprising hematopoietic progenitor cells that is sufficient to promote a particular effect when administered to a typical subject, such as one who has or is at risk for a hemoglobinopathy. An effective amount as used herein would also include an amount sufficient to prevent or delay the development of a symptom of the disease, alter the course of a symptom disease (for example but not limited to, slow the progression of a symptom of the disease), or reverse a symptom of the disease. It is understood that for any given case, an appropriate "effective amount" can be determined by one of ordinary skill in the art using routine experimentation.

As used herein, "administered" refers to the delivery of a hematopoietic stem cell composition as described herein into a subject by a method or route which results in at least partial localization of the cell composition at a desired site. A cell composition can be administered by any appropriate route which results in effective treatment in the subject, i.e. administration results in delivery to a desired location in the subject where at least a portion of the composition delivered, i.e. at least $1 \times 10^4$ cells are delivered to the desired site for a period of time. Modes of administration include injection, infusion, instillation, or ingestion. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. For the delivery of cells, administration by injection or infusion is generally preferred.

In one embodiment, the cells as described herein are administered systemically. The phrases "systemic administration," "administered systemically", "peripheral administration" and "administered peripherally" as used herein refer to the administration of a population of hematopoietic progenitor cells other than directly into a target site, tissue, or organ, such that it enters, instead, the subject's circulatory system and, thus, is subject to metabolism and other like processes.

The efficacy of a treatment comprising a composition as described herein for the treatment of a hemoglobinopathy can be determined by the skilled clinician. However, a treatment is considered "effective treatment," as the term is used herein, if any one or all of the signs or symptoms of, as but one example, levels of fetal β-globin are altered in a beneficial manner, other clinically accepted symptoms or markers of disease are improved or ameliorated, e.g., by at least 10% following treatment with an inhibitor. Efficacy can also be measured by failure of an individual to worsen as assessed by hospitalization or need for medical interventions (e.g., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of sepsis; or (2) relieving the disease, e.g., causing regression of symptoms; and (3) preventing or reducing the likelihood of the development of infection or sepsis.

The treatment according to the present invention ameliorates one or more symptoms associated with a β-globin disorder by increasing the amount of fetal hemoglobin in the individual. Symptoms typically associated with a hemoglobinopathy, include for example, anemia, tissue hypoxia, organ dysfunction, abnormal hematocrit values, ineffective erythropoiesis, abnormal reticulocyte (erythrocyte) count, abnormal iron load, the presence of ring sideroblasts, splenomegaly, hepatomegaly, impaired peripheral blood flow, dyspnea, increased hemolysis, jaundice, anemic pain crises, acute chest syndrome, splenic sequestration, priapism, stroke, hand-foot syndrome, and pain such as angina pectoris.

In one embodiment, the hematopoietic progenitor cell is contacted ex vivo or in vitro with a DNA targeting endonuclease, and the cell or its progeny is administered to the mammal (e.g., human). In a further embodiment, the hematopoietic progenitor cell is a cell of the erythroid lineage. In one embodiment, a composition comprising a hematopoietic progenitor cell that was previously contacted with a DNA-targeting endonuclease and a pharmaceutically acceptable carrier and is administered to a mammal.

In one embodiment, any method known in the art can be used to measure an increase in fetal hemoglobin expression, e.g., Western Blot analysis of fetal hemoglobin protein and quantifying mRNA of fetal γ-globin.

In one embodiment, the hematopoietic progenitor cell is contacted with a DNA-targeting endonuclease in vitro, or ex vivo. In one embodiment, the cell is of human origin (e.g., an autologous or heterologous cell). In one embodiment, the composition causes an increase in fetal hemoglobin expression.

The present invention can be defined in any of the following alphabetized paragraphs:

[A] A method for producing a progenitor cell having decreased BCL11A mRNA or protein expression, the method comprising contacting an isolated progenitor cell with an agent that binds the genomic DNA of the cell on chromosome 2 location 60,716,189-60,728,612 (according to UCSC Genome Browser hg 19 human genome assembly), thereby reducing the mRNA or protein expression of BCL11A.

[B] A method for producing an isolated genetic engineered human cell having at least one genetic modification comprising contacting an isolated cell with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 causing at least one genetic modification therein.

[C] The method of paragraph [A] or [B], wherein the isolated progenitor cell or isolated cell is a hematopoietic progenitor cell.

[D] The method of paragraph [C], wherein the hematopoietic progenitor is a cell of the erythroid lineage.

[E] The method of paragraph [A] or [B], wherein the isolated progenitor cell or isolated cell is an induced pluripotent stem cell.

[F] The method of paragraph [C], wherein the hematopoietic progenitor cell is contacted ex vivo or in vitro.

[G] The method of any one of paragraphs [A]-[F], wherein the at least one genetic modification is a deletion.

[H] The method of paragraph [G], wherein the deletion removes the entire region between chromosome 2 location 60,716,189-60,728,612 or removes a portion of the region resulting in disruption of one or more DNAse 1-hypersensitive sites (DHS).

[I] An isolated genetic engineered human cell having at least one genetic modification on chromosome 2 location 60,716,189-60,728,612 according to paragraphs [B]-[H].

[J] A composition comprising isolated genetic engineered human cells of paragraph [I].

[K] A method of increasing fetal hemoglobin levels in a cell, the method comprising the steps of: contacting an isolated cell with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 causing at least one genetic modification therein, whereby fetal hemoglobin expression is increased in said cell, or its progeny, relative to said cell prior to said contacting.

[L] The method of paragraph [K], wherein the isolated cell is a hematopoietic progenitor cell.

[M] The method of paragraph [K] or [L], wherein the hematopoietic progenitor cell is a cell of the erythroid lineage.

[N] The method of paragraph [K], wherein the isolated cell is an induced pluripotent stem cell.

[O] The method of paragraph [L] or [M], wherein the hematopoietic progenitor cell is contacted ex vivo or in vitro.

[P] The method of any one of paragraphs [K]-[O], wherein the at least one genetic modification is a deletion.

[Q] The method of paragraph [P], wherein the deletion removes the entire region between chromosome 2 location 60,716,189-60,728,612 or removes a portion of the region resulting in disruption of one or more DNAse 1-hypersensitive sites (DHS).

[R] A method for increasing fetal hemoglobin levels in a mammal in need thereof, the method comprising the steps of contacting an isolated hematopoietic progenitor cell in said mammal with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 causing at least one genetic modification therein, whereby fetal hemoglobin expression is increased in said mammal, relative to expression prior to the contacting.

This invention is further illustrated by the following example which should not be construed as limiting. The contents of all references cited throughout this application, as well as the figures and table are incorporated herein by reference.

EXAMPLE

The inventors have discovered and characterized regulatory elements of the BCL11A gene that are critical for its expression in erythroid lineage cells. Common genetic variants within these sequences are associated with fetal hemoglobin level and beta-globin disorder severity. These sequences comprise distal regulatory elements with an enhancer chromatin signature, possessing accessible chromatin, active histone marks, and occupancy by erythroid transcription factors. These elements interact with the BCL11A promoter and promote gene expression in erythroid cells but not other lineages that express BCL11A such as B-lymphocytes. These regulatory elements can be targeted for therapeutic purposes to achieve BCL11A inhibition and fetal hemoglobin reinduction. This can be achieved by mechanisms not limited to genome editing, nucleic acid or protein binding, and epigenetic modification. Advantages of this method include: disruption of a physiologic regulator of fetal hemoglobin level resulting in increased gamma-globin production and reduced beta-globin production; minimal effect on overall globin output or on red blood cell production or function; limitation of impact on cells outside of the erythroid lineage thus reducing potential toxicity.

Materials and Methods

Cell Culture

Human CD34+ cells from mobilized peripheral blood of healthy donors were obtained from Centers of Excellence in Molecular Hematology at Yale University, New Haven, Connecticut and Fred Hutchinson Cancer Research Center, Seattle, Wash. The cells were subject to ex vivo erythroid maturation with a two-phase serum-free liquid culture protocol as previously described (39). Peripheral blood mononuclear cells (PBMCs) were obtained from healthy donors from Boston Children's Hospital. Erythroid differentiation from PBMCs was performed as previously described (40). Mouse erythroleukemia (MEL) cells and 293T cells were cultured as previously described (39). Stably v-Abl transformed pre-B lymphocyte murine cells (derived as described (41)) were cultured in RPMI plus 2% penicillin-streptomycin, 15% FCS, 2% HEPES, 1% non-essential amino acids, 1% sodium pyruvate, 1% L-glutamine and 100 µM β-mercaptoethanol.

ChIP and DNase I Sensitivity

Chromatin immunoprecipitation and massively parallel sequencing were performed as described (39). The following antibodies were used: H3K27me3 (Millipore, 07-449), H3K4me3 (Millipore, 04-745), H3K4me1 (Abcam, ab8895), H3K27ac (Abcam, ab4729), RNA Polymerase II (PolII, Santa Cruz, sc-899), GATA1 (Abcam, ab11852) and TAL1 (Santa Cruz, sc-12984). DNase I cleavage density performed and analyzed as previously described (42). For ChIP-qPCR, relative enrichment was determined by comparing amplification of ChIP material to 1% input chromatin by the ΔCt method. Loci previously reported to be occupied and non-occupied by GATA1 and TAL1 were used as positive and negative controls respectively (39).

Chromosome Conformation Capture (3C)

3C assay was performed as previously described (39) except as below. Nuclei from formaldehyde cross-linked primary human erythroid precursors were digested with HindIII prior to ligation and reversal of cross-links. Quantitative real-time PCR was performed using iQ SYBR Green Supermix (Bio-Rad, 170-8880). A fragment containing the BCL11A promoter was used as the anchor region. To correct for amplification efficiency of different primers, a control template was prepared by digesting and ligating an equimolar mixture of two bacterial artificial chromosomes (BACs) comprising the complete human BCL11A locus (RP11-606L8 and RP11-139C22) and one the human β-globin cluster (CTD-3055E11). An interaction between fragments in HS1/HS2 and HS3 of the human β-globin locus control region (LCR) served as a positive control. Interaction frequency was expressed as amplification relative to the known LCR interaction, normalized to the BAC control template.

Fine-mapping BCL11A Locus

Markers (all coordinates hg19) were selected from within the three BCL11A intron-2 DHSs +62 (chr2:60,717,492-60,718,860), +58 (chr2:60,721,411-60,722,674) and +55 (chr2:60,724,802-60,726,084). 21 markers were identified from the 1000 Genomes Project database using the North European (CEU), Nigerian (YRI) and African-American (ASW) reference populations (Table S1). 38 additional variants were present in dbSNP135 (Table 2). The inventors sequenced by Sanger chemistry the three DHS intervals in the DNA of 52 and 36 sickle cell disease (SCD) patients from the CSSCD cohort with high (>8%) and low (<2%) HbF levels, respectively. From this sequencing effort, seven novel sequence variants were identified (Table 3). Because most markers cluster in small genomic intervals, it was not possible to design genotyping assays for some of them. Of 66 non-redundant variants identified in the three DHSs, genotyping assays for 40 markers were performed in 1,263 participants from the CSSCD, an African-American SCD cohort for which genomic DNA (gDNA) is available and HbF levels are known (21). Markers were genotyped using the Sequenom iPLEX platform. Individuals and DNA sequence variants with a genotyping success rate<90% were excluded. Overall genotype concordance estimated from triplicates was 100%. SNPs passing quality control (QC; n=38) are listed in Tables 2 and 3, and shown schematically in FIGS. 11A and 11B below the three DHSs. A substantial fraction of the genotyped SNPs are rare in the reference populations so not surprisingly monomorphic in the CSSCD (n=18). After QC, 1,178 individuals and 20 polymorphic SNPs remained for the analysis. HbF levels were modeled as previously described (9, 43). Association and conditional analyses of single variants (MAF>1%) were performed with PLINK (44) using linear regression under an additive genetic model. Analysis of common variants (MAF>1%) revealed that rs1427407 in DHS +62 had the strongest association to HbF level (P=7.23×10-50; FIGS. 11A and 3B). Conditional analysis demonstrated that after conditioning on rs1427407 and rs7606173, no more SNPs were significant (FIG. 3B). Adjusting for principal components (PCs) on 855 individuals for whom genome-wide genotyping data was available to account for admixture and other confounders yielded similar results.

For rare and low-frequency variants (MAF<5%), the inventors performed set-based analyses using each of the three DHSs +62, +58 and +55 as the testing unit. For these analyses, we used the sequence kernel association test (SKAT-O) program (45) with default parameters. The inventors selected the 5% threshold for MAF in order to maximize statistical power given our limited sample size, but note that markers with a MAF between 1% and 5% were also analyzed in the single variant analyses presented above. This variant overlap is accounted for using conditional analyses with the common variants independently associated with HbF levels. Two sets were found to be statistically significant, namely DHS +62 and DHS +55, but after conditioning on rs1427407 and rs7606173, results were no longer statistically significant, suggesting weak LD between the rare/low-frequency variants and the common SNPs (Table 5). The inventors did not find evidence that rare and low-frequency sequence variants within the BCL11A DHSs influence HbF levels in SCD subjects, despite Sanger re-sequencing these DHSs in 88 subjects with extreme HbF phenotype.

The rs1427407-rs7606173 haplotype frequencies in CSSCD are: T-G 24.5%, T-C 0.085%, G-C 42.3%, G-G 33.1%. The mean HbF level is 4.05% (SD 3.10) in 213 rs1427407-rs7606173 G-C individuals, 7.08% (SD 4.50) in 254 rs1427407-rs7606173 T-G/G-C heterozygotes and 11.21% (SD 4.37) in 60 rs1427407-rs7606173 T-G individuals (FIG. 3C). For comparisons of HbF levels between genotypes, the P-values were determined by one-tailed student t-tests.

Molecular Haplotyping

For two heterozygous SNPs on the same chromosome, there are two possible phases: A-B/a-b (model 1) and A-b/a-B (model 2). For SNPs within the 12-kb BCL11A intron-2 fragment +52.0-64.4 kb, phase was determined by cloning PCR products and determining co-distribution of SNP alleles. To determine phase of rs7569946 and rs1427407 alleles (separated by 30.1 kb on chromosome 2), emulsion fusion PCR was performed as previously described (24, 25) with minor modification. Fusion PCR brings two regions of interest, from separate parts of the same chromosome, together into a single product. By carrying out the reaction in emulsion with aqueous microdroplets surrounded by oil, the preponderance of amplicons are derived from a single template molecule. Genomic DNA from individuals known to be doubly heterozygous for rs7569946 and rs1427407 served as template in the following 100 μl reaction (with final concentrations listed): KOD Hot Start DNA Polymerase (14 U, Novagen, 71086), KOD buffer (1×), MgSO4 (1.5 mM), dNTPs (0.2 mM each), rs7569946-F and r51427407-R primers (1 μM each), rs7569946-R primer (30 nM), rs7569946-R-revcomp-r51427407-F bridging inner primer (30 nM), gDNA (200 ng). The 100 μl aqueous reaction was added dropwise with stirring to 200 μl oil phase to create an emulsion. Two 125 μl aliquots of emulsion were amplified under the following conditions: 95 degrees 2 minutes; 45 cycles of 95 degrees 20 seconds, 60 degrees 10 seconds, 70 degrees 30 seconds; 70 degrees 2 minutes. Hexane extracted fusion PCR product was subject to nested PCR in 25 μl as follows: KOD Hot Start DNA Polymerase (0.5 U), KOD buffer (1×), MgSO4 (1.5 mM), dNTPs (0.2 mM each), rs7569946-nested-F and rs1427407-nested-R primers (300 nM each), extracted fusion PCR product (75 nl); 95 degrees 2 minutes; 35 cycles of 95 degrees 20 seconds, 60 degrees 10 seconds, 70 degrees 30 seconds; 70 degrees 2 minutes. The nested product was confirmed by agarose gel electrophoresis to constitute a single band of expected size. The purified product was cloned with the Zero Blunt PCR Cloning kit (Life Technologies, K2700-20). The Sanger sequencing of fusion amplicons enumerated clones of 4 possible sequences: A-B, a-b, A-b and a-B. The likelihood of each phase was calculated based on a multinomial distribution assumption (Table 6). The likelihood ratio for the two configurations was calculated as a measure for the statistical significance of the data fitting haplotype model 1 (as compared to model 2). A ratio approaching infinity suggests model 1, a ratio of 1 suggests equipoise and a ratio approaching zero suggests model 2.

Pyrosequencing

Healthy CD34+ cell donors were screened to identify five donors heterozygous for rs1427407. These CD34+ cells were subject to ex vivo erythroid differentiation. Chromatin was isolated and ChIP performed with GATA1 and TAL1 antibodies. Input chromatin as compared to GATA1 or TAL1 precipitated material was subject to pyrosequencing to determine allelic balance of rs1427407. Healthy CD34+ donors were screened to identify three donors heterozygous for the rs1427407-rs7606173 G-C/T-G haplotype. These CD34+ cells were subject to ex vivo erythroid differentiation. Complementary DNA (cDNA) and gDNA were subject to pyrosequencing to determine allelic balance of rs7569946. PCR conditions as follows: 2X HotStarTaq master mix (QIAGEN, 203443), $MgCl_2$ (final concentration 3 mM), template DNA (0.1-1 ng) and SNP-specific forward and reverse-biotinylated primers (200 nM each). PCR cycling conditions were: 94° C. 15 min; 45 cycles of 94° C. 30 s; 60° C. 30 s; 72° C. 30 s; 72° C. 5 min. One primer of each pair was biotinylated. The PCR product strand containing the biotinylated primer was bound to streptavidin beads and combined with a specific sequencing primer. The primed single stranded DNA was sequenced and genotype analyzed using the Pyrosequencing PSQ96 HS System (QIAGEN Pyrosequencing) following the manufacturer's instructions.

Transgenic Mice

The enhancer reporter construct pWHERE-Dest was obtained from Dr. William Pu. Modified from pWHERE (Invitrogen, pwhere) as previously described (46), the construct has murine H19 insulators flanking a CpG-free lacZ variant driven by a minimal Hsp68 minimal promoter with a Gateway destination cassette at the upstream MCS Enhancer fragments were amplified from mouse gDNA, recombined into pDONR221 vector (Invitrogen, 12536-017) by BP clonase (Invitrogen, 11789020) and recombined into pWHERE-Dest vector with LR clonase (Invitrogen, 11791020). Plasmids were digested with PacI to remove vector backbone. The lacZ enhancer reporter fragments were purified by gel electroelution and then concentrated using Wizard DNA Clean-Up System (Promega, A7280). Transgenic mice were generated by pronuclear injection to FVB fertilized eggs. Approximately 10 ng/μl of DNA solution was used for series of injections. CD-1 females were used as recipients for injected embryos. 10.5 to 14.5 dpc embryos were dissected from surrogate mothers with whole-mount and tissue X-gal staining performed as previously described (47). X-gal stained cytospins were counterstained with Nuclear Fast Red (Vector Laboratories, H-3403). Tails used for PCR genotyping. Animal procedures were approved by the Children's Hospital Instititutional Animal Care and Use Committee.

Human Erythroid Precursor Enhancer Assay

Genomic DNA fragments containing putative enhancer elements were cloned into pLVX-Puro (Clontech, 632164) upstream of a minimal TK promoter and GFP reporter gene as described (39). 293T cells were transfected with FuGene 6 reagent (Promega, E2691) according to manufacturer's protocol. The media was changed after 24 hours to SFEM medium supplied with 2% penicillin-streptomycin, and after 36 hours, supernatant was collected and filtered. CD34+ cell-derived erythroid cultures were transduced with lentivirus on expansion days 4 and 5 by spin-infection as previously described (39). Cells were resuspended in erythroid differentiation media 24 hours after the second infection. Selection with puromycin 1 μg/ml commenced 48 hours after infection. Transduced cells were analyzed after five days in differentiation media by flow cytometry for GFP mean fluorescence intensity.

Flow Cytometry

Live cells were gated by exclusion of 7-aminoactinomycin D (7-AAD, BD Pharmingen, 559925). Bone marrow (for erythroblast) and spleen (for lymphocyte) suspensions were isolated from young adult transgenic mice. Following hypotonic lysis of mature red blood cells, live cells (7-AAD-) sorted based on staining with CD71-biotin (BD, 557416), streptavidin-APC (BD, 554067), Ter-119-PE (BD, 553673), CD19-APC (BD, 550992) or CD3-PE (BD, 100308). CD71+Ter119+, CD19+ and CD3+ sorted populations used for cytospin and RNA isolation.

TALEN-Mediated Chromosomal Deletion

Transcription activator-like effector nucleases (TALENs) were designed to generate cleavages at mouse Bcl11a intron-2 at sites +50.4 kb (termed 5' site) and +60.4 kb (3' site) relative to the TSS. The TALENs recognize the following sequences: CTTAAGGCAAGAATCACT (SEQ ID NO: 2) (5' left), CCATGCCTTTCCCCCCCT (SEQ ID NO: 3) (5' right), GAGTTAAAATCAGAAATCT (SEQ ID NO: 4) (3' left), CTGACTAATTGATCAT (SEQ ID NO: 5) (3' right). TALENs were synthesized with Golden Gate cloning (48) using the NN RVD to recognize G. The synthesized DNA binding domains were cloned into pcDNA3.1 (Invitrogen, V790-20) with the FokI nuclease domain, A152 N-terminal domain and +63 C-terminal domain previously described (49). 2.5 μg of each of the four TALEN plasmids with 0.5 μg pmaxGFP (Lonza) were delivered to $2 \times 10^6$ MEL or pre-B cells by electroporation per manufacturer's protocol (Lonza, VCA-1005). GFP-positive cells were sorted by flow cytometry after 48 hours. Cells seeded by limiting dilution in 96-well plates to isolate individual clones. Clones screened by PCR of gDNA to detect the amplification of a short product from upstream of the 5' site and downstream of the 3' site indicating deletion of the intervening segment. Monoallelic deleted clones were subject to a second round of TALEN-mediated deletion to obtain biallelic deleted clones. Clones with biallelic deletion were identified by detecting absence of amplification from within the deleted fragment. Deletion frequency was approximately one in 50 alleles. Deletion was validated with Southern blotting. Genomic DNA was digested with BmtI; a 561-bp probe (amplified from gDNA upstream of the 5' site) hybridizes to a 3.6 kb fragment from the wild-type allele and a 8.9 kb fragment from the Δ50.4-60.4 deleted allele.

RT-qPCR and Immunoblotting

RNA isolation with RNeasy columns (Qiagen, 74106), reverse transcription with iScript cDNA synthesis kit (Bio-Rad, 170-8890), qPCR with iQ SYBR Green Supermix (Bio-Rad, 170-8880) and immunoblotting performed as described (39). For the mouse β-globin cluster genes, a common primer pair recognizes the adult β-globins β2 and β1 while independent primers recognize the embryonic β-globins εy and βH1. The following antibodies were used for immunoblotting: BCL11A (Abcam, ab19487), GAPDH (Santa Cruz, sc-25778).

Results

Genome-wide association studies (GWAS) have ascertained numerous common genetic variants associated with traits, frequently localized to regulatory DNA. The hypothesis that regulatory variation may account for substantial heritability has undergone scarce experimental evaluation. Here the inventors show that a common genetic variation at BCL11A associated with fetal hemoglobin (HbF) level indicates noncoding sequences decorated by an erythroid enhancer chromatin signature. Fine mapping within this putative regulatory DNA reveals a motif-disrupting common variant associated with reduced transcription factor binding, diminished BCL11A expression, and elevated HbF. The surrounding sequences function in vivo as a developmental stage-specific lineage-restricted enhancer. By genome engineering, it was shown that this enhancer is required for erythroid BCL11A expression yet dispensable outside the erythroid lineage. These results illustrate how GWAS can highlight functional variants of modest impact within causal elements essential for appropriate gene expression. The GWAS-marked BCL11A enhancer represents a favorable therapeutic target for the β-globin disorders.

GWAS have been tremendously successful in identifying many thousands of common single nucleotide polymorphisms (SNPs) associated with human traits and diseases. However, advancing from genetic association to causal biologic process has often been difficult. Challenges include the large number of correlated variants that may be associated with individual traits (owing to linkage disequilibrium (LD)), the modest effect size of many variant-trait associations, and the location of many associated variants in the noncoding genome. Recent genome-scale chromatin mapping studies have highlighted the enrichment of GWAS variants in regulatory DNA elements, suggesting many causal variants may affect gene regulation. Nonetheless, few examples confirming the significance of causal variants or elements have been experimentally demonstrated.

The GWAS of HbF level have been particularly striking. Genetic variation at just three loci (HBB, HBS1L-MYB, and BCL11A) accounts for up to 50% of the heritable variation in HbF level. The same variants are also associated with the clinical severity of the major β-globinopathies sickle cell disease and β-thalassemia, perhaps not surprisingly since HbF is a major modifier of these disorders. Work from the inventor's laboratory and others have validated that BCL11A is a direct regulator of HbF levels. BCL11A is a transcriptional repressor that resides within multiprotein complexes occupying the β-globin gene cluster. While constitutive BCL11A deficiency results in embryonic lethality and impaired lymphocyte development, erythroid-specific deficiency of BCL11A counteracts developmental silencing of embryonic and fetal globin genes and is sufficient to rescue the hematologic and pathologic features of sickle cell disease in mouse models. Therefore, BCL11A has emerged as a novel therapeutic target for the β-globin disorders. Understanding the consequences of impaired BCL11A is imperative. Human coding variants of BCL11A have not been described despite large-scale resequencing efforts. The BCL11A variants associated with HbF levels reside in noncoding regions of BCL11A. To further understand how common genetic variation impacts BCL11A, HbF level, and β-globin disorder severity, the role of HbF-associated variants was investigated in detail.

Trait-Associated Variants Near Erythroid Enhancers

Figure 1B:
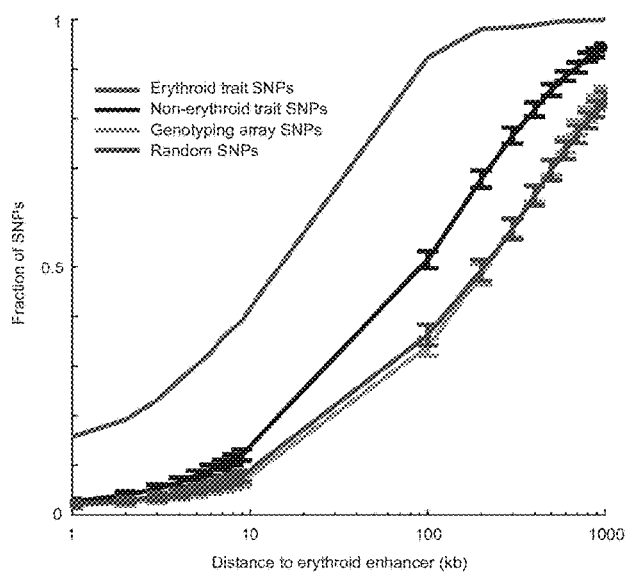
FIG. 1B is a graph plotting the cumulative distribution of the distances of the 636 erythroid trait-associated SNPs with respect to nearest erythroid enhancer. Erythroid enhancers were defined by sequences more than 2 kb from the TSSs of Refseq-annotated genes with DNase I hypersensitivity, presence of H3K4me1, either H3K27ac or H3K9ac, and absence of H3K4me3 and H3K27me3. The distance of mean±SD of 50 sets of 636 randomly permuted non-erythroid trait-associated SNPs (from GWAS database), SNPs from the Affy 6.0 genotyping array, or random SNPs were also plotted.

Numerous GWAS as well as follow-up fine-mapping studies have been performed of erythroid traits (including phenotypes such as erythrocyte number and volume, hemoglobin concentration, and HbF level), identifying 636 trait-associated SNPs at genome-wide significance ($p<5e^{-8}$). These SNPs are enriched in promoters and coding regions as compared to random SNPs (FIG. 1). Still the majority of the SNPs reside elsewhere in the genome. A global chromatin profiling of primary human erythroid precursors was performed, which identified an extensive set of distal erythroid enhancers defined by characteristic histone modifications and DNase I hypersensitivity. A strong colocalization of erythroid GWAS SNPs with enhancers was observed as compared to non-erythroid trait-associated SNPs, SNPs found on a common genotyping array, or randomly permuted SNPs. 13.5% of the erythroid trait-associated SNPs fell directly into erythroid enhancers, an 11.4-fold enrichment over random permuted enhancers ($P<1\times10^{-4}$), as compared to 1.4% of non-erythroid trait-associated SNPs, representing a 1.4-fold enrichment ($P=0.0013$). Many of the erythroid trait-associated SNPs were found in close proximity to erythroid enhancers (FIG. 1B). The median distance to erythroid enhancer was 16.0 kilobases (kb) for erythroid trait-associated SNPs, as compared to 238.0, 392.6, and 482.4 kb respectively for non-erythroid trait-associated, genotyping array, and randomly permuted SNPs. These results indicate that a substantial fraction of common variants associated with erythroid traits reside at or near erythroid enhancers, and are consistent with the hypothesis that causal variants often influence context-dependent gene regulation.

HbF GWAS Mark an Erythroid Enhancer Signature

Six GWAS have been conducted of HbF level (or the highly correlated trait F-cell number), including populations of European, African, and Asian descent. Each has identified trait-associated variants within BCL11A. Variation at BCL11A is estimated to explain ~15% of the trait variance. Four different SNPs have been identified as most highly associated with the trait (rs1427407, rs11886868, rs4671393, and rs766432; these so-called "sentinel" SNPs cluster within 3 kb of each other in BCL11A intron-2 (FIG. 2A). Haplotypes including the sentinel SNPs appear to better explain the HbF association than any individual SNP. Fifty SNPs at the BCL11A locus and twenty-seven SNPs within intron-2 have been associated with HbF level with at least genome-wide significance ($P<5\times10^{-8}$).

The distribution of the HbF-associated SNPs at BCL11A were compared with DNase I sensitivity, an indicator of chromatin state suggestive of regulatory potential. In human erythroid precursors, three peaks of DNase I hypersensitivity were observed in intron-2, adjacent to and overlying the HbF-associated variants (FIG. 2A), termed DNase I hypersensitive sites (DHSs) +62, +58, and +55 based on distance in kb from the TSS of BCL11A. Brain and B-lymphocytes, two tissues that express high levels of BCL11A, and T-lymphocytes, which do not express appreciable BCL11A, show unique patterns of DNase I sensitivity at the BCL11A locus, with a paucity of DNase I hypersensitivity overlying the trait-associated SNPs (FIG. 2A).

The chromatin signature around the BCL11A locus was further analyzed by chromatin immunoprecipitation with massively parallel sequencing (ChIP-seq). ChIP-seq from primary human erythroid precursors revealed histone modifications with an enhancer signature overlying the trait-associated SNPs at BCL11A intron-2, including the presence of H3K4me1 and H3K27ac and absence of H3K4me3 and H3K27me3 marks (FIG. 2A). The master erythroid transcription factors GATA1 and TAL1 occupy this enhancer region (FIG. 2A). ChIP-qPCR experiments demonstrated three discrete peaks of GATA1 and TAL1 binding within BCL11A intron-2, each falling within an erythroid DHS (FIG. 2B).

Figure 2C:
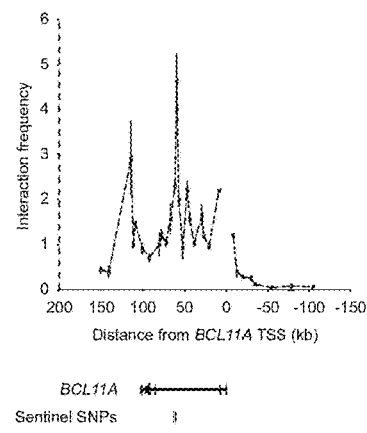
FIG. 2C shows chromosome conformation capture performed in primary human erythroid precursors across BCL11A locus using BCL11A promoter as anchor. Interaction frequency is normalized to LCR-HBB interaction.

One common feature of distal regulatory elements is long-range interaction with the promoters whose expression they regulate. The interactions between the BCL11A promoter and fragments across 250 kb of the BCL11A locus were evaluated, including sequences upstream, downstream, and intragenic. The greatest promoter interaction was observed within the region of intron-2 containing the erythroid DHS and trait-associated SNPs (FIG. 2C). These results indicate that these sequences have regulatory potential.

Regulatory Variants

It was hypothesized that the causal trait-associated SNPs could function by modulating critical cis-regulatory elements. Therefore, extensive genotyping of SNPs was performed within the three erythroid DHSs +62, +58, and +55 in 1263 DNA samples from the Cooperative Study of Sickle Cell Disease (CSSCD), an African-American sickle cell disease cohort for which genomic DNA is available and HbF levels are known. 66 DNA sequence variants located in the three DHSs from dbSNP were identified from reference populations CEU, YRI, and ASW within the 1000 Genomes Project, and by Sanger sequencing 88 individuals from the CSSCD with extreme HbF phenotype. 26 markers failed genotyping assay design and 18 were monomorphic (Tables 1 and 2). After quality control, 1178 individuals and 20 polymorphic SNPs remained for association testing. Analysis of common variants (minor allele frequency (MAF)>1%) revealed that rs1427407 in DHS +62 had the strongest association to HbF level ($P=7.23\times10^{-50}$, Table 1).

Previously, the inventors had used the CSSCD to fine-map the association signal with HbF at the BCL11A locus and reported a strong association with rs4671393; in that study, rs1427407 was imputed. Two additional SNPs, rs766432 and rs11886868 have also been identified in prior studies as sentinel SNPs most highly associated with HbF level (or F-cell number). In a subset of individuals (N=728) for which genotypes at all four sentinel SNPs were known, when conditioned on genotypes at rs1427407, the association result was not significant at rs4671393, rs766432, or rs11886868; conversely, the association remained highly significant for rs1427407 when conditioning on rs4671393, rs766432, or rs11886868 (Table 3). Therefore, rs1427407 is the SNP most associated with HbF within the erythroid DHS and better accounts for the trait association than other previously described sentinel SNPs.

When conditioned on rs1427407, other associations to HbF level were found within the three DHSs that were not completely lost (Table 1). The most significant association remaining was for rs7606173 in DHS +55 ($P=5.11\times10^{-10}$); rs7599488 in DHS +58, which were previously reported, was only slightly less significant ($P=1.71\times10^{-9}$) in this conditional analysis. After conditioning on rs1427407 and rs7606173, no more SNPs were significant (Table 1). Adjusting for principal components (PCs) on 855 individuals for whom genome-wide genotyping data was available to account for admixture and other confounders yielded similar results (data not shown). The rs1427407-rs7606173 T-G haplotype was defined as that most highly associated with HbF level.

Rare and low-frequency variants (MAF<5%) were also analyzed for their association with HbF levels using each of the three DHSs +62, +58, and +55 as a testing set. Two sets were found to be significant, namely DHS +62 and DHS +55, but after conditioning on rs1427407 and rs7606173, results were no longer significant, indicating weak LD between the rare/low-frequency variants and the common SNPs (Table 4). Therefore, no evidence that rare and low-frequency sequence variants within the BCL11A DHSs influence HbF levels in SCD patients was found, despite Sanger resequencing 88 individuals from CSSCD with extreme HbF phenotype.

The SNP rs1427407 falls within a peak of GATA1 and TAL1 binding as determined by ChIP-seq and ChIP-qPCR (FIGS. 2A and 2B). The minor T-allele disrupts the G-nucleotide of a sequence element highly resembling a half-E-box/GATA composite motif [CTG($n_9$)GATA (SEQ ID NO: 6)]. This motif has been found to be highly enriched by GATA1 and TAL1 complexes in erythroid cells by ChIP-seq experiments. Primary erythroid samples were identified from individuals heterozygous for the major G-allele and minor T-allele at rs1427407 and subjected these samples to ChIP followed by pyrosequencing. The inventors identified an even balance of alleles in the input DNA. However more frequent binding to the G-allele was observed compared to the T-allele of approximately 60:40 in both the GATA1 and TAL1 immunoprecipitated chromatin samples (FIG. 3A).

It was previously reported that the high-HbF associated A-allele of rs4671393 was associated with BCL11A expression in human lymphoblastoid cell lines. The inventors were unable to reproduce a significant association between BCL11A genotype and expression level analyzing a larger set of lymphoblastoid cell lines (data not shown). It was speculated that the high-HbF-associated rs1427407-rs7606173 haplotype influences BCL11A expression in an erythroid-specific context. The common synonymous SNP rs7569946 lies within exon-4 of BCL11A and may serve as a marker of allelic expression. Three primary human erythroid samples were identified that were doubly heterozygous for the rs1427407-rs7606173 haplotype and rs7569946. The samples were subjected to molecular haplotyping by emulsion fusion PCR. The haplotyping demonstrated that for each sample the major rs7569946 G-allele was in phase with the low-HbF-associated rs1427407-rs7606173 G-C haplotype. Genomic DNA and cDNA were assayed by pyrosequencing of rs7569946 to determine allelic balance. Whereas the alleles were balanced in the genomic DNA, significant imbalance in the cDNA favoring increased expression of the low-HbF linked G-allele of rs7569946 was observed (FIG. 3B). These results indicate that the high-HbF rs1427407 T-allele, which disrupts the half-E-box/GATA motif, is associated with reduced binding of GATA1 and TAL1 and reduced expression of BCL11A in erythroid precursors. The mean HbF level in 60 high-HbF rs1427407-rs7606173 T-G haplotype homozygous individuals was 11.21% as compared to 4.05% in 213 low-HbF rs1427407-rs7606173 G-C haplotype homozygous individuals ($P=2.5\times10^{-19}$) (FIG. 3C). In sum, the following evidence indicates that rs1427407 is a causal SNP for HbF level: it has the highest association to the phenotype of any known variant, it accounts for the associations observed with previously described sentinel SNPs, it impacts a motif required for GATA1 and TAL1 binding, and it is associated with GATA1 and TAL1 binding as well as with BCL11A expression. However, variation at this position in the setting of common haplotypes is associated with only modest perturbation of BCL11A expression.

Enhancer Sufficiency for Erythroid Expression

To understand the context within which these apparent regulatory trait-associated SNPs play their role, the function of the harboring cis-regulatory elements was explored. The inventors cloned ~12-kb (+52.0-64.4 kb from TSS) which contained the three erythroid DHSs, and assayed enhancer potential in a transgenic reporter assay. In this assay putative enhancer sequences are positioned upstream of a minimal promoter (Hsp68) and reporter gene (lacZ) bounded by insulator sequences. Constructs were introduced to murine zygotes with reporter gene expression monitored throughout development. Endogenous mouse BCL11A showed abundant expression throughout the developing central nervous system with much lower expression observed in the fetal liver. In contrast, reporter gene expression in the transgenic embryos was observed to be largely confined to the fetal liver, the site of definitive erythropoiesis, with lesser expression noted in the central nervous system (FIG. 4A).

A characteristic feature of globin genes is their developmental regulation. During human development, yolk sac-derived ε-globin is superseded in the first trimester by fetal liver-derived γ-globin. Around birth, γ-globin is gradually silenced and β-globin becomes activated. There is only a single switch in gene expression during mouse ontogeny. During this transition, which occurs at mid-gestation, the circulating yolk sac-derived primitive erythrocytes express embryonic-stage globins εy and βH1 whereas the fetal liver definitive erythroblasts express adult-stage globins β1 and β2. Concordant with this developmental switch, BCL11A expression is expressed in the definitive but not primitive stage erythroid lineage. Stable transgenic lines were derived from the BCL11A +52.0-64.4 reporter mice. In these mice at E12.5 circulating erythrocytes do not stain for X-gal whereas liver erythroblasts robustly stain positive (FIG. 4B). At E10.5 lacZ expression is only observed in the fetal liver primordium and not in the circulating blood within the embryo, placenta, or yolk sac (FIG. 6A). These results indicate that the GWAS-marked BCL11A intron-2 regulatory sequences are sufficient to specify developmentally appropriate gene expression.

Within the hematopoietic compartment, BCL11A expression is found in erythroid precursors and B-lymphocytes. Erythroid precursors and B-lymphocytes were isolated from transgenic young adult animals and expression of the lacZ reporter gene was evaluated. Endogenous BCL11A was expressed at 10.4-fold higher levels in splenic B-lymphocytes as compared to bone marrow erythroid precursors. However, lacZ expression was restricted to erythroid precursors and was not observed in B-lymphocytes (FIG. 4C). These results indicate erythroid-specificity of these regulatory sequences.

A series of deletion mutants was generated to refine the minimal elements required for erythroid enhancer activity. Sequences containing the central +58 DHS were sufficient for erythroid enhancer activity. Those sequences containing only the flanking +62 or +55 elements were not able to direct erythroid gene expression (FIG. 6B). These DHSs were also tested for their ability to enhance gene expression in primary human erythroid precursors. The inventors used lentiviral delivery of a GFP reporter system with a minimal TK promoter as previously described. Similarly, only the +58 but not the +55 or +62 DHSs were able to enhance gene expression in this reporter assay (FIG. 7).

Enhancer Requirement for Erythroid Expression

Next the inventors chose to determine the requirement of these regulatory sequences for appropriate expression of BCL11A and globin genes. Inspection of the Bcl11a locus in previously published global chromatin profiling of mouse erythroid cells revealed that this region of intron-2 possesses an orthologous enhancer signature with presence of H3K4me1 and H3K27ac, absence of H3K4me3 and H3K27me3, and occupancy by GATA1 and TAL1 (FIG. 8). Moreover, erythroid-specific DNase I hypersensitivity was observed at these sequences. At each of the human erythroid DHSs +62, +58, and +55, evidence of evolutionary sequence conservation was observed, particularly within +62 and +55. To determine the requirement of these orthologous regulatory sequences for BCL11A expression, the mouse erythroleukemia cell line (MEL) was used. These cells depend on BCL11A expression for appropriate adult-stage pattern globin gene expression. Sequence-specific nucleases can result in the production of small chromosomal deletions. TALENs were engineered to introduce double-strand breaks to flank the orthologous 10-kb Bcl11a intron-2 sequences carrying the erythroid enhancer chromatin signature. Clones were screened for NHEJ-mediated repair and three unique clones were isolated that had undergone biallelic excision. PCR and Southern blotting verified excision of the intronic segment within clones (FIG. 9). Sanger-sequenced breakpoints were characteristic of TALEN-mediated cleavage with subsequent NHEJ repair (FIG. 10).

Figure 5B:
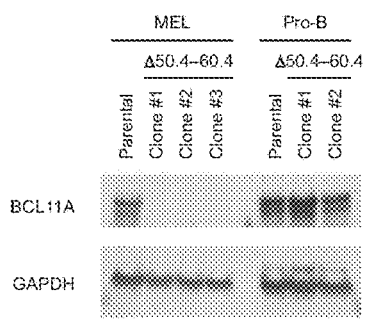
Figure 5C:
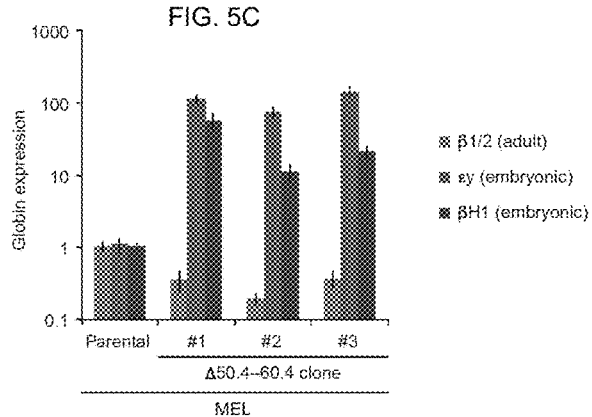

Expression of BCL11A was analyzed in the MEL cells with biallelic 10-kb intronic deletion. A dramatic reduction of BCL11A expression to ~3% of baseline levels was observed (FIG. 5A). Similar reductions were noted with primer pairs detecting exon junctions upstream, spanning, or downstream of the deletion. By Western blotting, BCL11A expression was not detectable in the 10-kb enhancer deleted clones (FIG. 5B). MEL cells typically express high levels of the adult globin genes β1 and β2 and low levels of the embryonic globin genes εy and βH1. In the absence of the 10-kb enhancer for BCL11A, expression of adult globin genes was decreased by ~2-5-fold, whereas embryonic globin genes were considerably derepressed. The ratio of embryonic εy to adult β1/2 was increased by a mean of 364-fold in three clones lacking the orthologous BCL11A erythroid enhancer (FIG. 5C).

To determine if the +50.4-60.4 kb intronic sequences were universally required for BCL11A expression, their loss was evalutated in a non-erythroid context. The same strategy of introduction of two pairs of TALENs to obtain clones with the NHEJ-mediated Δ50.4-60.4 deletion was employed in a pro-B lymphocyte cell line. Two unique Δ50.4-60.4 clones were isolated, and verified by PCR, Southern blotting, and Sanger sequencing (FIGS. 9 and 10). In contrast to the erythroid cells, BCL11A expression was retained in the Δ50.4-60.4kb enhancer deleted pro-B cell clones at both the RNA and protein levels (FIGS. 5A and 5B). These results indicate the orthologous erythroid enhancer sequences are not required for integrity of transcription from the Bcl11a locus but only essential for erythroid gene expression.

An enhancer chromatin signature was found at intron-2 of BCL11A, directly overlying the HbF-associated SNPs. This region had numerous biochemical features of an enhancer, including occupancy by the histone marks H3K4me1 and H3K27ac in the absence of H3K4me3 and H3K27me3, binding of the erythroid TFs GATA1 and TAL1, erythroid-specific DNase-I hypersensitive sites, and long-range promoter interaction by 3C. Moreover, the inventors were able to fine-map this locus, using the DHSs as a guide, to identify the SNP rs1424707 as being most highly associated with the trait, and entirely accounting for the trait association of the previously described and highly linked sentinel SNPs. In addition, it is shown herein that rs1427407 disrupts a half-E-box/GATA motif occupied by the transcription factors GATA1 and TAL1 in erythroid precursors. However, even after conditioning on rs1427407 an association remains with several other SNPs in adjacent DHSs indicating a haplotype effect. It was found that haplotypes which possess a combination of SNP genotypes in adjacent elements that each modulate regulatory function cooperate to give the ultimate phenotype of BCL11A expression. Using heterozygous donors, a modest impact of the high-HbF associated haplotype was demonstrated on both TF binding and BCL11A expression.

These studies help to estimate the change in BCL11A expression required to result in a clinically meaningful increase in HbF level in patients with β-globin disorders. The difference in BCL11A expression between the high-HbF rs1427407-rs7606173 T-G and low-HbF G-C haplotypes was 1.7-fold and the HbF levels of T-G and G-C homozygotes were 11.2% and 4.1% (FIGS. 3B and 3C). HbF levels of >20% have been predicted to prevent the adverse consequences of SCD. A reduction in BCL11A expression of several-fold would likely approach this HbF goal.

This study identifies regulatory variation at BCL11A that impacts an erythroid enhancer. Many trait-associated SNPs are noncoding and have relatively small effect size. Due to these features, these SNPs are sometimes considered to be of negligible clinical importance. This study illustrates that a small effect size engendered by an individual noncoding variant does not preclude a large effect size of the underlying regulatory element. For example, despite a relatively modest impact of functional SNPs on expression of the underlying gene target BCL11A, the causal regulatory elements are essential for expression of BCL11A and globin genes in adult-stage erythroid precursors. The same regulatory element is dispensable for BCL11A expression in a non-erythroid lineage. A goal of studying protective alleles is to understand their underlying molecular mechanisms in an effort to reproduce this biological effect in at-risk individuals. Thus, many trait-associated polymorphisms will reside context-specific critical regulatory elements whose function may further illuminate the underlying biology of the trait beyond merely identifying the regulated gene. For example loss of BCL11A while resulting in impaired hemoglobin switching also results in impaired neurogenesis and lymphopoeisis and results in embryonic lethality. Ultimately a better understanding of the causal regulatory elements and associated regulatory networks underlying traits could identify novel therapeutic targets. The erythroid enhancer of BCL11A could itself constitute a favorable target for therapeutic genome editing in that ablation could impede BCL11A expression in erythroid precursors with resultant HbF derepression while preserving BCL11A expression in non-erythroid lineages.

REFERENCES

1. L. Fugger, G. McVean, J. I. Bell, N. Engl. J. Med. 367, 2370-2371 (2012).
2. J. Ernst et al., Nature. 473, 43-49 (2011).
3. D. S. Paul et al., PLoS Genet. 7, e1002139 (2011).
4. M. T. Maurano et al., Science. 337, 1190-1195 (2012).
5. P. van der Harst et al., Nature. 492, 369-375 (2012).
6. ENCODE Project Consortium et al., Nature. 489, 57-74 (2012).
7. S. Menzel et al., Nat. Genet. 39, 1197-1199 (2007).
8. M. Uda et al., Proc. Natl. Acad. Sci. U.S.A. 105, 1620-1625 (2008).
9. G. Lettre et al., Proc. Natl. Acad. Sci. U.S.A. 105, 11869-11874 (2008).
10. M. Nuinoon et al., Hum. Genet. 127, 303-314 (2010).
11. N. Solovieff et al., Blood. 115, 1815-1822 (2010).
12. P. Bhatnagar et al., J. Hum. Genet. 56, 316-323 (2011).
13. V. G. Sankaran et al., Science. 322, 1839-1842 (2008).
14. J. Xu et al., Genes Dev. 24, 783-798 (2010).
15. J. Xu et al., Proc. Natl. Acad. Sci. U. S. A. 110, 6518-6523 (2013).
16. V. G. Sankaran et al., Nature. 460, 1093-1097 (2009).
17. J. Xu et al., Science. 334, 993-996 (2011).
18. F. Esteghamat et al., Blood. 121, 2553-2562 (2013).
19. P. Liu et al., Nat. Immunol. 4, 525-532 (2003).
20. Y. Yu et al., J. Exp. Med. 209, 2467-2483 (2012).
21. M. D. Farber, M. Koshy, T. R. Kinney, J. Chronic Dis. 38, 495-505 (1985).
22. E. Soler et al., Genes Dev. 24, 277-289 (2010).
23. M. T. Kassouf et al., Genome Res. 20, 1064-1083 (2010).
24. D. J. Turner, M. E. Hurles, Nat. Protoc. 4, 1771-1783 (2009).
25. J. Tyson, J. A. Armour, BMC Genomics. 13, 693-2164-13-693 (2012).
26. M. Leid et al., Gene Expr. Patterns. 4, 733-739 (2004).
27. M. S. Kowalczyk et al., Mol. Cell. 45, 447-458 (2012).
28. H. J. Lee, E. Kim, J. S. Kim, Genome Res. 20, 81-89 (2010).
29. D. E. Bauer, S. C. Kamran, S. H. Orkin, Blood. 120, 2945-2953 (2012).
30. A. John et al., Development. 139, 1831-1841 (2012).
31. R. P. Patwardhan et al., Nat. Biotechnol. 30, 265-270 (2012).
32. A. Melnikov et al., Nat. Biotechnol. 30, 271-277 (2012).
33. K. A. Frazer, S. S. Murray, N. J. Schork, E. J. Topol, Nat. Rev. Genet. 10, 241-251 (2009).
34. A. N. Koehler, Curr. Opin. Chem. Biol. 14, 331-340 (2010).
35. F. D. Urnov, E. J. Rebar, M. C. Holmes, H. S. Zhang, P. D. Gregory, Nat. Rev. Genet. 11, 636-646 (2010).
36. J. K. Joung, J. D. Sander, Nat. Rev. Mol. Cell Biol. 14, 49-55 (2013).
37. J. van der Oost, Science. 339, 768-770 (2013).
38. Thanks to A. Woo, A. Cantor, M. Kowalczyk, S. Burns, J. Wright, J. Snow, J. Trowbridge and members of the Orkin laboratory, particularly C. Peng, P. Das, G. Guo, M. Kerenyi, and E. Baena, for discussions. C. Guo and F. Alt provided the pre-B cell line, A. He and W. Pu the pWHERE lacZ reporter construct, C. Currie and M. Nguyen technical assistance, D. Bates and T. Kutyavin expertise with sequence analysis, R.
39. J. Xu et al., Dev. Cell. 23, 796-811 (2012).
40. E. van den Akker, T. J. Satchwell, S. Pellegrin, G. Daniels, A. M. Toye, Haematologica. 95, 1594-1598 (2010).
41. A. L. Bredemeyer et al., Nature. 442, 466-470 (2006).
42. R. E. Thurman et al., Nature. 489, 75-82 (2012).
43. G. Galarneau et al., Nat. Genet. 42, 1049-1051 (2010).
44. S. Purcell et al., Am. J. Hum. Genet. 81, 559-575 (2007).
45. M. C. Wu et al., Am. J. Hum. Genet. 89, 82-93 (2011).
46. A. He, S. W. Kong, Q. Ma, W. T. Pu, Proc. Natl. Acad. Sci. U.S.A. 108, 5632-5637 (2011).
47. M. A. McDevitt, Y. Fujiwara, R. A. Shivdasani, S. H. Orkin, Proc. Natl. Acad. Sci. U.S.A. 94, 7976-7981 (1997).
48. T. Cermak et al., Nucleic Acids Res. 39, e82 (2011).
49. J. C. Miller et al., Nat. Biotechnol. 29, 143-148 (2011).
50. R. Galanello et al., Blood. 114, 3935-3937 (2009).
51. H. T. Bae et al., Blood. 120, 1961-1962 (2012).
52. K. E. McGrath et al., Blood. 117, 4600-4608 (2011).
53. D. Noordermeer, W. de Laat, IUBMB Life. 60, 824-833 (2008).
54. D. R. Higgs, D. Vernimmen, B. Wood, Adv. Genet. 61, 143-173 (2008).
55. E. Pinaud et al., Adv. Immunol. 110, 27-70 (2011).

TABLE 1

Association analysis of common SNPs in BCL11A DHSs +62, +58, or +55

| DHS | Marker | MAF | β | P | Conditional on rs1427407 β | Conditional on rs1427407 P | Conditional on rs1427407 and rs7606173 β | Conditional on rs1427407 and rs7606173 P |
|---|---|---|---|---|---|---|---|---|
| +62 | rs111575474 | 0.0153 | −0.2624 | 0.09762 | −0.0851 | 0.5584 | 0.0486 | 0.7368 |
| +62 | rs112105713 | 0.0115 | −0.3285 | 0.07755 | −0.2137 | 0.2097 | −0.0859 | 0.6107 |
| +62 | rs74958177 | 0.0646 | −0.3614 | $2.79 \times 10^{-6}$ | −0.1838 | 0.01041 | −0.0832 | 0.2518 |
| +62 | rs1427407 | 0.2460 | 0.6634 | $7.23 \times 10^{-50}$ | — | — | — | — |
| +62 | rs7599488 | 0.3148 | −0.0047 | 0.9116 | 0.2622 | $2.43 \times 10^{-10}$ | 0.0915 | 0.3547 |
| +62 | rs1896293 | 0.1089 | −0.2623 | $2.52 \times 10^{-5}$ | −0.1248 | 0.03098 | 0.0241 | 0.6952 |
| +58 | rs6738440 | 0.2734 | −0.3820 | $1.25 \times 10^{-18}$ | −0.1935 | $5.64 \times 10^{-6}$ | −0.0223 | 0.6887 |
| +55 | rs147910897 | 0.0132 | −0.3656 | 0.03294 | −0.2586 | 0.09945 | −0.1575 | 0.3101 |
| +55 | rs148529953 | 0.0140 | −0.3521 | 0.04034 | −0.1423 | 0.3668 | −0.0098 | 0.9501 |
| +55 | rs7606173 | 0.4238 | −0.4691 | $2.86 \times 10^{-34}$ | −0.2632 | $9.66 \times 10^{-11}$ | — | — |

Association analysis of common (MAF >1%) SNPs in BCL11A DHSs +62, +58, or +55 from 1178 individuals from CSSCD available for analysis. DHS, DNase I hypersensitive site. MAF, minor allele frequency.

TABLE 2

SNPs within BCL11A DHSs +62, +58, or +55

| Marker | CHR | POS | Major Allele | Minor Allele | DHS | Genotyped | MAF |
|---|---|---|---|---|---|---|---|
| rs149113684 | 2 | 60,717,544 | C | A | +62 | Monomorphic | 0.0000 |
| rs111575474 | 2 | 60,717,559 | C | T | +62 | YES | 0.0157 |
| rs148272134 | 2 | 60,717,643 | C | A | +62 | Failed Assay Design | — |
| rs182773253 | 2 | 60,717,676 | A | G | +62 | Monomorphic | 0.0000 |
| rs188706265 | 2 | 60,717,769 | C | T | +62 | Monomorphic | 0.0000 |
| rs74958177 | 2 | 60,717,776 | A | G | +62 | YES | 0.0645 |
| rs1427407 | 2 | 60,718,043 | G | T | +62 | YES | 0.2460 |
| rs35262352 | 2 | 60,718,076 | A | — | +62 | Failed Assay Design | — |
| rs79781583 | 2 | 60,718,077 | A | T | +62 | Failed Assay Design | — |
| rs201428515 | 2 | 60,718,088 | G | A | +62 | Monomorphic | 0.0000 |
| rs112105713 | 2 | 60,718,278 | G | A | +62 | YES | 0.1145 |
| rs7599488 | 2 | 60,718,347 | C | T | +62 | YES | 0.3149 |
| rs113636744 | 2 | 60,718,540 | C | T | +62 | YES | 0.0042 |
| rs35259900 | 2 | 60,718,555 | C | T | +62 | Failed Assay Design | — |
| rs111911554 | 2 | 60,718,569 | A | G | +62 | Failed Assay Design | — |
| rs137943695 | 2 | 60,718,574 | G | A | +62 | Monomorphic | 0.0000 |
| rs45579333 | 2 | 60,718,599 | G | A | +62 | Monomorphic | 0.0000 |
| rs77876582 | 2 | 60,718,639 | C | T | +62 | Failed Assay Design | — |
| rs112634025 | 2 | 60,718,708 | G | A | +62 | Failed Assay Design | — |
| rs45439602 | 2 | 60,718,721 | G | A | +62 | Failed Assay Design | — |
| rs112387548 | 2 | 60,718,762 | C | T | +62 | Failed Assay Design | — |
| rs191369155 | 2 | 60,718,781 | G | A | +62 | Failed Assay Design | — |
| rs6723022 | 2 | 60,718,807 | A | C | +62 | Monomorphic | 0.0000 |
| rs11422901 | 2 | 60,718,819 | G | A | +62 | Failed Assay Design | — |
| rs200632291 | 2 | 60,718,824 | A | G | +62 | Failed Assay Design | — |
| rs11387709 | 2 | 60,718,826 | A | — | +62 | Failed Assay Design | — |
| rs1896293 | 2 | 60,718,848 | G | T | +62 | YES | 0.1088 |
| rs71526487 | 2 | 60,721,587 | T | C | +58 | Failed Assay Design | — |
| rs185151573 | 2 | 60,721,639 | G | C | +58 | Monomorphic | 0.0000 |
| rs6721788 | 2 | 60,721,846 | T | C | +58 | YES | 0.0025 |
| rs76033449 | 2 | 60,721,900 | G | A | +58 | YES | 0.0004 |
| rs6706648 | 2 | 60,722,040 | T | C | +58 | Failed Genotyping | — |
| rs62142615 | 2 | 60,722,120 | T | C | +58 | YES | 0.0081 |
| rs35923541 | 2 | 60,722,197 | T | — | +58 | Monomorphic | 0.0000 |
| rs35815093 | 2 | 60,722,208 | G | — | +58 | Failed Assay Design | — |
| rs147659683 | 2 | 60,722,219 | G | A | +58 | Failed Assay Design | — |
| rs6738440 | 2 | 60,722,241 | A | G | +58 | YES | 0.2732 |
| rs189178945 | 2 | 60,722,449 | G | A | +58 | Monomorphic | 0.0000 |
| rs140819321 | 2 | 60,722,465 | G | A | +58 | YES | 0.0064 |
| rs181895125 | 2 | 60,722,609 | A | G | +58 | Monomorphic | 0.0000 |
| rs144676401 | 2 | 60,722,634 | C | T | +58 | Monomorphic | 0.0000 |
| rs147910897 | 2 | 60,724,818 | T | C | +55 | YES | 0.0132 |
| rs34322220 | 2 | 60,724,831 | T | — | +55 | Monomorphic | 0.0000 |
| rs148529953 | 2 | 60,724,967 | A | G | +55 | YES | 0.0140 |
| rs188426060 | 2 | 60,724,989 | T | G | +55 | Failed Assay Design | — |
| rs191734859 | 2 | 60,724,994 | A | G | +55 | Failed Assay Design | — |
| rs45442493 | 2 | 60,725,043 | G | C | +55 | Monomorphic | 0.0000 |
| rs59444712 | 2 | 60,725,047 | T | C | +55 | Failed Assay Design | — |
| rs35173197 | 2 | 60,725,052 | G | — | +55 | Failed Assay Design | — |
| rs188151753 | 2 | 60,725,071 | G | A | +55 | Failed Assay Design | — |

TABLE 2-continued

SNPs within BCL11A DHSs +62, +58, or +55

| Marker | CHR | POS | Major Allele | Minor Allele | DHS | Genotyped | MAF |
|---|---|---|---|---|---|---|---|
| rs181041409 | 2 | 60,725,143 | C | A | +55 | Failed Assay Design | — |
| rs142174420 | 2 | 60,725,169 | C | A | +55 | Monomorphic | 0.0000 |
| rs187333125 | 2 | 60,725,342 | C | G | +55 | Monomorphic | 0.0000 |
| rs45566439 | 2 | 60,725,384 | C | T | +55 | Failed Assay Design | — |
| rs7606173 | 2 | 60,725,451 | G | C | +55 | YES | 0.4235 |
| rs190502487 | 2 | 60,725,499 | C | T | +55 | Failed Assay Design | — |
| rs151187913 | 2 | 60,725,714 | G | T | +55 | Monomorphic | 0.0000 |
| rs113798461 | 2 | 60,725,727 | T | C | +55 | Monomorphic | 0.0000 |
| rs181699714 | 2 | 60,726,054 | G | A | +55 | Failed Genotyping | — |

SNPs falling within BCL11A DHSs +62, +58, or +55 and present in either dbSNP or the 1000 Genomes data for YRI, CEU and ASW reference populations. Genotyped SNPs are identified and MAF within the CSSCD listed. Genomic coordinates hg19.

TABLE 3

Additional markers found by Sanger re-sequencing

| Marker | CHR | POS | Major Allele | Minor Allele | DHS | Genotyped | MAF |
|---|---|---|---|---|---|---|---|
| ss711589103 | 2 | 60,717,561 | T | A | +62 | YES | 0.00085 |
| ss711589106 | 2 | 60,718,048 | C | G | +62 | Failed Assay Design | — |
| ss711589108 | 2 | 60,722,056 | G | A | +58 | YES | 0.00424 |
| ss711589109 | 2 | 60,722,355 | C | T | +58 | YES | 0.00085 |
| ss711589110 | 2 | 60,722,358 | C | T | +58 | Failed Assay Design | — |
| ss711589111 | 2 | 60,725,211 | G | T | +55 | YES | 0.00509 |
| ss711589113 | 2 | 60,725,564 | C | A | +55 | YES | 0.00127 |

88 individuals from CSSCD with extreme HbF phenotype underwent Sanger re-sequencing of the three DHSs within BCL11A. Identified novel markers listed. Genotyped SNPs are identified and MAF within the CSSCD listed. Genomic coordinates hg19.

TABLE 4

Conditional analyses of four sentinel SNPs

| Marker | MAF | β | P | Conditional on rs1427407 β | P | Conditional on rs766432 β | P | Conditional on rs11886868 β | P | Conditional on rs4671393 β | P |
|---|---|---|---|---|---|---|---|---|---|---|---|
| rs1427407 | 0.245 | 0.659 | $4.56 \times 10^{-29}$ | — | — | 0.656 | $3.38 \times 10^{-6}$ | 0.651 | $2.77 \times 10^{-10}$ | 0.666 | $1.86 \times 10^{-6}$ |
| rs766432 | 0.275 | 0.579 | $2.48 \times 10^{-24}$ | 0.0036 | 0.979 | — | — | 0.479 | $1.07 \times 10^{-5}$ | NA | NA |
| rs11886868 | 0.302 | 0.509 | $2.51 \times 10^{-21}$ | 0.0097 | 0.918 | 0.112 | 0.284 | — | — | 0.123 | 0.234 |
| rs4671393 | 0.274 | 0.576 | $4.41 \times 10^{-24}$ | −0.0065 | 0.961 | NA | NA | 0.466 | $1.7 \times 10^{-5}$ | — | — |

Conditional analyses of four common sentinel SNPs previously associated with HbF levels{{44;20;19;36;37;515}}. All four were genotyped in 728 individuals from the CSSCD. It was not possible to calculate P for rs766432 when conditioning on rs4671393 (and vice versa) because these two markers are so strongly correlated ($r^2 = 0.997$).

$r^2 = 0.848$ between rs1427407 and rs766432;

$r^2 = 0.709$ between rs1427407 and rs11886868;

$r^2 = 0.850$ between rs1427407 and rs4671393;

$r^2 = 0.761$ between rs766432 and rs11886868;

$r^2 = 0.758$ between rs11886868 and rs4671393.

TABLE 5

Rare and low-frequency variant analysis

| DHS | Markers (n) | P | Conditional on rs1427407 P | Conditional on rs1427407 and rs7606173 P |
|---|---|---|---|---|
| +62 | 4 | 0.001488515 | 0.06092413 | 0.59352715 |
| +58 | 6 | 0.065057555 | 0.03668287 | 0.07145516 |
| +55 | 4 | 0.006806853 | 0.35021761 | 0.75880018 |
| all | 14 | 0.000631176 | 0.1503518 | 0.6908852 |

Rare and low-frequency variant analysis results (MAF < 5%). The analysis was performed using the set-based SKAT-O algorithm using the individual DHSs +62, +58, and +55 as three different sets. The bottom row "all" shows the results of the tests when the three regions were collapsed together.

TABLE 6

Emulsion fusion haplotyping PCR sequencing

| Donor no. | G-G | A-T | G-T | A-G | Likelihood ratio G-G/A-T.uhase |
|---|---|---|---|---|---|
| 1 | 19 | 22 | 4 | 2 | $1.63 \times 10^{29}$ |
| 2 | 22 | 14 | 2 | 3 | $3.78 \times 10^{26}$ |
| 3 | 25 | 23 | 9 | 10 | $4.69 \times 10^{11}$ |

Emulsion fusion PCR analysis of rs7569946-rs1427407 haplotype. Fusion PCR conducted in emulsion from three individual donors doubly heterozygous for rs7569946 and rs1427407, generating a fusion amplicon encompassing both SNPs. The fusion amplicon was cloned, and individual clones were Sanger sequenced. The number of clones of each genotype is listed. The likelihood ratio for the G-G/A-T as compared to G-T/A-G phase was calculated.

TABLE 7

Coordinates of fragments for reporter assays

| Reporter | Name | hg19, chr2 Start | hg19, chr2 End | Distance from BCL11A TSS (kb) Start | Distance from BCL11A TSS (kb) End | Length (bp) |
|---|---|---|---|---|---|---|
| LacZ | 52.0-64.4 | 60,716,189 | 60,728,612 | 64,444 | 52,021 | 12,423 |
|  | 56.8-64.4 | 60,716,189 | 60,723,870 | 64,444 | 56,763 | 7,681 |
|  | 52.0-57.6 | 60,722,992 | 60,728,612 | 57,641 | 52,021 | 5,620 |
|  | +62 | 60,717,236 | 60,719,036 | 63,397 | 61,597 | 1,800 |
|  | +58 | 60,722,006 | 60,723,058 | 58,627 | 57,575 | 1,052 |
|  | +55 | 60,724,917 | 60,726,282 | 55,716 | 54,351 | 1,365 |
| GFP | +164 | 60,616,396 | 60,618,032 | 164,237 | 162,601 | 1,636 |
|  | +156 | 60,623,536 | 60,624,989 | 157,097 | 155,644 | 1,453 |
|  | +153 | 60,626,565 | 60,628,177 | 154,068 | 152,456 | 1,612 |
|  | +62 | 60,717,236 | 60,719,036 | 63,397 | 61,597 | 1,800 |
|  | +58 | 60,721,212 | 60,722,958 | 59,421 | 57,675 | 1,746 |
|  | +55 | 60,724,780 | 60,726,471 | 55,853 | 54,162 | 1,691 |
|  | +41 | 60,739,075 | 60,740,154 | 41,558 | 40,479 | 1,079 |
|  | +32 | 60,748,003 | 60,749,009 | 32,630 | 31,624 | 1,006 |
|  | −46 | 60,826,438 | 60,827,601 | −45,805 | −46,968 | 1,163 |
|  | −52 | 60,831,589 | 60,833,556 | −50,956 | −52,923 | 1,967 |

Coordinates of the putative enhancer fragments cloned in the enhancer reporter assays.
Chromosome 2 coordinates listed in hg19 as well as in reference to the BCL11A TSS.

TABLE 8

Oligonucleotide sequences.

| Name | Sequence | Assay | |
|---|---|---|---|
| mBcl11a-5'-F | AAAGAGCTGTCCGAAGTCCA | TALEN deletion PCR | (SEQ ID NO: 7) |
| mBcl11a-5'-R | GGGCACTTCCTAGTCCCTCT | TALEN deletion PCR | (SEQ ID NO: 8) |
| mBcl11a-del1-F | TTTGAGCAGGAGGGAATTTG | TALEN deletion PCR | (SEQ ID NO: 9) |
| mBcl11a-del1-R | ATGTTGTGGTCCCTGTGGTT | TALEN deletion PCR | (SEQ ID NO: 10) |
| mBcl11a-del2-F | GCAAGGCAGGTACCAAACAT | TALEN deletion PCR | (SEQ ID NO: 11) |
| mBcl11a-del2-R | TAGAGATTCCAGGCCCCTTT | TALEN deletion PCR | (SEQ ID NO: 12) |
| mBcl11a-3'-F | AGCAAGGAAAGGTGAAGCAG | TALEN deletion PCR | (SEQ ID NO: 13) |
| mBcl11a-3'-R | CCCAATGTCTTCCGAACTGT | TALEN deletion PCR | (SEQ ID NO: 14) |
| mBcl11a-upstreamTALEN-F | AGGCTGGTCTTGGGATTTTT | TALEN deletion PCR | (SEQ ID NO: 15) |
| mBcl11a-downstreamTALEN-R | GCCTTTAACAAGGGTGTCCA | TALEN deletion PCR | (SEQ ID NO: 16) |
| mBcl11a-5'probe-F | CATAGACCTGGGTCCTGGAA | 5'-probe for Southern blot | (SEQ ID NO: 17) |
| mBcl11a-5'probe-R | TTGCAGAGTGACTCCTGTGG | 5'-probe for Southern blot | (SEQ ID NO: 18) |

TABLE 8-continued

Oligonucleotide sequences.

| Name | Sequence | Assay | |
|---|---|---|---|
| hBCL11A-52.0-F | CCAGCCATACCCAAAACAAA | lacZ reporter cloning | (SEQ ID NO: 19) |
| hBCL11A-64.4-R | CTTTCCCTCTTGCCACTCAG | lacZ reporter cloning | (SEQ ID NO: 20) |
| hBCL11A-56.8-F | GGCAGAGAAGGCACAGTGA | lacZ reporter cloning | (SEQ ID NO: 21) |
| hBCL11A-57.6-R | GGCTGTCCTGGCATGTAAGT | lacZ reporter cloning | (SEQ ID NO: 22) |
| hBCL11A-63.4-F | AACAGACCCATGTGCTAGGC | lacZ/GFP reporter cloning | (SEQ ID NO: 23) |
| hBCL11A-61.6-R | TGTGTGGACTGCCTTTTCTG | lacZ/GFP reporter cloning | (SEQ ID NO: 24) |
| hBCL11A-58.6-F | GGGAAAAGGGAGAGGAAAAA | lacZ reporter cloning | (SEQ ID NO: 25) |
| hBCL11A-57.6-R | CTCAGAAAAATGACAGCACCA | lacZ reporter cloning | (SEQ ID NO: 26) |
| hBCL11A-55.7-F | GGACTCAGTGGCCTCTTTTG | lacZ reporter cloning | (SEQ ID NO: 27) |
| hBCL11A-54.4-R | GAAGATAATGGCAGCCCAGA | lacZ reporter cloning | (SEQ ID NO: 28) |
| hBCL11A-164.2-F | TGTGTGGCCAACCTGTAAAA | GFP reporter cloning | (SEQ ID NO: 29) |
| hBCL11A-162.6-R | CTCGCTCTGTTTCCCAGTTC | GFP reporter cloning | (SEQ ID NO: 30) |
| hBCL11A-157.1-F | CTCTCCGACGACCTCTTTTG | GFP reporter cloning | (SEQ ID NO: 31) |
| hBCL11A-155.6-R | GTAGGGAAGGGGCTACTTGG | GFP reporter cloning | (SEQ ID NO: 32) |
| hBCL11A-154.1-F | AGAGCCAAACTCCGTCTCAA | GFP reporter cloning | (SEQ ID NO: 33) |
| hBCL11A-152.5-R | AAATACCACAGCCCAACAGC | GFP reporter cloning | (SEQ ID NO: 34) |
| hBCL11A-59.4-F | GAACAGAGACCACTACTGGCAAT | GFP reporter cloning | (SEQ ID NO: 35) |
| hBCL11A-57.7-R | GGGGAAGGGGTATTGAATTG | GFP reporter cloning | (SEQ ID NO: 36) |
| hBCL11A-55.9-F | CTTCCACTGGATGGCACTTT | GFP reporter cloning | (SEQ ID NO: 37) |
| hBCL11A-54.2-R | ACTTCAGCCTCCAGCACTGT | GFP reporter cloning | (SEQ ID NO: 38) |
| hBCL11A-41.6-F | CCTCCCAGCAATGTAGGTGT | GFP reporter cloning | (SEQ ID NO: 39) |
| hBCL11A-40.5-R | TGGTGTGGTCCACTGTGACT | GFP reporter cloning | (SEQ ID NO: 40) |
| hBCL11A-32.6-F | GCAAGCTTAGCCCCTTCTTT | GFP reporter cloning | (SEQ ID NO: 41) |
| hBCL11A-31.6-R | TGAGGCAGAGTCAGATGTGG | GFP reporter cloning | (SEQ ID NO: 42) |
| hBCL11A-n45.8-F | CCCCGCTCAGAGTAAGTGAG | GFP reporter cloning | (SEQ ID NO: 43) |
| hBCL11A-n47.0-R | GGAAACTGCCTATCCCATGA | GFP reporter cloning | (SEQ ID NO: 44) |
| hBCL11A-n51.0-F | CAACACCCCGATTTCAGACT | GFP reporter cloning | (SEQ ID NO: 45) |
| hBCL11A-n52.9-R | GAATGGTCCCGATCTCTTGA | GFP reporter cloning | (SEQ ID NO: 46) |
| mGapdh-RT-F | TGGTGAAGGTCGGTGTGAAC | RT-qPCR (Gapdh) | (SEQ ID NO: 47) |
| mGapdh-RT-R | CCATGTAGTTGAGGTCAATGAAGG | RT-qPCR (Gapdh) | (SEQ ID NO: 48) |
| mBcl11a-RT-e1e2-F | AACCCCAGCACTTAAGCAAA | RT-qPCR (Bcl11a exon-1/2) | (SEQ ID NO: 49) |
| mBcl11a-RT-e1e2-R | ACAGGTGAGAAGGTCGTGGT | RT-qPCR (Bcl11a exon-1/2) | (SEQ ID NO: 50) |
| mBcl11a-RT-e2e3-F | GCCCCAAACAGGAACACATA | RT-qPCR (Bcl11a exon-2/3) | (SEQ ID NO: 51) |
| mBcl11a-RT-e2e3-R | GGGGCATATTCTGCACTCAT | RT-qPCR (Bcl11a exon-2/3) | (SEQ ID NO: 52) |
| mBcl11a-RT-e4e4-F | ATGCGAGCTGTGCAACTATG | RT-qPCR (Bcl11a exon-4/4, XLisoform) | (SEQ ID NO: 53) |
| mBcl11a-RT-e4e4-R | GTAAACGTCCTTCCCCACCT | RT-qPCR (Bcl11a exon-4/4, XLisoform) | (SEQ ID NO: 54) |

TABLE 8-continued

Oligonucleotide sequences.

| Name | Sequence | Assay | |
|---|---|---|---|
| mBcl11a-RT-e4e5-F | CAGCTCAAAAGAGGGCAGAC | RT-qPCR (Bcl11a exon-4/5, L isoform) | (SEQ ID NO: 55) |
| mBcl11a-RT-e4e5-R | GAGCTTCCATCCGAAAACTG | RT-qPCR (Bcl11a exon-4/5, L isoform) | (SEQ ID NO: 56) |
| mHbby-RT-F | TGGCCTGTGGAGTAAGGTCAA | RT-qPCR (eY) | (SEQ ID NO: 57) |
| mHbby-RT-R | GAAGCAGAGGACAAGTTCCCA | RT-qPCR (eY) | (SEQ ID NO: 58) |
| mHbb-bh1-RT-F | TGGACAACCTCAAGGAGACC | RT-qPCR (bH1) | (SEQ ID NO: 59) |
| mHbb-bh1-RT-R | ACCTCTGGGGTGAATTCCTT | RT-qPCR (bH1) | (SEQ ID NO: 60) |
| mHbb-b1-RT-F | TTTAACGATGGCCTGAATCACTT | RT-qPCR (b1/b2) | (SEQ ID NO: 61) |
| mHbb-b1-RT-R | CAGCACAATCACGATCATATTGC | RT-qPCR (b1/b2) | (SEQ ID NO: 62) |
| lacZ-RT-F | GCCAACATTGAGACACATGG | RT-qPCR (lacZ) | (SEQ ID NO: 63) |
| lacZ-RT-R | TGTCTCTCTGCACCATCCTG | RT-qPCR (lacZ) | (SEQ ID NO: 64) |
| lacZ-F | TTCAATGCTGTCAGGTGCTC | PCR genotyping (lacZ) | (SEQ ID NO: 65) |
| lacZ-R | GCCATGTGTCTCAATGTTGG | PCR genotyping (lacZ) | (SEQ ID NO: 66) |
| rs7569946-F | GTCTGCCCTCTTTTGAGCTG | haplotyping fusion PCR | (SEQ ID NO: 67) |
| r57569946-R | GACTCCAGACAATCGCCTTT | haplotyping fusion PCR | (SEQ ID NO: 68) |
| r57569946-R-rc- | AAAGGCGATTGTCTGGAGTCAACCTT | bridging primer, haplotyping fusion | (SEQ ID NO: 69) |
| r51427407-F | CTTAGCACCCACAAAC | PCR | (SEQ ID NO: 70) |
| r51427407-R | CATGTTACTGCAACTTGCTTTTT | haplotyping fusion PCR | (SEQ ID NO: 71) |
| r57569946-nested-F | AGATCCCTCCGTCCAGCTC | haplotyping fusion PCR | (SEQ ID NO: 72) |
| r51427407-nested-R | TGAAAGTTCAAGTAGATATCAGAAGG | haplotyping fusion PCR | (SEQ ID NO: 73) |
| 3C-hBCL11A-150.6-F | AGCAAACCACACAGACTGAAGA | 3C | (SEQ ID NO: 74) |
| 3C-hBCL11A-140.9-F | CCAGAGCCATTTACGTCACA | 3C | (SEQ ID NO: 75) |
| 3C-hBCL11A-114.1-F | CAGAAGGGAATAAGGTACTCTGGA | 3C | (SEQ ID NO: 76) |
| 3C-hBCL11A-111.5-F | GTTTGGGCCTCAAGGTCTTT | 3C | (SEQ ID NO: 77) |
| 3C-hBCL11A-109.1-F | GAGGTTGGGAGTAAGCATTCTG | 3C | (SEQ ID NO: 78) |
| 3C-hBCL11A-100.7-F | ACGCATCAGAATGCCCATAG | 3C | (SEQ ID NO: 79) |
| 3C-hBCL11A-92.3-F | TTTTGAAAGAAAACGCTGACA | 3C | (SEQ ID NO: 80) |
| 3C-hBCL11A-80.2-F | TTCCAGCTGGTTAAATTTAGGG | 3C | (SEQ ID NO: 81) |
| 3C-hBCL11A-77.2-F | AGAAGGGGCCAGAAGAACAG | 3C | (SEQ ID NO: 82) |
| 3C-hBCL11A-72.5-F | CCTTCTTTTTCTTTCTTGGTTGC | 3C | (SEQ ID NO: 83) |
| 3C-hBCL11A-66.8-F | CCCTGCGTGCCATTAAAATA | 3C | (SEQ ID NO: 84) |
| 3C-hBCL11A-61.2-F | AAAGGCCTTGGGAAGAAAGA | 3C | (SEQ ID NO: 85) |
| 3C-hBCL11A-59.1-F | GCAAGTCAGTTGGGAACACA | 3C | (SEQ ID NO: 86) |
| 3C-hBCL11A-57.1-F | GGACTCAGTGGCCTCTTTTG | 3C | (SEQ ID NO: 87) |
| 3C-hBCL11A-52.2-F | CTGTCTCTGTCTCCCCCAAG | 3C | (SEQ ID NO: 88) |
| 3C-hBCL11A-47-F | CCAATGCTCCTGTAACAAAGG | 3C | (SEQ ID NO: 89) |
| 3C-hBCL11A-43.5-F | AATGCAGTAGGCAAAGAAGCA | 3C | (SEQ ID NO: 90) |

TABLE 8-continued

Oligonucleotide sequences.

| Name | Sequence | Assay | |
|---|---|---|---|
| 3C-hBCL11A-38.6-F | GAAATTTGGAAGGCCACAGA | 3C | (SEQ ID NO: 91) |
| 3C-hBCL11A-29.3-F | GCTTGCAACAATTAAAAGATGG | 3C | (SEQ ID NO: 92) |
| 3C-hBCL11A-27.1-F | GGTGACAAGGGAGAACCACT | 3C | (SEQ ID NO: 93) |
| 3C-hBCL11A-20.9-F | TGATTTCCTTGCAGCCTTTT | 3C | (SEQ ID NO: 94) |
| 3C-hBCL11A-8.6-F | CACACCCACAGCAACAAATG | 3C | (SEQ ID NO: 95) |
| 3C-hBCL11Apromoter-R | TGCAGAGATCCCCCAAAGTA | 3C | (SEQ ID NO: 96) |
| 3C-hBCL11A-n8.3-F | CTCAGGGAGCAAGGGAAATA | 3C | (SEQ ID NO: 97) |
| 3C-hBCL11A-n12.6-F | CCCTCCCAACAGGGATTTAT | 3C | (SEQ ID NO: 98) |
| 3C-hBCL11A-n19.5-F | CAAAATTGAACACCTATGGTCTGA | 3C | (SEQ ID NO: 99) |
| 3C-hBCL11A-n29.8-F | AGGAAGACTTTGGCCTCCAT | 3C | (SEQ ID NO: 100) |
| 3C-hBCL11A-n34.6-F | TTCCAAACAATTATACACCAACAAA | 3C | (SEQ ID NO: 101) |
| 3C-hBCL11A-n54-F | TTTCATGGGAATAGCCAAC | 3C | (SEQ ID NO: 102) |
| 3C-hBCL11A-n78.2-F | CCCTACTTGTTATTTGCTTCTGC | 3C | (SEQ ID NO: 103) |
| 3C-hBCL11A-n104.4-F | AGCTGAAGTTTCAGGGACCA | 3C | (SEQ ID NO: 104) |
| 3C-LCR-HS1-F | CCACACCTGCCTTCCTTAGA | 3C | (SEQ ID NO: 105) |
| 3C-LCR-H53-F | TGCATATGATGGGGTAGCAG | 3C | (SEQ ID NO: 106) |
| ChIP-hBCL11A-68.7-F | AAGAGAAGGGGGAATTTGGA | ChIP-qPCR | (SEQ ID NO: 107) |
| ChIP-hBCL11A-68.7-R | TGGTGATAAGGGCAGGAAAC | ChIP-qPCR | (SEQ ID NO: 108) |
| ChIP-hBCL11A-65.5-F | AGGAAGCTGCAGAAAGGTGA | ChIP-qPCR | (SEQ ID NO: 109) |
| ChIP-hBCL11A-65.5-R | TGCTTCCCCAGGTTTAGATG | ChIP-qPCR | (SEQ ID NO: 110) |
| ChIP-hBCL11A-64.7-F | CCACTGCTACCCAAAACGAT | ChIP-qPCR | (SEQ ID NO: 111) |
| ChIP-hBCL11A-64.7-R | CAAGAGCGAAACTCCACCTC | ChIP-qPCR | (SEQ ID NO: 112) |
| ChIP-hBCL11A-63.9-F | ACTGTGTGCCAAGTGACCAG | ChIP-qPCR | (SEQ ID NO: 113) |
| ChIP-hBCL11A-63.9-R | CAGCTTCCTTCAGGTGCTTC | ChIP-qPCR | (SEQ ID NO: 114) |
| ChIP-hBCL11A-63.1-F | CATGCTGCCTTTGTCTTCTG | ChIP-qPCR | (SEQ ID NO: 115) |
| ChIP-hBCL11A-63.1-R | TGTGGAGCTCTGGAATGATG | ChIP-qPCR | (SEQ ID NO: 116) |
| ChIP-hBCL11A-63.0-F | GAGCTCCACAATCCAACTCC | ChIP-qPCR | (SEQ ID NO: 117) |
| ChIP-hBCL11A-63.0-R | CCAGGAAGGAAATGAGAACG | ChIP-qPCR | (SEQ ID NO: 118) |
| ChIP-hBCL11A-62.5-F | ACCCACAAACATTTCCCTTCT | ChIP-qPCR | (SEQ ID NO: 119) |
| ChIP-hBCL11A-62.5-R | TTTGCTCTTCTCCAGGGTGT | ChIP-qPCR | (SEQ ID NO: 120) |
| ChIP-hBCL11A-62.4-F | TTTAAACAGCCACCCCACAC | ChIP-qPCR | (SEQ ID NO: 121) |
| ChIP-hBCL11A-62.4-R | ACCACGTAGTTGGGCTTCAC | ChIP-qPCR | (SEQ ID NO: 122) |
| ChIP-hBCL11A-62.2-F | TTTCAACCATGGTCATCTGC | ChIP-qPCR | (SEQ ID NO: 123) |
| ChIP-hBCL11A-62.2-R | CCCTCTGGCATCAAAATGAG | ChIP-qPCR | (SEQ ID NO: 124) |
| ChIP-hBCL11A-61.8-F | GAACCTGGGAGGCAGAAGAT | ChIP-qPCR | (SEQ ID NO: 125) |
| ChIP-hBCL11A-61.8-R | TTTTTGGTGAGACGGAGATTT | ChIP-qPCR | (SEQ ID NO: 126) |
| ChIP-hBCL11A-61.7-F | CCGGGCAACAAGAGTAAATC | ChIP-qPCR | (SEQ ID NO: 127) |
| ChIP-hBCL11A-61.7-R | ATGCCTAGGGTGTTTTGACG | ChIP-qPCR | (SEQ ID NO: 128) |

TABLE 8-continued

Oligonucleotide sequences.

| Name | Sequence | Assay | |
|---|---|---|---|
| ChIP-hBCL11A-61.5-F | CTCCGTGTTGAGAGCCAAGT | ChIP-qPCR | (SEQ ID NO: 129) |
| ChIP-hBCL11A-61.5-R | TGTGTGGACTGCCTTTTCTG | ChIP-qPCR | (SEQ ID NO: 130) |
| ChIP-hBCL11A-61.3-F | CAGAAAAGGCAGTCCACACA | ChIP-qPCR | (SEQ ID NO: 131) |
| ChIP-hBCL11A-61.3-R | CCTCTCCAGATTCCCTCTCA | ChIP-qPCR | (SEQ ID NO: 132) |
| ChIP-hBCL11A-61.0-F | AGCGAGACCCTGTCTCAAAA | ChIP-qPCR | (SEQ ID NO: 133) |
| ChIP-hBCL11A-61.0-R | TCCAGCAGGCTTCAAAAAGT | ChIP-qPCR | (SEQ ID NO: 134) |
| ChIP-hBCL11A-60.8-F | GGTGGATAACCCCATCTCAG | ChIP-qPCR | (SEQ ID NO: 135) |
| ChIP-hBCL11A-60.8-R | GGAAATGAGAATGCCCTTTG | ChIP-qPCR | (SEQ ID NO: 136) |
| ChIP-hBCL11A-60.5-F | CAGTCTAGAAAGCCCCCTCA | ChIP-qPCR | (SEQ ID NO: 137) |
| ChIP-hBCL11A-60.5-R | GTGGGGGTTCAGTGGTTAGA | ChIP-qPCR | (SEQ ID NO: 138) |
| ChIP-hBCL11A-60.3-F | TCCATGGTGTGGAGTGTGTT | ChIP-qPCR | (SEQ ID NO: 139) |
| ChIP-hBCL11A-60.3-R | ACCCACATGGCAACCAATAG | ChIP-qPCR | (SEQ ID NO: 140) |
| ChIP-hBCL11A-60.0-F | CCATTCCCTGGAGAGTTCAA | ChIP-qPCR | (SEQ ID NO: 141) |
| ChIP-hBCL11A-60.0-R | GGGGTCTCTTCCCATCATTT | ChIP-qPCR | (SEQ ID NO: 142) |
| ChIP-hBCL11A-59.9-F | ATGGGAAGAGACCCCAAAAC | ChIP-qPCR | (SEQ ID NO: 143) |
| ChIP-hBCL11A-59.9-R | GGACTCCGAACACCACACTT | ChIP-qPCR | (SEQ ID NO: 144) |
| ChIP-hBCL11A-59.5-F | GGGATCAGAGGTGAACAGGA | ChIP-qPCR | (SEQ ID NO: 145) |
| ChIP-hBCL11A-59.5-R | TTTAATCAGCTTCCGCCACT | ChIP-qPCR | (SEQ ID NO: 146) |
| ChIP-hBCL11A-59.0-F | TGGGGAGAGAAGAGTGGAAA | ChIP-qPCR | (SEQ ID NO: 147) |
| ChIP-hBCL11A-59.0-R | TTGCCAATTGGAGATTAGGG | ChIP-qPCR | (SEQ ID NO: 148) |
| ChIP-hBCL11A-58.7-F | TGCTCCGAGCTTGTGAACTA | ChIP-qPCR | (SEQ ID NO: 149) |
| ChIP-hBCL11A-58.7-R | GGGAAAGGGCCTGATAACTT | ChIP-qPCR | (SEQ ID NO: 150) |
| ChIP-hBCL11A-58.3-F | GAGAGTGCAGACAGGGGAAG | ChIP-qPCR | (SEQ ID NO: 151) |
| ChIP-hBCL11A-58.3-R | CCTCTTTCGGAAGGCTCTCT | ChIP-qPCR | (SEQ ID NO: 152) |
| ChIP-hBCL11A-58.0-F | TGGACTTTGCACTGGAATCA | ChIP-qPCR | (SEQ ID NO: 153) |
| ChIP-hBCL11A-58.0-R | GATGGCTGAAAAGCGATACA | ChIP-qPCR | (SEQ ID NO: 154) |
| ChIP-hBCL11A-57.3-F | GGGGAGATGATTGAAAGCAA | ChIP-qPCR | (SEQ ID NO: 155) |
| ChIP-hBCL11A-57.3-R | AGAACTTTCCCGGTTCTGGT | ChIP-qPCR | (SEQ ID NO: 156) |
| ChIP-hBCL11A-57.0-F | GCTCTGGACACACAGCAAAA | ChIP-qPCR | (SEQ ID NO: 157) |
| ChIP-hBCL11A-57.0-R | TCAAATCCTTGCCTTGAACC | ChIP-qPCR | (SEQ ID NO: 158) |
| ChIP-hBCL11A-56.6-F | CCTCAAATCTCCCTCACTGG | ChIP-qPCR | (SEQ ID NO: 159) |
| ChIP-hBCL11A-56.6-R | GGGAAATGGGTCCTGCTTTA | ChIP-qPCR | (SEQ ID NO: 160) |
| ChIP-hBCL11A-56.3-F | AGGGAGTACACCGCAGACAC | ChIP-qPCR | (SEQ ID NO: 161) |
| ChIP-hBCL11A-56.3-R | AAGGAAGGCTGCAAGGAAAT | ChIP-qPCR | (SEQ ID NO: 162) |
| ChIP-hBCL11A-55.9-F | GACTTAAACTGCCGCTCCTG | ChIP-qPCR | (SEQ ID NO: 163) |
| ChIP-hBCL11A-55.9-R | TGACTGGTAAGAGCCGATTG | ChIP-qPCR | (SEQ ID NO: 164) |
| ChIP-hBCL11A-55.3-F | GCTGGGGTGAGTCAAAAGTC | ChIP-qPCR | (SEQ ID NO: 165) |
| ChIP-hBCL11A-55.3-R | GGTCACCTTAAGGAGCCACA | ChIP-qPCR | (SEQ ID NO: 166) |

TABLE 8-continued

Oligonucleotide sequences.

| Name | Sequence | Assay | |
|---|---|---|---|
| ChlP-hBCL11A-54.8-F | GCACCTGCATTTGTTTTTCA | ChlP-qPCR | (SEQ ID NO: 167) |
| ChlP-hBCL11A-54.8-R | GGGTCAGATCACCTCTGCTC | ChlP-qPCR | (SEQ ID NO: 168) |
| ChlP-hBCL11A-54.4-F | AGGCATCCAAAGGGAAGAAT | ChlP-qPCR | (SEQ ID NO: 169) |
| ChlP-hBCL11A-54.4-R | GAAGATAATGGCAGCCCAGA | ChlP-qPCR | (SEQ ID NO: 170) |
| ChlP-hBCL11A-54.0-F | TGGGAAAGGTTGCACATTCT | ChlP-qPCR | (SEQ ID NO: 171) |
| ChlP-hBCL11A-54.0-R | GGGCCTCAGGCTCTTTATCT | ChlP-qPCR | (SEQ ID NO: 172) |
| ChlP-hBCL11A-53.4-F | CCACTGCCAGGCTGTTTACT | ChlP-qPCR | (SEQ ID NO: 173) |
| ChlP-hBCL11A-53.4-R | GACCGAAAGGAGGAGAGGAG | ChlP-qPCR | (SEQ ID NO: 174) |
| ChlP-hBCL11A-53.1-F | CAGTTCCCCCATTATGCACT | ChlP-qPCR | (SEQ ID NO: 175) |
| ChlP-hBCL11A-53.1-R | CCCTTCTCTGAAGGCACATC | ChlP-qPCR | (SEQ ID NO: 176) |
| ChlP-hBCL11A-52.7-F | TTCAAGCCTTGGTGGATAGG | ChlP-qPCR | (SEQ ID NO: 177) |
| ChlP-hBCL11A-52.7-R | GCCAGGAAATTGGTGGTAGA | ChlP-qPCR | (SEQ ID NO: 178) |
| ChlP-hBCL11A-52.3-F | TGCCCACATGAGACATCTTT | ChlP-qPCR | (SEQ ID NO: 179) |
| ChlP-hBCL11A-52.3-R | AAATTGGCTGCCATTGAATC | ChlP-qPCR | (SEQ ID NO: 180) |
| ChlP-hBCL11A-51.3-F | CCACCAGAAGTCCTGGAAAA | ChlP-qPCR | (SEQ ID NO: 181) |
| ChlP-hBCL11A-51.3-R | TTGGAGGGACCTGATCTCTG | ChlP-qPCR | (SEQ ID NO: 182) |
| ChlP-hBCL11A-50.2-F | CCAAGATGGAGAAGCCACAT | ChlP-qPCR | (SEQ ID NO: 183) |
| ChlP-hBCL11A-50.2-R | TCTGTCTTGGGTCTCCTGGT | ChlP-qPCR | (SEQ ID NO: 184) |
| ChlP-hBCL11A-49.8-F | GAGAAGCCCTCAGCAAACAC | ChlP-qPCR | (SEQ ID NO: 185) |
| ChlP-hBCL11A-49.8-R | GGTTGCATCTTGGCTCCTAA | ChlP-qPCR | (SEQ ID NO: 186) |
| ChlP-hBCL11A-49.5-F | GAAATGCAGGAAAGGAACGA | ChlP-qPCR | (SEQ ID NO: 187) |
| ChlP-hBCL11A-49.5-R | TCTAGCAGATGGGGTTTTGG | ChlP-qPCR | (SEQ ID NO: 188) |
| ChlP-hOct4-prom-F | AGTCTGGGCAACAAAGTGAGA | ChlP-qPCR | (SEQ ID NO: 189) |
| ChlP-hOct4-prom-R | AGAAACTGAGGAGAAGGATG | ChlP-qPCR | (SEQ ID NO: 190) |
| ChlP-hHS3-F | ATAGACCATGAGTAGAGGGCAGAC | ChlP-qPCR | (SEQ ID NO: 191) |
| ChlP-hHS3-R | TGATCCTGAAAACATAGGAGTCAA | ChlP-qPCR | (SEQ ID NO: 192) |
| ChlP-hHS-40-F | CAGATAACTGGGCCAACCAT | ChlP-qPCR | (SEQ ID NO: 193) |
| ChlP-hHS-40-R | ATTCACCCCTTTCCCTTGTC | ChlP-qPCR | (SEQ ID NO: 194) |
| ChlP-hGAPDH-F | CGTAGCTCAGGCCTCAAGAC | ChlP-qPCR | (SEQ ID NO: 195) |
| ChlP-hGAPDH-R | CGAACAGGAGGAGCAGAGAG | ChlP-qPCR | (SEQ ID NO: 196) |

Oligonucleotides used in indicated experiments.

What is claimed:

1. A human hematopoietic progenitor cell comprising at least one genetic modification within chromosome 2 between positions 60,716,189 and 60,728,612 (according to UCSC Genome Browser hg 1.9 human genome assembly), wherein the human hematopoietic progenitor cell comprises i) a vector comprising a regulatory element operably linked to a coding sequence of a DNA-targeting endonuclease comprising a TAL DNA binding domain or ii) an RNA encoding a DNA-targeting endonuclease comprising a TAL DNA binding domain; wherein the DNA-targeting endonuclease binds to and cleaves the genomic DNA of the cell within the chromosome 2 between positions 60,716,189 and 60,728,612 to generate the at least one genetic modification; wherein the at least one genetic modification is an insertion or a deletion that disrupts DNAse hypersensitive sites +62, +58, or +55 therein; and wherein the at least one genetic modification reduces BCL11A mRNA and protein expression in the human hematopoietic progenitor cell or its progeny.

2. The human hematopoietic progenitor cell of claim 1, wherein the at least one genetic modification is the insertion.

3. The human hematopoietic progenitor cell of claim 1, wherein the at least one genetic modification is the deletion.

4. The human hematopoietic progenitor cell of claim 3, wherein the deletion removes the entire region between chromosome 2 location 60,716,189 and 60,728,612 or removes one or more DHSs in the region.

5. The human hematopoietic progenitor cell of claim 4, wherein the deletion removes the entire region between chromosome 2 location 60,716,189 and 60,728,612.

6. The human hematopoietic progenitor cell of claim 4, wherein the deletion removes the entire region between chromosome 2 location 60,717,492 and 60,718,860.

7. The human hematopoietic progenitor cell of claim 4, wherein the deletion removes the entire region between chromosome 2 location 60,721,411 and 60,722,674.

8. The human hematopoietic progenitor cell of claim 4, wherein the deletion removes the entire region between chromosome 2 location 60,724,802 and 60,726,084.

9. The human hematopoietic progenitor cell of claim 4, wherein the deletion disrupts the DHS +62.

10. The human hematopoietic progenitor cell of claim 4, wherein the deletion disrupts the DHS +58.

11. The human hematopoietic progenitor cell of claim 4, wherein the deletion disrupts the DHS +55.

12. The human hematopoietic progenitor cell of claim 1, wherein the human hematopoietic progenitor cell is modified ex vivo.

13. The human hematopoietic progenitor cell of claim 1, wherein the cell is an erythroid lineage cell.

14. A pharmaceutical composition comprising a pharmaceutically acceptable carrier and a human hematopoietic progenitor cell comprising at least one genetic modification within chromosome 2 between positions 60,716,18960,728,612 (according to UCSC Genome Browser hg 1.9 human genome assembly), wherein the at least one genetic modification is an insertion or a deletion that disrupts DNAse hypersensitive sites +62, +58, or +55 therein, and wherein the at least one genetic modification reduces BCL11A mRNA and protein expression in the human hematopoietic progenitor cell or its progeny.

* * * * *

UNITED STATES PATENT AND TRADEMARK OFFICE
CERTIFICATE OF CORRECTION

PATENT NO. : 10,472,619 B2  
APPLICATION NO. : 15/816083  
DATED : November 12, 2019  
INVENTOR(S) : Stuart H. Orkin, Daniel E. Bauer and Jian Xu Page 1 of 1

It is certified that error appears in the above-identified patent and that said Letters Patent is hereby corrected as shown below:

In the Specification

At Column 1, Line 23-26, please delete "This invention was made with Government support under Grant No. 5R01HL032259 awarded by the National Institutes of Health. The Government has certain rights in the invention." and insert the following -- This invention was made with government support under grant numbers HL032259 and DK093705 awarded by the National Institutes of Health. The Government has certain rights in the invention. --

Signed and Sealed this  
Twenty-fourth Day of December, 2019

Andrei Iancu  
*Director of the United States Patent and Trademark Office*